US007531338B2

(12) United States Patent
Liu et al.

(10) Patent No.: US 7,531,338 B2
(45) Date of Patent: May 12, 2009

(54) PURIFIED AND ISOLATED HEPARAN SULFATE 3-O-SULFOTRANSFERASE ISOFORM 5 NUCLEIC ACIDS AND POLYPEPTIDES AND THERAPEUTIC AND SCREENING METHODS USING SAME

(75) Inventors: Jian Liu, Chapel Hill, NC (US); Guoqing Xia, Hamburg (DE); Jinghua Chen, Chapel Hill, NC (US); Michael B. Duncan, Chapel Hill, NC (US); Deepak Shukla, Skokie, IL (US); Vaibhav Tiwari, Chicago, IL (US); Anders Malmstrom, Lund (SE)

(73) Assignees: The University of North Carolina at Chapel Hill, Chapel Hill, NC (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 10/520,341

(22) PCT Filed: Jul. 7, 2003

(86) PCT No.: PCT/US03/21094

§ 371 (c)(1),
(2), (4) Date: Oct. 20, 2005

(87) PCT Pub. No.: WO2004/005475

PCT Pub. Date: Jan. 15, 2004

(65) Prior Publication Data

US 2006/0165673 A1 Jul. 27, 2006

Related U.S. Application Data

(60) Provisional application No. 60/394,199, filed on Jul. 5, 2002.

(51) Int. Cl.
*C12N 9/10* (2006.01)
*C12N 9/00* (2006.01)
*C07H 21/04* (2006.01)

(52) U.S. Cl. .................. 435/193; 435/183; 536/23.2
(58) Field of Classification Search .............. 435/193, 435/183; 536/23.2
See application file for complete search history.

(56) References Cited

FOREIGN PATENT DOCUMENTS

WO WO 99/22005 * 5/1999

OTHER PUBLICATIONS

Myette et al. Expression in *Escherichia coli*, purification and kinetic characterization of human heparan sulfate 3-O-sulfotransferase-1. Biochem Biophys Res Commun. 290(4): 1206-13, 2002.*

Xia et al, Heparan sulfate 3-O-sulfotransferase isoform 5 generates both an antithrombin-binding site and an entry receptor for herpes simplex virus, type 1. J Biol Chem. Oct. 4, 2002;277(40):37912-9. Epub Jul. 23, 2002.*

Kennell, Principals and practices of nucleic acid hybridization. Prog Nucleic Acid Res Mol Biol. 11:259-301, 1971.*

Munoz et al. Affinity, kinetic, and structural study of the interaction of 3-O-sulfotransferase isoform 1 with heparan sulfate, Biochemistry, 45(16): 5122-8, 2006.*

International Preliminary Examination Report for corresponding PCT Application No. PCT/US03/21094 dated Jun. 8, 2005.

International Search Report for corresponding PCT Appl. No. PCT/US03/21094 dated Oct. 7, 2004.

Xia et al., "Heparan Sulfate 3-*O*-Sulfotansferase Isoform 5 Generates Both an Antithrombin-binding Site and an Entry Receptor for Herpes Simplex virus, Type 1", *Journal of Biological Chemistry*, 277 (40): 37912-37919, Oct. 4, 2002.

Mochizuki et al., "Characterization of a Heparan Sulfate 3-*0*-Sulfotransferase-5, an Enzyme Synthesizing a Tetrasulfated Disaccharide", *Journal of Biological Chemistry*, 278 (29): 26780-26787, Jul. 18, 2003.

Xu et al., "characterization of Heparan Sulphate Sulpotransferase Isoform 6 and Its Role in Assisting the Entry of Herpes Simplex Virus, Type 1", *Biochemical Journal*: 1-35, Aug. 10, 2004.

Yabe et al., "Portable Sulphotransferase Fomain Determines Sequence Specificity of Heparan Sulphate 3-*O*-Sulfotransferases", *Biochemical Journal*, 359: 235-241, 2001.

Kramer et al., "Heparan Sulfate Core Proteins in Cell-Cell Signaling", *Annu. Rev. Genet.*, 37: 461-484, Jul. 16, 2003.

Print out of EMBL Sequence Version Archiving for EMBL Accession No. AF503292, printed on Sep. 15, 2004.

* cited by examiner

*Primary Examiner*—Thaian N. Ton
*Assistant Examiner*—Wu-Cheng Winston Shen
(74) *Attorney, Agent, or Firm*—Jenkins, Wilson, Taylor & Hunt, P.A.

(57) ABSTRACT

3-OST-5 proteins, and nucleic acid molecules encoding the same. Recombinant host cells, recombinant nucleic acids and recombinant proteins are also disclosed, along with methods of producing each. Isolated and purified antibodies to 3-OST-5 homologs, and methods of producing the same, are also disclosed. 3OST-5 gene products have biological activity in specific heparan sulfate 3-O-sulfotransferase reactions. These reactions provide unique modified heparan sulfate. Thus, therapeutic methods involving this activity are also disclosed.

4 Claims, 17 Drawing Sheets

Figure 1

```
atgctattcaaacagcaggcgtggctgagacagaagctcctgcgttgccgcttggagcctt ccgttgggagtctcctgtatcagtcgccaga     90
 M  L  F  K  Q  Q  A  W  L  R  Q  K  L  L  V  L  G  S  L  L  Y  L  L  V  A  R       30 gttgggagcttggataggctacaaccattgccccattgaaggtcgactgggtgagccgcac tcaggctgaattcccacttcgcgcc           180
 V  G  S  L  D  R  L  Q  P  I  C  P  I  E  G  R  L  G  G  A  R  T  Q  A  E  F  P  L  R  A      60 ctgcagttcaagcgtggcctgctgcacgagttccggcgaaggggcaacgcttccaaggagc aggttcgctccatgacctggtccagcagctc    270
 L  Q  F  K  R  G  L  L  H  E  F  R  R  K  G  N  A  S  K  E  Q  V  R  L  H  D  L  V  Q  Q  L  90
                                                    • cccaaggccattatcattgggtgagaaggaggcacaaggcgcctgcttgaatctgaacctac atcggcagtagtcaagcctct            360
 P  K  A  I  I  I  G  V  R  K  G  G  T  R  A  L  L  E  M  L  N  L  H  P  A  V  V  K  A  S     120 caagaaatccactttttgataatgatgagaacatatttatcacagagaggttccagaaagat tacaaaatgaactcatcaagttgttgatc   450
 Q  E  I  H  F  F  D  N  D  E  N  Y  G  K  G  I  E  W  Y  R  K  K  M  P  F  S  Y  P  P  Q     150 atcacaattgaaaagagcccagcccatatttatcacagagaggttccagaaagattacaaa atgaactcatcaagttgttgatc           540
 I  T  I  E  K  S  P  A  Y  F  I  T  E  E  V  P  E  R  I  Y  K  M  N  S  I  K  L  L  I        180
                                                                        • attgtcagggagccaaccacacaagagctatttctgattatacatcaggtgctagagggga aggaggaagaacaaaactattacaagttt   630
 I  V  R  E  P  T  T  R  A  I  S  D  Y  T  Q  V  L  E  G  K  E  R  K  N  K  T  Y  Y  K  F    210
                                                             • gagaagctggcccatagacccttaatacatgcgaagtgaacacaaaatacaaagcagtaa gaaccagcatctacacaaacatctggaaagg   720
 E  K  L  A  I  D  P  N  T  C  E  V  N  T  K  Y  K  A  V  R  T  S  I  Y  T  K  H  L  E  R    240 tggttgaatactttccaattgagcaatttcatgtcgtcgatggacgtgatagattcgcct cagaactctgcctgccagaacttcagctgtggag 810
 W  L  K  Y  F  P  I  E  Q  F  H  V  V  D  G  D  R  L  I  T  E  P  L  P  E  L  Q  L  V  E    270 aagttcctaaatctgcctccaaggataagtcaatacaattatattcaatgctaccagaggg ttttactgcttgcggttaatattatc       900
 K  F  L  N  L  P  P  R  I  S  Q  Y  N  L  Y  F  N  A  T  R  G  F  Y  C  L  R  F  N  I  I    300
                                               • tttaataagtgcctggctggggcagcaaggggcgcattcatccagaggtgaccccctgtca ttactaaattgcaaattctttcatcct     990
 F  N  K  C  L  A  G  S  K  G  R  I  H  P  E  V  D  P  S  V  I  T  K  L  R  R  K  F  F  H  P  330 tttaatcaaaatttaccagatcactgggaggacattgaactgccctaa    1041
 F  N  Q  K  F  Y  Q  I  T  G  R  T  L  N  W  P  *   346
```

Figure 2

Figure 4
A.
B.
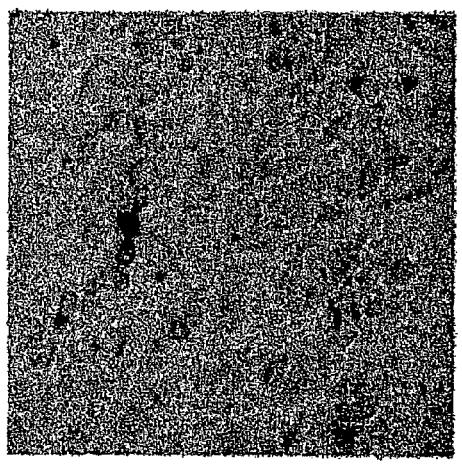
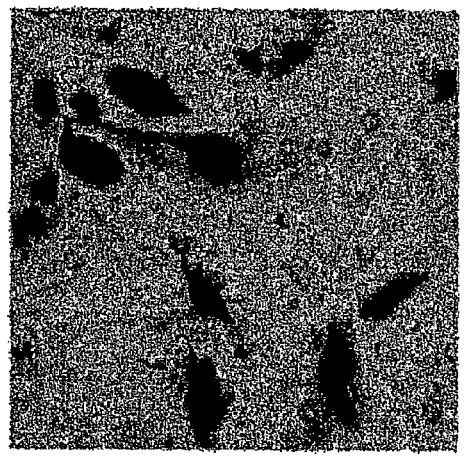

Figure 5
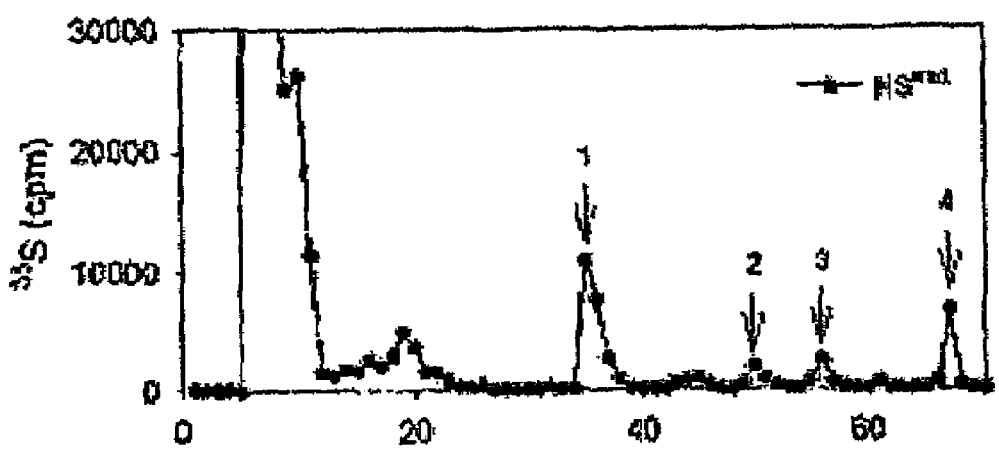
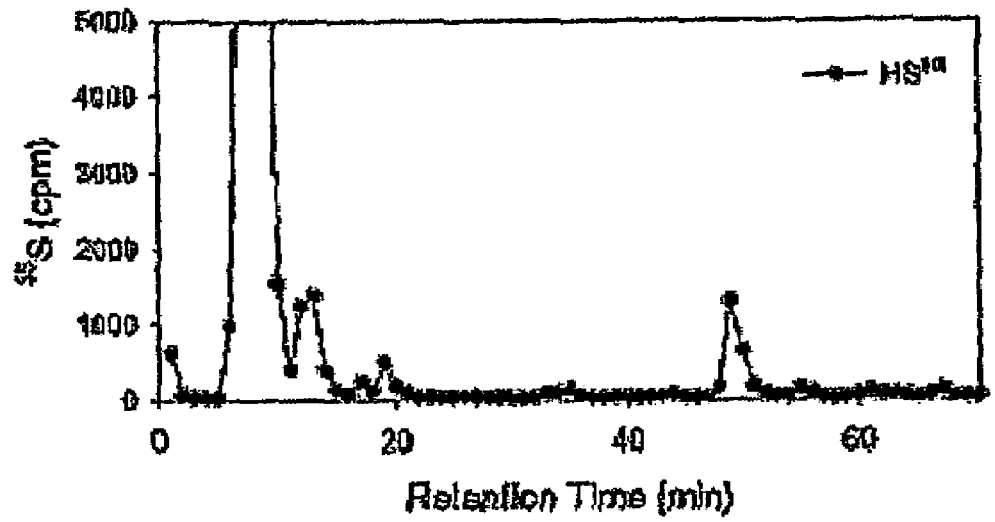

Figure 10B

MKFLVNVALV FMVVYISYIY A↓DRWIPRVGS LDRLQPICPI EGRLGGARTQ AEFPLRALQF
<u>Honeybee Melittin signal</u>                <u>B2 and B3</u>       <u>B2 and B3</u>

KRGLLHEFRK GNASKEQVRL HDLVQQLPKA IIIGVRKGGT RALLEMLNLH PAVVKASQEI
<u>B2 and B3</u>       <u>B2 and B3</u>                            <u>B2 and</u>

HFFDNDENYG KGIEWYRKKM PFSYPQQITI EKSPAYFITE EVPERIYKMN SSIKLLIIVR
<u>B3</u>                            <u>B2 and B3</u>                   <u>B2 and</u>

EPTTRAISDY TQVLEGKERK NKTYYKFEKL AIDPNTCEVN TKYKAVRTSI YTKHLERWLK
<u>B3</u>      <u>B1</u>

YFPPIEQFHVV DGDRLITEPL PELQLVEKFL NLPPRISQYN LYFNATRGFY CLRFNIIFNK
                       <u>B2 and B3</u>

CLAGSKGRIH PEVDPSVITK LRKFFHPFNQ KFYQITGRTL NWP
<u>B2 and B3</u>

Figure 12
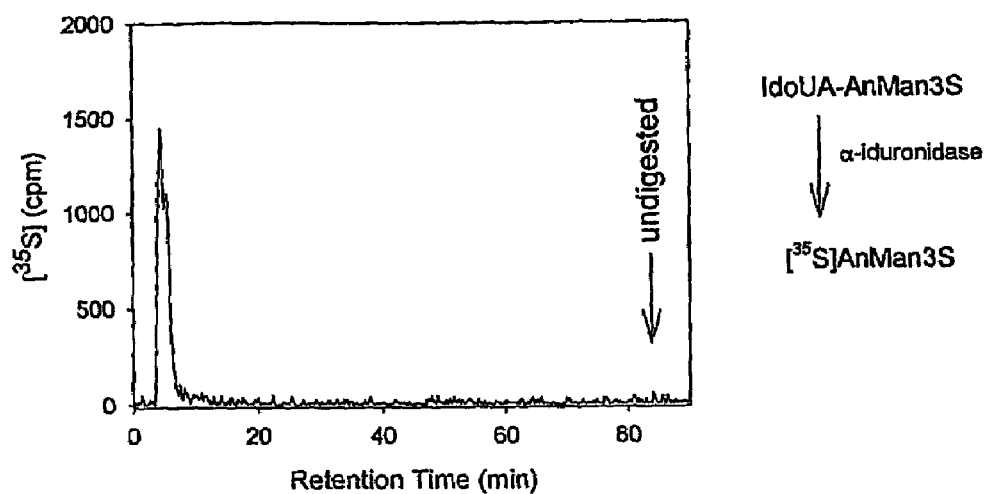
A.
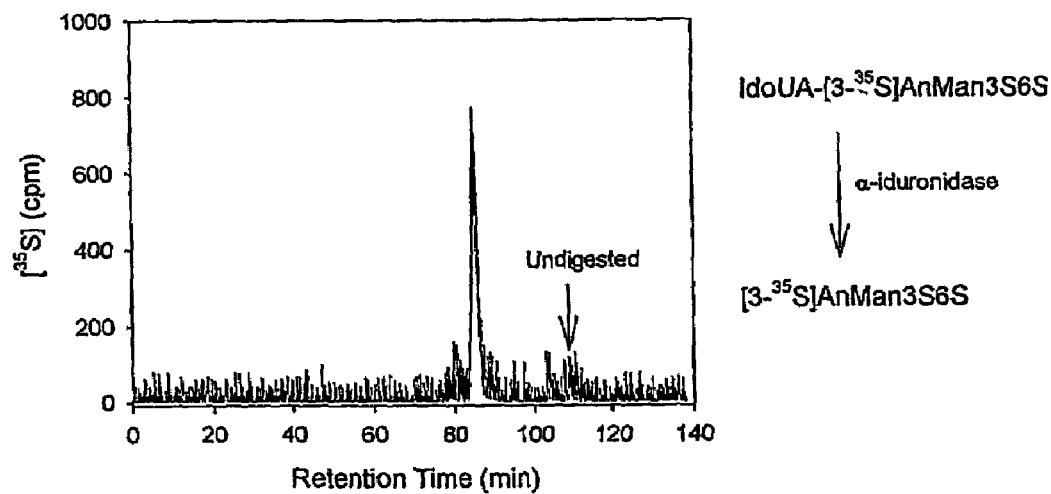
B.

Figure 14
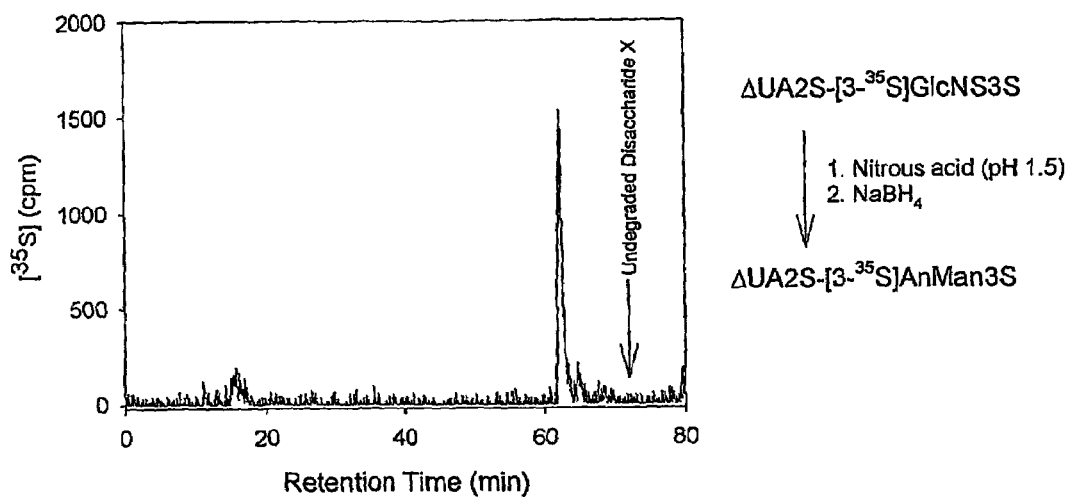
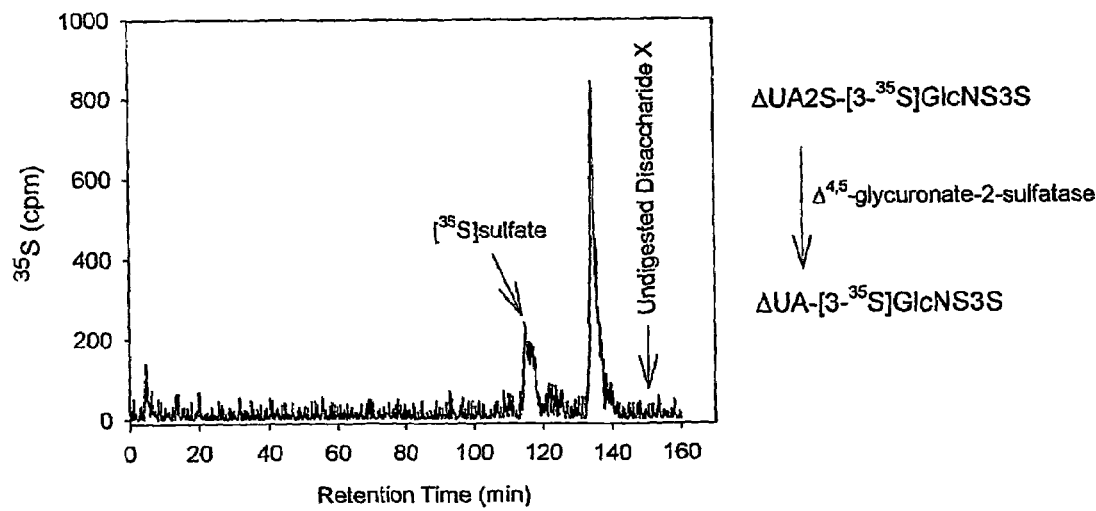

Figure 15
A.
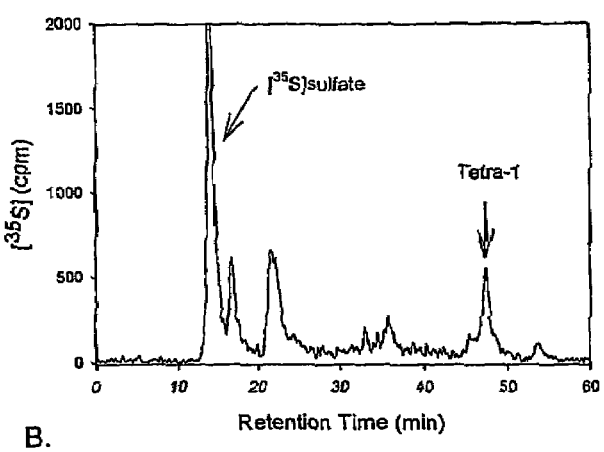
B.
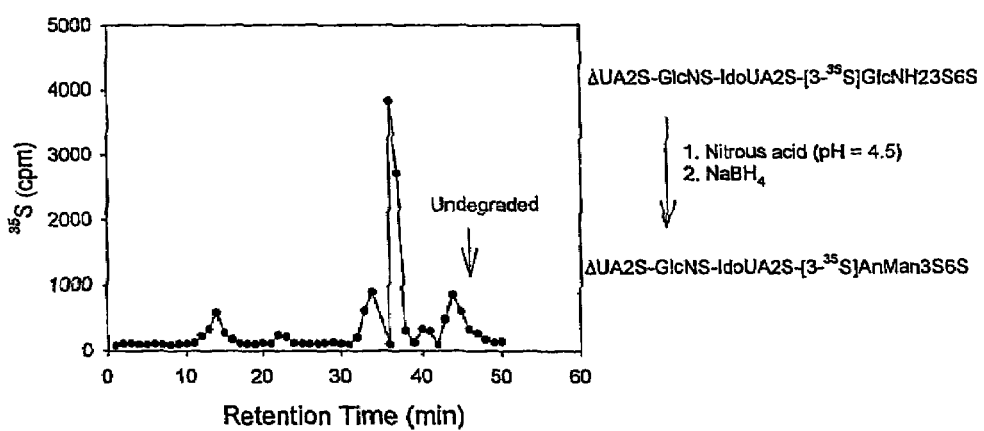

SEQUENCE LISTING

<160> NUMBER OF SEQ ID NOS: 12

<210> SEQ ID NO 1
<211> LENGTH: 1041
<212> TYPE: DNA
<213> ORGANISM: Homo sapiens
<220> FEATURE:
<221> NAME/KEY: CDS
<222> LOCATION: (1)..(1041)

<400> SEQUENCE: 1

| | | | | | | | | | | | | | | | | |
|---|---|---|---|---|---|---|---|---|---|---|---|---|---|---|---|---|
| atg | cta | ttc | aaa | cag | cag | gcg | tgg | ctg | aga | cag | aag | ctc | ctg | gtg | ctg | 48 |
| Met | Leu | Phe | Lys | Gln | Gln | Ala | Trp | Leu | Arg | Gln | Lys | Leu | Leu | Val | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gga | agc | ctt | gcc | gtt | ggg | agt | ctc | ctg | tat | cta | gtc | gcc | aga | gtt | ggg | 96 |
| Gly | Ser | Leu | Ala | Val | Gly | Ser | Leu | Leu | Tyr | Leu | Val | Ala | Arg | Val | Gly | |
| | | | | 20 | | | | | 25 | | | | | 30 | | |

| | | | | | | | | | | | | | | | | |
|---|---|---|---|---|---|---|---|---|---|---|---|---|---|---|---|---|
| agc | ttg | gat | agg | cta | caa | ccc | att | tgc | ccc | att | gaa | ggt | cga | ctg | ggt | 144 |
| Ser | Leu | Asp | Arg | Leu | Gln | Pro | Ile | Cys | Pro | Ile | Glu | Gly | Arg | Leu | Gly | |
| | | | 35 | | | | | 40 | | | | | 45 | | | |

| | | | | | | | | | | | | | | | | |
|---|---|---|---|---|---|---|---|---|---|---|---|---|---|---|---|---|
| gga | gcc | cgc | act | cag | gct | gaa | ttc | cca | ctt | cgc | gcc | ctg | cag | ttt | aag | 192 |
| Gly | Ala | Arg | Thr | Gln | Ala | Glu | Phe | Pro | Leu | Arg | Ala | Leu | Gln | Phe | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| cgt | ggc | ctg | ctg | cac | gag | ttc | cgg | aag | ggc | aac | gct | tcc | aag | gag | cag | 240 |
| Arg | Gly | Leu | Leu | His | Glu | Phe | Arg | Lys | Gly | Asn | Ala | Ser | Lys | Glu | Gln | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtt | cgc | ctc | cat | gac | ctg | gtc | cag | cag | ctc | ccc | aag | gcc | att | atc | att | 288 |
| Val | Arg | Leu | His | Asp | Leu | Val | Gln | Gln | Leu | Pro | Lys | Ala | Ile | Ile | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| ggg | gtg | agg | aaa | gga | ggc | aca | agg | gcc | ctg | ctt | gaa | atg | ctg | aac | cta | 336 |
| Gly | Val | Arg | Lys | Gly | Gly | Thr | Arg | Ala | Leu | Leu | Glu | Met | Leu | Asn | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| cat | ccg | gca | gta | gtc | aaa | gcc | tct | caa | gaa | atc | cac | ttt | ttt | gat | aat | 384 |
| His | Pro | Ala | Val | Val | Lys | Ala | Ser | Gln | Glu | Ile | His | Phe | Phe | Asp | Asn | |
| | | 115 | | | | | 120 | | | | | 125 | | | | |

| | | | | | | | | | | | | | | | | |
|---|---|---|---|---|---|---|---|---|---|---|---|---|---|---|---|---|
| gat | gag | aat | tat | ggt | aag | ggc | att | gag | tgg | tat | agg | aaa | aag | atg | cct | 432 |
| Asp | Glu | Asn | Tyr | Gly | Lys | Gly | Ile | Glu | Trp | Tyr | Arg | Lys | Lys | Met | Pro | |
| 130 | | | | | 135 | | | | | 140 | | | | | | |

| | | | | | | | | | | | | | | | | |
|---|---|---|---|---|---|---|---|---|---|---|---|---|---|---|---|---|
| ttt | tcc | tac | cct | cag | caa | atc | aca | att | gaa | aag | agc | cca | gca | tat | ttt | 480 |
| Phe | Ser | Tyr | Pro | Gln | Gln | Ile | Thr | Ile | Glu | Lys | Ser | Pro | Ala | Tyr | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| atc | aca | gag | gag | gtt | cca | gaa | agg | att | tac | aaa | atg | aac | tca | tcc | atc | 528 |
| Ile | Thr | Glu | Glu | Val | Pro | Glu | Arg | Ile | Tyr | Lys | Met | Asn | Ser | Ser | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| aag | ttg | ttg | atc | att | gtc | agg | gag | cca | acc | aca | aga | gct | att | tct | gat | 576 |
| Lys | Leu | Leu | Ile | Ile | Val | Arg | Glu | Pro | Thr | Thr | Arg | Ala | Ile | Ser | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| tat | act | cag | gtg | cta | gag | ggg | aag | gag | agg | aag | aac | aaa | act | tat | tac | 624 |
| Tyr | Thr | Gln | Val | Leu | Glu | Gly | Lys | Glu | Arg | Lys | Asn | Lys | Thr | Tyr | Tyr | |
| | | 195 | | | | | 200 | | | | | 205 | | | | |

| | | | | | | | | | | | | | | | | |
|---|---|---|---|---|---|---|---|---|---|---|---|---|---|---|---|---|
| aag | ttt | gag | aag | ctg | gcc | ata | gac | cct | aat | aca | tgc | gaa | gtg | aac | aca | 672 |
| Lys | Phe | Glu | Lys | Leu | Ala | Ile | Asp | Pro | Asn | Thr | Cys | Glu | Val | Asn | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| aaa | tac | aaa | gca | gta | aga | acc | agc | atc | tac | acc | aaa | cat | ctg | gaa | agg | 720 |
| Lys | Tyr | Lys | Ala | Val | Arg | Thr | Ser | Ile | Tyr | Thr | Lys | His | Leu | Glu | Arg | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| tgg | ttg | aaa | tac | ttt | cca | att | gag | caa | ttt | cat | gtc | gtc | gat | gga | gat | 768 |
| Trp | Leu | Lys | Tyr | Phe | Pro | Ile | Glu | Gln | Phe | His | Val | Val | Asp | Gly | Asp | |
| | | | 245 | | | | | 250 | | | | | 255 | | | |

| | | | | | | | | | | | | | | | | |
|---|---|---|---|---|---|---|---|---|---|---|---|---|---|---|---|---|
| cgc | ctc | atc | acg | gaa | cct | ctg | cca | gaa | ctt | cag | ctc | gtg | gag | aag | ttc | 816 |
| Arg | Leu | Ile | Thr | Glu | Pro | Leu | Pro | Glu | Leu | Gln | Leu | Val | Glu | Lys | Phe | |
| | | | 260 | | | | | 265 | | | | | 270 | | | |

| | | | | | | | | | | | | | | | | |
|---|---|---|---|---|---|---|---|---|---|---|---|---|---|---|---|---|
| cta | aat | ctg | cct | cca | agg | ata | agt | caa | tac | aat | tta | tac | ttc | aat | gct | 864 |
| Leu | Asn | Leu | Pro | Pro | Arg | Ile | Ser | Gln | Tyr | Asn | Leu | Tyr | Phe | Asn | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| acc | aga | ggg | ttt | tac | tgc | ttg | cgg | ttt | aat | att | atc | ttt | aat | aag | tgc | 912 |
| Thr | Arg | Gly | Phe | Tyr | Cys | Leu | Arg | Phe | Asn | Ile | Ile | Phe | Asn | Lys | Cys | |
| | 290 | | | | | 295 | | | | | 300 | | | | | |

| | | | | | | | | | | | | | | | | |
|---|---|---|---|---|---|---|---|---|---|---|---|---|---|---|---|---|
| ctg | gcg | ggc | agc | aag | ggg | cgc | att | cat | cca | gag | gtg | gac | ccc | tct | gtc | 960 |
| Leu | Ala | Gly | Ser | Lys | Gly | Arg | Ile | His | Pro | Glu | Val | Asp | Pro | Ser | Val | |

```
                305                 310                 315                 320
att act aaa ttg cgc aaa ttc ttt cat cct ttt aat caa aaa ttt tac      1008
Ile Thr Lys Leu Arg Lys Phe Phe His Pro Phe Asn Gln Lys Phe Tyr
                    325                 330                 335 cag atc act ggg agg aca ttg aac tgg ccc taa                          1041
Gln Ile Thr Gly Arg Thr Leu Asn Trp Pro
                340                 345

<210> SEQ ID NO 2
<211> LENGTH: 346
<212> TYPE: PRT
<213> ORGANISM: Homo sapiens

<400> SEQUENCE: 2

Met Leu Phe Lys Gln Gln Ala Trp Leu Arg Gln Lys Leu Leu Val Leu
1               5                   10                  15

Gly Ser Leu Ala Val Gly Ser Leu Leu Tyr Leu Val Ala Arg Val Gly
            20                  25                  30

Ser Leu Asp Arg Leu Gln Pro Ile Cys Pro Ile Glu Gly Arg Leu Gly
        35                  40                  45

Gly Ala Arg Thr Gln Ala Glu Phe Pro Leu Arg Ala Leu Gln Phe Lys
    50                  55                  60

Arg Gly Leu Leu His Glu Phe Arg Lys Gly Asn Ala Ser Lys Glu Gln
65                  70                  75                  80

Val Arg Leu His Asp Leu Val Gln Gln Leu Pro Lys Ala Ile Ile Ile
                85                  90                  95

Gly Val Arg Lys Gly Gly Thr Arg Ala Leu Leu Glu Met Leu Asn Leu
            100                 105                 110

His Pro Ala Val Val Lys Ala Ser Gln Glu Ile His Phe Phe Asp Asn
        115                 120                 125

Asp Glu Asn Tyr Gly Lys Gly Ile Glu Trp Tyr Arg Lys Lys Met Pro
    130                 135                 140

Phe Ser Tyr Pro Gln Gln Ile Thr Ile Glu Lys Ser Pro Ala Tyr Phe
145                 150                 155                 160

Ile Thr Glu Glu Val Pro Glu Arg Ile Tyr Lys Met Asn Ser Ser Ile
                165                 170                 175

Lys Leu Leu Ile Ile Val Arg Glu Pro Thr Thr Arg Ala Ile Ser Asp
            180                 185                 190

Tyr Thr Gln Val Leu Glu Gly Lys Glu Arg Lys Asn Lys Thr Tyr Tyr
        195                 200                 205

Lys Phe Glu Lys Leu Ala Ile Asp Pro Asn Thr Cys Glu Val Asn Thr
    210                 215                 220

Lys Tyr Lys Ala Val Arg Thr Ser Ile Tyr Thr Lys His Leu Glu Arg
225                 230                 235                 240

Trp Leu Lys Tyr Phe Pro Ile Glu Gln Phe His Val Val Asp Gly Asp
                245                 250                 255

Arg Leu Ile Thr Glu Pro Leu Pro Glu Leu Gln Leu Val Glu Lys Phe
            260                 265                 270

Leu Asn Leu Pro Pro Arg Ile Ser Gln Tyr Asn Leu Tyr Phe Asn Ala
        275                 280                 285

Thr Arg Gly Phe Tyr Cys Leu Arg Phe Asn Ile Ile Phe Asn Lys Cys
    290                 295                 300

Leu Ala Gly Ser Lys Gly Arg Ile His Pro Glu Val Asp Pro Ser Val
305                 310                 315                 320

Ile Thr Lys Leu Arg Lys Phe Phe His Pro Phe Asn Gln Lys Phe Tyr
```

```
                    325                 330                 335
Gln Ile Thr Gly Arg Thr Leu Asn Trp Pro
            340                 345

<210> SEQ ID NO 3
<211> LENGTH: 307
<212> TYPE: PRT
<213> ORGANISM: Homo sapiens

<400> SEQUENCE: 3

Met Ala Ala Leu Leu Gly Ala Val Leu Val Ala Gln Pro Gln
1               5                  10                  15

Leu Val Pro Ser Arg Pro Ala Glu Leu Gly Gln Gln Glu Leu Leu Arg
            20                  25                  30

Lys Ala Gly Thr Leu Gln Asp Asp Val Arg Asp Gly Val Ala Pro Asn
        35                  40                  45

Gly Ser Ala Gln Gln Leu Pro Gln Thr Ile Ile Ile Gly Val Arg Lys
    50                  55                  60

Gly Gly Thr Arg Ala Leu Leu Glu Met Leu Ser Leu His Pro Asp Val
65                  70                  75                  80

Ala Ala Ala Glu Asn Glu Val His Phe Phe Asp Trp Glu Glu His Tyr
                85                  90                  95

Ser His Gly Leu Gly Trp Tyr Leu Ser Gln Met Pro Phe Ser Trp Pro
            100                 105                 110

His Gln Leu Thr Val Glu Lys Thr Pro Ala Tyr Phe Thr Ser Pro Lys
        115                 120                 125

Val Pro Glu Arg Val Tyr Ser Met Asn Pro Ser Ile Arg Leu Leu Leu
    130                 135                 140

Ile Leu Arg Asp Pro Ser Glu Arg Val Leu Ser Asp Tyr Thr Gln Val
145                 150                 155                 160

Phe Tyr Asn His Met Gln Lys His Lys Pro Tyr Pro Ser Ile Glu Glu
                165                 170                 175

Phe Leu Val Arg Asp Gly Arg Leu Asn Val Asp Tyr Lys Ala Leu Asn
            180                 185                 190

Arg Ser Leu Tyr His Val His Met Gln Asn Trp Leu Arg Phe Phe Pro
        195                 200                 205

Leu Arg His Ile His Ile Val Asp Gly Asp Arg Leu Ile Arg Asp Pro
    210                 215                 220

Phe Pro Glu Ile Gln Lys Val Glu Arg Phe Leu Lys Leu Ser Pro Gln
225                 230                 235                 240

Ile Asn Ala Ser Asn Phe Tyr Phe Asn Lys Thr Lys Gly Phe Tyr Cys
                245                 250                 255

Leu Arg Asp Ser Gly Arg Asp Arg Cys Leu His Glu Ser Lys Gly Arg
            260                 265                 270

Ala His Pro Gln Val Asp Pro Lys Leu Leu Asn Lys Leu His Glu Tyr
        275                 280                 285

Phe His Glu Pro Asn Lys Lys Phe Phe Glu Leu Val Gly Arg Thr Phe
    290                 295                 300

Asp Trp His
305

<210> SEQ ID NO 4
<211> LENGTH: 406
<212> TYPE: PRT
<213> ORGANISM: Homo sapiens
```

<400> SEQUENCE: 4

```
Met Ala Pro Pro Gly Pro Ala Ser Ala Leu Ser Thr Ser Ala Glu Pro
1               5                   10                  15
Leu Ser Arg Ser Ile Phe Arg Lys Phe Leu Leu Met Leu Cys Ser Leu
            20                  25                  30
Leu Thr Ser Leu Tyr Val Phe Tyr Cys Leu Ala Glu Arg Cys Gln Thr
        35                  40                  45
Leu Ser Gly Pro Val Val Gly Leu Ser Gly Gly Glu Glu Ala Gly
    50                  55                  60
Ala Pro Gly Gly Val Leu Ala Gly Pro Arg Glu Leu Ala Val
65                  70                  75                  80
Trp Pro Ala Ala Ala Gln Arg Lys Arg Leu Leu Gln Leu Pro Gln Trp
                85                  90                  95
Arg Arg Arg Arg Pro Pro Ala Pro Arg Asp Asp Gly Glu Glu Ala Ala
                100                 105                 110
Trp Glu Glu Glu Ser Pro Gly Leu Ser Gly Gly Pro Gly Gly Ser Gly
            115                 120                 125
Ala Gly Ser Thr Val Ala Glu Ala Pro Pro Gly Thr Leu Ala Leu Leu
        130                 135                 140
Leu Asp Glu Gly Ser Lys Gln Leu Pro Gln Ala Ile Ile Gly Val
145                 150                 155                 160
Lys Lys Gly Gly Thr Arg Ala Leu Leu Glu Phe Leu Arg Val His Pro
                165                 170                 175
Asp Val Arg Ala Val Gly Ala Glu Pro His Phe Phe Asp Arg Ser Tyr
                180                 185                 190
Asp Lys Gly Leu Ala Trp Tyr Arg Asp Leu Met Pro Arg Thr Leu Asp
            195                 200                 205
Gly Gln Ile Thr Met Glu Lys Thr Pro Ser Tyr Phe Val Thr Arg Glu
        210                 215                 220
Ala Pro Ala Arg Ile Ser Ala Met Ser Lys Asp Thr Lys Leu Ile Val
225                 230                 235                 240
Val Val Arg Asp Pro Val Thr Arg Ala Ile Ser Asp Tyr Thr Gln Thr
                245                 250                 255
Leu Ser Lys Arg Pro Asp Ile Pro Thr Phe Glu Ser Leu Thr Phe Lys
            260                 265                 270
Asn Arg Thr Ala Gly Leu Ile Asp Thr Ser Trp Ser Ala Ile Gln Ile
        275                 280                 285
Gly Ile Tyr Ala Lys His Leu Glu His Trp Leu Arg His Phe Pro Ile
    290                 295                 300
Arg Gln Met Leu Phe Val Ser Gly Glu Arg Leu Ile Ser Asp Pro Ala
305                 310                 315                 320
Gly Glu Leu Gly Arg Val Gln Asp Phe Leu Gly Leu Lys Arg Ile Ile
                325                 330                 335
Thr Asp Lys His Phe Tyr Phe Asn Lys Thr Lys Gly Phe Pro Cys Leu
            340                 345                 350
Lys Lys Ala Glu Gly Ser Ser Arg Pro His Cys Leu Gly Lys Thr Lys
        355                 360                 365
Gly Arg Thr His Pro Glu Ile Asp Arg Glu Val Val Arg Arg Leu Arg
    370                 375                 380
Glu Phe Tyr Arg Pro Phe Asn Leu Lys Phe Tyr Gln Met Thr Gly His
385                 390                 395                 400
Asp Phe Gly Trp Asp Gly
                405
```

<210> SEQ ID NO 5
<211> LENGTH: 390
<212> TYPE: PRT
<213> ORGANISM: Homo sapiens

<400> SEQUENCE: 5

```
Met Gly Gln Arg Leu Ser Gly Gly Arg Ser Cys Leu Asp Val Pro Gly
1               5                   10                  15

Arg Leu Leu Pro Gln Pro Pro Pro Pro Pro Val Arg Arg Lys
            20                  25                  30

Leu Ala Leu Leu Phe Ala Met Leu Cys Val Trp Leu Tyr Met Phe Leu
        35                  40                  45

Tyr Ser Cys Ala Gly Ser Cys Ala Ala Pro Gly Leu Leu Leu Leu
    50                  55                  60

Gly Ser Gly Ser Arg Ala Ala His Asp Pro Pro Ala Leu Ala Thr Ala
65                  70                  75                  80

Pro Asp Gly Thr Pro Pro Arg Leu Pro Phe Arg Ala Pro Pro Ala Thr
                85                  90                  95

Pro Leu Ala Ser Gly Lys Glu Met Ala Glu Gly Ala Ala Ser Pro Glu
            100                 105                 110

Glu Gln Ser Pro Glu Val Pro Asp Ser Pro Ser Pro Ile Ser Ser Phe
        115                 120                 125

Phe Ser Gly Ser Gly Ser Lys Gln Leu Pro Gln Ala Ile Ile Ile Gly
    130                 135                 140

Val Lys Lys Gly Gly Thr Arg Ala Leu Leu Glu Phe Leu Arg Val His
145                 150                 155                 160

Pro Asp Val Arg Ala Val Gly Ala Glu Pro His Phe Phe Asp Arg Ser
                165                 170                 175

Tyr Asp Lys Gly Leu Ala Trp Tyr Arg Asp Leu Met Pro Arg Thr Leu
            180                 185                 190

Asp Gly Gln Ile Thr Met Glu Lys Thr Pro Ser Tyr Phe Val Thr Arg
        195                 200                 205

Glu Ala Pro Ala Arg Ile Ser Ala Met Ser Lys Asp Thr Lys Leu Ile
    210                 215                 220

Val Val Val Arg Asp Pro Val Thr Arg Ala Ile Ser Asp Tyr Thr Gln
225                 230                 235                 240

Thr Leu Ser Lys Arg Pro Asp Ile Pro Thr Phe Glu Ser Leu Thr Phe
                245                 250                 255

Lys Asn Arg Thr Ala Gly Leu Ile Asp Thr Ser Trp Ser Ala Ile Gln
            260                 265                 270

Ile Gly Ile Tyr Ala Lys His Leu Glu His Trp Leu Arg His Phe Pro
        275                 280                 285

Ile Arg Gln Met Leu Phe Val Ser Gly Glu Arg Leu Ile Ser Asp Pro
    290                 295                 300

Ala Gly Glu Leu Gly Arg Val Gln Asp Phe Leu Gly Leu Lys Arg Ile
305                 310                 315                 320

Ile Thr Asp Lys His Phe Tyr Phe Asn Lys Thr Lys Gly Phe Pro Cys
                325                 330                 335

Leu Lys Lys Ala Glu Gly Ser Ser Arg Pro His Cys Leu Gly Lys Thr
            340                 345                 350

Lys Gly Arg Thr His Pro Glu Ile Asp Arg Glu Val Val Arg Arg Leu
        355                 360                 365

Arg Glu Phe Tyr Arg Pro Phe Asn Leu Lys Phe Tyr Gln Met Thr Gly
```

-continued

```
               370                 375                 380
His Asp Phe Gly Trp Asp
385                 390

<210> SEQ ID NO 6
<211> LENGTH: 23
<212> TYPE: DNA
<213> ORGANISM: Artificial
<220> FEATURE:
<223> OTHER INFORMATION: 5'-primer for exon 1 of human 3-OST-5

<400> SEQUENCE: 6
ggagggccat gctattcaaa cag                                         23

<210> SEQ ID NO 7
<211> LENGTH: 21
<212> TYPE: DNA
<213> ORGANISM: Artificial
<220> FEATURE:
<223> OTHER INFORMATION: 3'-primer for exon 2 of human 3-OST-5

<400> SEQUENCE: 7
ttagggccag ttcaatgtcc t                                           21

<210> SEQ ID NO 8
<211> LENGTH: 27
<212> TYPE: DNA
<213> ORGANISM: Artificial
<220> FEATURE:
<223> OTHER INFORMATION: 5'-primer for amplification of human 3-OST-5 in
      pGEM-T-3OST5

<400> SEQUENCE: 8
tcaaagcttg ccaccatgct attcaaa                                     27

<210> SEQ ID NO 9
<211> LENGTH: 27
<212> TYPE: DNA
<213> ORGANISM: Artificial
<220> FEATURE:
<223> OTHER INFORMATION: 3'-primer for amplification of human 3-OST-5 in
      pGEM-T-3OST5

<400> SEQUENCE: 9
tctagattag ggccagttca atgtcct                                     27

<210> SEQ ID NO 10
<211> LENGTH: 343
<212> TYPE: PRT
<213> ORGANISM: Artificial
<220> FEATURE:
<223> OTHER INFORMATION: C-terminal portion of human 3-OST-5 linked to
      honeybee melittin signal sequence for incorporation in baculovirus
      expression plasmid

<400> SEQUENCE: 10

Met Lys Phe Leu Val Asn Val Ala Leu Val Phe Met Val Val Tyr Ile
1               5                   10                  15

Ser Tyr Ile Tyr Ala Asp Arg Trp Ile Pro Arg Val Gly Ser Leu Asp
                20                  25                  30

Arg Leu Gln Pro Ile Cys Pro Ile Glu Gly Arg Leu Gly Gly Ala Arg
            35                  40                  45

Thr Gln Ala Glu Phe Pro Leu Arg Ala Leu Gln Phe Lys Arg Gly Leu
    50                  55                  60
```

Leu His Glu Phe Arg Lys Gly Asn Ala Ser Lys Glu Gln Val Arg Leu
 65                  70                  75                  80

His Asp Leu Val Gln Gln Leu Pro Lys Ala Ile Ile Ile Gly Val Arg
                 85                  90                  95

Lys Gly Gly Thr Arg Ala Leu Leu Glu Met Leu Asn Leu His Pro Ala
            100                 105                 110

Val Val Lys Ala Ser Gln Glu Ile His Phe Phe Asp Asn Asp Glu Asn
        115                 120                 125

Tyr Gly Lys Gly Ile Glu Trp Tyr Arg Lys Lys Met Pro Phe Ser Tyr
    130                 135                 140

Pro Gln Gln Ile Thr Ile Glu Lys Ser Pro Ala Tyr Phe Ile Thr Glu
145                 150                 155                 160

Glu Val Pro Glu Arg Ile Tyr Lys Met Asn Ser Ser Ile Lys Leu Leu
                165                 170                 175

Ile Ile Val Arg Glu Pro Thr Thr Arg Ala Ile Ser Asp Tyr Thr Gln
            180                 185                 190

Val Leu Glu Gly Lys Glu Arg Lys Asn Lys Thr Tyr Tyr Lys Phe Glu
        195                 200                 205

Lys Leu Ala Ile Asp Pro Asn Thr Cys Glu Val Asn Thr Lys Tyr Lys
    210                 215                 220

Ala Val Arg Thr Ser Ile Tyr Thr Lys His Leu Glu Arg Trp Leu Lys
225                 230                 235                 240

Tyr Phe Pro Ile Glu Gln Phe His Val Val Asp Gly Asp Arg Leu Ile
                245                 250                 255

Thr Glu Pro Leu Pro Glu Leu Gln Leu Val Glu Lys Phe Leu Asn Leu
            260                 265                 270

Pro Pro Arg Ile Ser Gln Tyr Asn Leu Tyr Phe Asn Ala Thr Arg Gly
        275                 280                 285

Phe Tyr Cys Leu Arg Phe Asn Ile Ile Phe Asn Lys Cys Leu Ala Gly
    290                 295                 300

Ser Lys Gly Arg Ile His Pro Glu Val Asp Pro Ser Val Ile Thr Lys
305                 310                 315                 320

Leu Arg Lys Phe Phe His Pro Phe Asn Gln Lys Phe Tyr Gln Ile Thr
                325                 330                 335

Gly Arg Thr Leu Asn Trp Pro
            340

<210> SEQ ID NO 11
<211> LENGTH: 33
<212> TYPE: DNA
<213> ORGANISM: Artificial
<220> FEATURE:
<223> OTHER INFORMATION: 5' primer for amplification by PCR of
      N-terminal portion of human 3-OST-5

<400> SEQUENCE: 11
aatttggatc cccagagttg ggagcttgga tag                              33

<210> SEQ ID NO 12
<211> LENGTH: 25
<212> TYPE: DNA
<213> ORGANISM: Artificial
<220> FEATURE:

```
<223> OTHER INFORMATION: 3' primer for amplification by PCR of
      N-terminal portion of human 3-OST-5

<400> SEQUENCE: 12
aacaaaactt attacaagtt tgaga                                              25
```

PURIFIED AND ISOLATED HEPARAN SULFATE 3-O-SULFOTRANSFERASE ISOFORM 5 NUCLEIC ACIDS AND POLYPEPTIDES AND THERAPEUTIC AND SCREENING METHODS USING SAME

CROSS REFERENCE TO RELATED APPLICATIONS

This application is a 371 of PCT/US03/21094 filed on Jul. 7, 2003, which claims priority to U.S. Provisional Application Ser. No. 60/394,199, filed Jul. 5, 2002, herein incorporated by reference in its entirety.

GRANT STATEMENT

This work was supported by National Institutes of Health grants R01 AI50050-01 and 053836. Thus, the U.S. Government has certain rights in the invention.

TECHNICAL FIELD

The presently disclosed subject matter relates generally to isolated and purified proteins and nucleic acids. More particularly, the presently disclosed subject matter relates to isolated and purified heparan sulfate 3-O-sulfotransferase polypeptides and isolated and purified nucleic acids encoding the same.

TABLE 1

Abbreviations

| | |
|---|---|
| 3-OST | HS D-glucosaminyl-3-O-sulfotransferase |
| 3-OST-1 | HS D-glucosaminyl-3-O-sulfotransferase isoform 1 |
| 3-OST-3 | HS D-glucosaminyl-3-O-sulfotransferase isoform 3 |
| 3-OST-5 | HS D-glucosaminyl-3-O-sulfotransferase isoform 5 |
| AnMan | 2,5-anhydromannitol |
| AnMan3S | 2,5-anhydromannitol 3-O-sulfate |
| AnMan6S | 2,5-anhydromannitol 6-O-sulfate |
| AnMan3S6S | 2,5-anhydromannitol 3,6-O-disulfate |
| AT | antithrombin |
| BAC | bacterial artificial chromosome |
| BSA | bovine serum albumin |
| CDR | complementarity determining region |
| CHAPS | 3-[(3-cholamidopropyl)diethylammonio]-1-propane sulfonate |
| CHO | Chinese hamster ovary |
| ConA | concanavalin A |
| DEAE | diethylaminoethyl |
| gD | herpes envelope glycoprotein D |
| HAT | cell culture media comprising hypoxanthine, aminopterin, and thymidine |
| HSV-1 | herpes simplex virus, type 1 |
| HS(s) | heparan sulfate(s) |
| $HS^{act}$ | anticoagulant-active or antithrombin-binding HS |
| $HS^{inact}$ | non-antithrombin-binding HS |
| IdoUA2S | L-iduronic acid 2-O-sulfate |
| KLH | keyhole limpet hemocyanin |
| MALDI-MS/MS | matrix-assisted laser desorption/ionization mass spectrometry |
| MES | 2-(N-morphilino)ethanesulfonic acid |
| MOPS | 4-[N-morpholino]propanesulfonic acid |
| NCBI | National Center for Biotechnology Information |
| ORF | open reading frame |
| PAPS | 3'-phosphoadenosine 5'-phosphosulfate |
| PBS | phosphate-buffered saline |
| PCR | polymerase chain reaction |
| Q-TOF | electrospray ionization MS/MS |
| RACE | rapid amplification of cDNA ends |
| RPIP-HPLC | reverse-phase ion-pairing HPLC |
| RT-PCR | reverse transcriptase polymerase chain reaction |
| SV40 | simian virus 40 |
| TM | transmembrane domain |
| X-gal | 5-bromo-4-chloro-3-indolyl-β-D-galactopyranoside |

BACKGROUND ART

Heparan sulfates (HSs) are highly sulfated polysaccharides, present on the surface of mammalian cells and in the extracellular matrix in large quantities. HSs play critical roles in a variety of important biological processes, including assisting viral infection, regulating blood coagulation and embryonic development, suppressing tumor growth, and controlling the eating behavior of mice by interacting with specific regulatory proteins (Liu, J., and Thorp, S. C. (2002) *Med. Res. Rev.* 22:1-25; Rosenberg, R. D., et al., (1997) *J. Clin. Invest.* 99:2062-2070; Bernfield, M., et al., (1999) *Annu. Rev. Biochem.* 68:729-777; Alexander, C. M., et al., (2000) *Nat. Genet* 25:329-332; Reizes, O., et al., (2001) *Cell* 106:105-116). HS polysaccharides carry negative charges under physiological pH, and the disaccharide repeating units include 1→4-linked sulfated glucosamine and uronic acid. The unique sequences determine to which specific proteins HSs bind, thereby regulating biological processes.

The biosynthesis of HS occurs in the Golgi apparatus. It is initially synthesized as a copolymer of glucuronic acid and N-acetylated glucosamine by D-glucuronyl and N-acetyl-D-glucosaminyltransferase, followed by various modifications (Lindahl, U., et al., (1998) *J. Biol. Chem.* 273:24979-24982).

These modifications include N-deacetylation and N-sulfation of glucosamine, $C_5$ epimerization of glucuronic acid to form iduronic acid residues, 2-O-sulfation of iduronic and glucuronic acid, as well as 6-O-sulfation and 3-O-sulfation of glucosamine. Several enzymes that are responsible for the biosynthesis of HS have been cloned and characterized (Esko, J. D., and Lindahl, U. (2001) *J. Clin. Invest.* 108:169-173). These enzymes have become essential tools for investigating the relationship between the structures and functions of HS.

What is still unknown is the detailed mechanism for regulating the biosynthesis of HS with a defined saccharide sequence. A recent report (Liu, J., et al., (1999) *J. Biol. Chem.* 274:5185-5192) suggests that the expression levels of various HS biosynthetic enzyme isoforms contribute to the synthesis of specific saccharide sequences in specific tissues. HS N-deacetylase/N-sulfotransferase, 3-O-sulfotransferase, and 6-O-sulfotransferase are present in multiple isoforms. Each isoform is believed to recognize a saccharide sequence around the modification site in order to generate a specific sulfated saccharide sequence (Liu, J., et al., (1999) *J. Biol. Chem.* 274:5185-5192 ; Aikawa, J.-I., et al., (2001) *J. Biol. Chem.* 276:5876-5882; Habuchi, H., et al., (2000) *J. Biol. Chem.* 275:2859-2868). For instance, HS D-glucosaminyl3-O-sulfotransferase (3-OST) isoforms generate 3-O-sulfated glucosamine residues that are linked to different sulfated uronic acid residues. 3-OST isoform 1 (3-OST-1) transfers sulfate to the 3-OH position of an N-sulfated glucosamine residue that is linked to a glucuronic acid residue at the nonreducing end (GlcUA—GlcNS±6S). However, 3-OST isoform 3 (3-OST-3) transfers sulfate to the 3-OH position of an N-unsubstituted glucosamine residue that is linked to a 2-O-sulfated iduronic acid at the nonreducing end (IdoUA2S—$GlcNH_2$±6S) (Liu, J., et al., (1999) *J. Biol. Chem.* 274:38155-38162). The difference in the substrate specificity of 3-OSTs results in distinct biological functions. For example, the HS modified by 3-OST-1 binds to antithrombin (AT) and possesses anticoagulant activity (Liu, J., et al., (1996) *J. Biol. Chem.* 271:27072-27082). However, the HS modified by 3-OST-3 (3-OST-3A and 3-OST-3B) binds to glycoprotein D (gD) of herpes simplex virus, type 1, (HSV-1) thus mediating viral entry (Shukla, D., et al., (1999) *Cell* 99:13-22).

The HS— and heparin-regulated anticoagulation mechanisms have been studied extensively. It is now known that HS and heparin interact with AT, a serine protease inhibitor, to inhibit the activities of thrombin and factor Xa in the blood coagulation cascade (Rosenberg, R. D., et al., (1997) *J. Clin. Invest.* 99:2062-2070). Anticoagulant-active HS ($HS^{act}$) and heparin contain one or multiple AT-binding sites per polysaccharide chain. This binding site contains a specific pentasaccharide sequence with a structure of —GlcNS(or Ac)6S—GlcUA—GlcNS3S(±6S)—IdoUA2S—GlcNS6S—. The 3-O-sulfation of glucosamine for generating GlcNS3S(±6S) residue, which is carried out by 3-OST-1 (EC 2.8.2.23), is the critical modification for the synthesis of $HS^{act}$ (Liu, J., et al., (1996) *J. Biol. Chem.* 271:27072-27082; Shworak, N. W., et al., (1997) *J. Biol. Chem.* 272:28008-28019).

Cell surface HS also assists HSV-1 infection (WuDunn, D., and Spear, P. G. (1989) *J. Virol.* 63:52-58). A recent report (Shukla, D., et al., (1999) *Cell* 99:13-22) suggests that a specific 3-O-sulfated HS is involved in assisting HSV-1 entry. The 3-O-sulfated HS is generated by 3-OST-3 but not by 3-OST-1. In addition, the 3-O-sulfated HS provides binding sites for HSV-1 envelope glycoprotein D, which is a key viral protein involved in the entry of HSV-1 (Shukla, D., et al., (1999) *Cell* 99:13-22). Because 3-OST-3-modified HS is rarely found in HS from natural sources, the study suggests that HSV-1 recognizes a unique saccharide structure. Indeed, the result from the structural characterization of a gD-binding octasaccharide revealed that the octasaccharide possesses a specific saccharide sequence (Liu, J., et al., (2002) *J. Biol. Chem.* 277:33456-33467). In addition, the binding affinity of the 3-O-sulfated HS for gD is about 2 μM (Shukla, D., et al., *Cell* 99:13-22). This affinity is similar to that reported for the binding of gD to the protein receptors, suggesting that HSV-1 utilizes both protein and HS cell surface receptors to infect target cells (Willis, S. H., et al., (1998) *J. Virol.* 72:5938-5947; Krummenacher, C., et al., (1999) *J. Virol.* 73:8127-8137). It is believed that the interaction between gD and the 3-O-sulfated HS or the protein entry receptors somehow triggers the fusion between the virus and the cell in the presence of other viral envelope proteins, including gB, gH, and gL (Shukla, D., and Spear, P. G. (2001) *J. Clin. Invest.* 108:503-510). A study of the co-crystal structure of gD and herpes entry receptor HveA suggests that the binding of HveA to gD induces conformational changes in gD (Carfi, A., et al., (2001) *Mol. Cell* 8:169-179).

Therefore, a need persists for additional tools for both understanding the mechanism for the biosynthesis of the biologically active HS and for investigating the relationship between the saccharide sequences and the biological functions of HS. This and other needs are addressed by the present disclosure.

SUMMARY

Disclosed is an isolated and purified polynucleotide encoding HS D-glucosaminyl-3-O-sulfotransferase isoform 5 (3-OST-5), and a purified 3-OST-5 polypeptide, and the characterization of the role played by 3-OST-5 polypeptide in generating 3-O-sulfated glucosamine residues that are linked to sulfated uronic acid residues. In one embodiment, disclosed is a recombinant polypeptide that comprises a mammalian 3-OST-5 polypeptide, in a particular embodiment, a human 3-OST-5 polypeptide. Optionally, a polypeptide of the present invention comprises a nucleotide or amino acid sequence selected from the sequences of SEQ ID NOs 1 and 2, respectively.

One embodiment described herein comprises an isolated and purified biologically active 3-OST-5 polypeptide. Optionally, the polypeptide comprises a mammalian 3-OST-5 polypeptide, e.g., the isolated and purified, biologically active 3-OST-5 polypeptide can comprises a human polypeptide encoded by a nucleic acid sequence as set forth in SEQ ID NO 1, a polypeptide encoded by a nucleic acid sequence having greater than 90% sequence identity to SEQ ID NO 1, a polypeptide having an amino acid sequence as set forth in SEQ ID NO 2, a polypeptide which is a biological equivalent of the polypeptide set forth in SEQ ID NO 2, a polypeptide which is immunologically cross-reactive with an antibody which is immunoreactive with a polypeptide comprising part or all of the amino acids of SEQ ID NO 2, or a polypeptide encoded by a nucleic acid molecule capable of hybridizing under stringent conditions to a nucleic acid molecule comprising the nucleotides of SEQ ID NO 1, or a complement thereof.

Another embodiment described herein provides an isolated and purified polynucleotide that encodes a biologically active 3-OST-5 polypeptide. In a one embodiment, a polynucleotide of the embodiment comprises a DNA molecule from a mammal. In another embodiment, a polynucleotide of the embodiment described herein encodes a polypeptide comprising an amino acid residue sequence of SEQ ID NO 2. In yet another embodiment, an isolated and purified polynucleotide of the embodiment described herein comprises a nucleic acid molecule having a nucleic acid sequence with greater than 90% sequence identity to SEQ ID NO 1. In still another embodiment, an isolated and purified polynucleotide of the embodiment comprises a nucleotide sequence of SEQ ID NO 1.

Another embodiment described herein provides a transgenic non-human animal having incorporated into its genome a xenogeneic nucleic acid molecule encoding a biologically active 3-OST-5 polypeptide. The nucleic acid molecule is present in the genome in a copy number effective to confer expression in the animal of the 3-OST-5 polypeptide.

Yet another embodiment described herein provides a method of producing an antibody immunoreactive with a 3-OST-5 polypeptide. The method comprises transfecting a recombinant host cell with a nucleic acid molecule encoding a 3-OST-5 polypeptide. The host cell is cultured under conditions sufficient for expression of the polypeptide. The polypeptide is recovered and an antibody prepared to the polypeptide. The host cell can be transfected with a polynucleotide of SEQ ID NO 1. Optionally, the embodiment described herein provides an antibody prepared according to the process described above. Also contemplated by the embodiment described herein is the use of homologues or biologically equivalent 3-OST-5 polynucleotides and polypeptides found in other mammals to produce antibodies. The embodiment further includes methods of detecting a 3-OST-5 polypeptide using an antibody prepared as described above.

In an alternative embodiment described herein, a method is provided for detecting a nucleic acid molecule that encodes a 3-OST-5 polypeptide in a biological sample containing nucleic acid material. The method comprises hybridizing a nucleic acid molecule having greater than 90% sequence identity to SEQ ID NO 1 under stringent hybridization conditions to the nucleic acid material of the biological sample, thereby forming a hybridization duplex and then detecting the hybridization duplex.

In another aspect, an embodiment described herein provides an assay or assay kit for detecting the presence of a 3-OST-5 polypeptide in a biological sample, where the kit comprises a first antibody capable of immunoreacting with a biologically active 3-OST-5 polypeptide. Optionally, the first antibody is present in an amount sufficient to perform at least one assay. An assay kit can further comprise a second antibody that immunoreacts with the first antibody. The antibodies used in an assay kit can be monoclonal antibodies. The first antibody can be affixed to a solid support. The first and second antibodies can comprise an indicator, and, optionally, the indicator is a radioactive label, a fluorescent label or an enzyme.

In an alternative aspect, another embodiment described herein provides an assay or assay kit for detecting the presence, in biological samples, of a 3-OST-5 polypeptide, the kits comprising a polynucleotide identical or complementary to a segment of at least 10 contiguous nucleotide bases of a polynucleotide that encodes a 3-OST-5 polypeptide.

Another embodiment described herein provides an assay or assay kit for detecting the presence, in a biological sample, of an antibody immunoreactive with a 3-OST-5 polypeptide, the kit comprising a first container containing a biologically active 3-OST-5 polypeptide that immunoreacts with the antibody, with the polypeptide present in an amount sufficient to perform at least one assay.

Still another embodiment described herein provides a method of screening candidate substances for an ability to modulate 3-OST-5 biological activity. One method comprises establishing test samples comprising a 3-OST-5 polypeptide, administering a candidate substance to the test samples, and measuring the interaction, effect, or combination thereof, of the candidate substance on the test sample to thereby determine the ability of the candidate substance to modulate 3-OST-5 biological activity. Optionally, the candidate substance is a candidate polypeptide, and the method further comprises purifying and isolating a gene encoding the candidate polypeptide.

Still further embodiments described herein pertain to therapeutic methods and compositions based upon the modulation of the biological activity of 3-OST-5 via polynucleotides and polypeptides as described herein. Such therapeutic methods and compositions include gene therapy approaches using an isolated and purified polynucleotide as described herein.

Yet even further embodiments described herein provide methods for modulating transfer of sulfate to the 3-OH position of a glucosamine residue of heparan sulfate in a vertebrate subject. The methods comprise introducing to a target tissue producing heparan sulfate in the vertebrate subject a construct comprising a nucleic acid sequence encoding a 3-OST-5 gene product operatively linked to a promoter, wherein production of the 3-OST-5 gene product in the target tissue results in modulation of transfer of sulfate to the 3-OH position of a glucosamine residue of heparan sulfate.

In another embodiment described herein, a method is provided for modulating production of 3-O-sulfated heparan sulfate in a vertebrate subject. The method is comprised of introducing to a target tissue comprising cells producing heparan sulfate in the vertebrate subject a construct comprising a nucleic acid sequence encoding a 3-OST-5 gene product operatively linked to a promoter, wherein production of the 3-OST-5 gene product in the target tissue results in modulation of production of 3-O-sulfated heparan sulfate. Optionally, the 3-O-sulfated heparan sulfate is an anticoagulant-active heparan sulfate. Also optionally, the 3-O-sulfated heparan sulfate is an antithrombin-binding heparan sulfate. Alternatively, the 3-O-sulfated heparan sulfate is an entry receptor for HSV-1. Alternatively still, the 3-O-sulfated heparan sulfate is both an anticoagulant-active heparan sulfate and an entry receptor for HSV-1. In other embodiments, the 3-O-sulfated heparan sulfate comprises a disaccharide selected from the group consisting of L-iduronic acid 2-O-sulfate-2,5,-anhydromannitol 3-O-sulfate; D-glucuronic acid-2,5,-anhydromannitol 3,6-O-sulfate; L-iduronic acid 2-O-sulfate-2,5,-anhydromannitol 3,6-O-sulfate; L-iduronic acid-2,5-anhydromannitol 3,6-O-sulfate; L-iduronic acid-2,5-anhydromannitol 3-O-sulfate; D-glucuronic acid-2,5-anhydromannitol 3-O-sulfate; $\Delta^{4,5}$-uronic acid-glucosamine N,3-disulfate; and $\Delta^{4,5}$-uronic acid-glucosamine N-sulfate-iduronic acid 2-sulfate-glucosamine 3,6-disulfate.

Another embodiment provided herein is a method for increasing the efficacy of treating a disorder using a virus vector for delivering therapeutic nucleic acid molecules to the cells of a subject. The method comprises administering to the subject a construct comprising a nucleic acid sequence encoding a 3-OST-5 gene product operatively linked to a promoter prior to administration of the virus vector, wherein production of the 3-OST-5 gene product in the cells results in increased expression of 3-O-sulfated heparan sulfate, and wherein the 3-O-sulfated heparan sulfate is an entry receptor for the virus vector.

The foregoing aspects and embodiments have broad utility given the biological significance of the 3-O-sulfotransferase proteins. By way of example, the foregoing aspects and embodiments are useful in the preparation of screening assays and assay kits that are used to identify compounds that affect or modulate HS sulfation biological activity, or that are used to detect the presence of the proteins and nucleic acids of this invention in biological samples.

Accordingly, it is an object of the present invention to provide a novel and isolated and purified polynucleotide encoding 3-OST-5, and a purified 3-OST-5 polypeptide, and screening and therapeutic methods involving the same. This and other objects are achieved in whole or in part by the present disclosure.

Other aspects and objects will become evident as the description proceeds, when taken in connection with the accompanying Drawings and Examples as best described herein below.

BRIEF DESCRIPTION OF THE DRAWINGS

FIG. 1 is an alignment chart of the nucleotide and deduced amino acid sequences of 3-OST-5 (GENBANK™ accession AF503292) (SEQ ID NOs 1 and 2, respectively). The single predicted membrane spanning domain and four potential N-linked glycosylation sites are indicated by the doubled underline and by the underlines with a ● below the glycosylated Asn, respectively.

FIG. 2 is a multiple amino acid sequence alignment of human 3-OST-5 (SEQ ID NO 2) with human 3-OST-1, 3-OST-3A, and 3-OST-3B (SEQ ID NOs 3, 4 and 5, respectively). The alignment was performed by using the program BIOEDIT™ (available as freeware from Tom Hall, Department of Microbiolgy, North Carolina State University, Raleigh, N.C., United States of America). Introduced gaps are shown as hyphens, and aligned amino acids are boxed and shaded with black for identical residuals and dark gray for similar residuals. 5'-PSB represents the putative domain that binds to 5'-phosphate of 3'-phosphoadenosine 5'-phosphosulfate (PAPS), and 3'-PSB represents the putative domain that binds to 3'-phosphate of PAPS.

FIGS. 4A and 4B are photomicrographs showing entry of HSV-1 into CHO—K1 cells and transfected CHO—K1 cells. CHO—K1 cells were transfected with control plasmid (FIG. 4A) or with pcDNA3.1-3OST5 (FIG. 4B). At 36 hours after transfection, the cells were exposed to KOS—gL86 at 100 plaque-forming units/cell. Six hours later, the cells were washed, fixed, and incubated with 5-bromo-4-chloro-3-indolyl-β-D-galactopyranoside (X-gal) to identify infected cells (dark cells).

FIGS. 5A and 5B are RPIP-HPLC chromatograms of the disaccharide analysis of 3-OST-5-modified non-antithrombin-binding HA (HS$^{inact}$) and HS$^{act}$. HS$^{act}$ was prepared from 3-OST-5-modified HS using an AT-affinity column. HS$^{inact}$ was the fraction that does not bind to AT-affinity column (A). HS$^{act}$ was eluted from the AT-affinity column with 1 M NaCl (B). Both HS$^{inact}$ and HS$^{act}$ were degraded with nitrous acid (pH 1.5) followed by sodium borohydride reduction. The arrows indicate the elution positions of disaccharide standards as described in FIG. 3.

FIG. 7A is an autoradiograph of the Northern analysis of wild type CHO cells and CHO/3-OST-5 cells. Procedures for preparing the Northern blot followed the standard protocol. Approximately 2 µg of mRNA (from wild type CHO and from CHO/3-OST-5) was loaded in denatured agarose gel. The blot was probed by $^{32}$P-labeled 3-OST-5 probe as described by Xia, G., et al., (2002) *J. Biol. Chem.* 277:37912-37919. FIG. 7B is a photograph of agarose gel analysis of the products of reverse transcriptase polymerase chain reaction (RT-PCR) of mRNA. Lanes 1 and 2 represent the analysis of the mRNAs from CHO/3-OST-5 at 26 ng and 52 ng, respectively. Lanes 3 and 4 represent the analysis of mRNAs from wild type CHO cells at 24 and 48 ng, respectively.

FIG. 8A shows the chromatogram of the HS from wild type CHO cells. FIG. 8B panel shows the chromatogram of the HS from CHO/3-OST-5 cells. The arrows indicate the elution positions of the disaccharide standards, where 1 represents IdoUA2S—AnMan3S, 2 represents GlcUA—AnMan3S6S, 3 represents IdoUA2S—AnMan6S, and 4 represents IdoUA2S—AnMan3S6S.

FIG. 9A depicts the elution profile from Heparin-SEPHAROSE™ chromatography. Media from infected cells was loaded onto a Heparin-SEPHAROSE™ column. FIG. 9B depicts the profile from a 3',5'-ADP-agarose column. The solid bars in FIGS. 9A and 9B indicate the fractions that were pooled. The concentrations of proteins were determined by monitoring the absorbance of UV at 280 nm. The activity of 3-OST-5 was monitored by incubating the eluent (10 µl) with unlabeled HS and [$^{35}$S]PAPS to generate [$^{35}$S]HS.

FIGS. 10A and 10B depict the determination of the purity of 3-OST-5 enzyme by SDS-PAGE and mass spectrometry. FIG. 10A depicts the analysis of purified 3-OST-5 (1 µg) by 13% SDS-PAGE stained with Coomassie blue. FIG. 10B depicts the sequence coverage of the Coomassie blue-stained bands (SEQ ID NO 10). Three bands, B1, B2, and B3, were cut from the gel followed by in-gel digestion with trypsin. The products were subjected to MALDI-MS and/or electrospray ionization MS/MS (Q-TOF) analyses. The identified amino acid sequences from B2 and B3 by MALDI-MS are single-underlined. The identified amino sequence from B1 by Q-TOF is double-underlined. The honeybee melittin signal sequence is boxed. The "↓" indicates where the amino acid sequence of 3-OST-5 starts. The potential N-glycosylation sites are in boldface type.

FIGS. 12A and 12B depict PAMN-HPLC chromatograms of Disaccharides 2 and 4 before and after the digestions of α-iduronidase. FIG. 12A shows the elution profile of α-iduronidase-digested Disaccharide 2. FIG. 12B shows the elution profile of α-iduronidase-digested Disaccharide 4. The elution positions of undigested Disaccharides 2 and 4 on PAMN-HPLC are indicated by arrows in FIGS. 12A and 12B, respectively. The actions of α-iduronidase on Disaccharides 2 and 4 are illustrated to the side of FIGS. 12A and 12B, respectively.

FIGS. 13A and 13B depict the elution profile of heparin lyases digested 3-OST-5-modified HS on BIOGEL® P-6 and RPIP-HPLC chromatogram of the disaccharide portion from BIOGEL® P-6. FIG. 13A depicts the profile of heparin lyase-digested HS on BIOGEL® P-6. The elution positions of the disaccharides and tetrasaccharides were determined by co-eluting with $^3$H-labeled standards.

FIGS. 14A and 14B depict HPLC chromatograms of nitrous acid-degraded and $\Delta^{4,5}$-glycuronidase-digested Disaccharide X. FIG. 14A depicts an RPIP-HPLC chromatogram of nitrous acid (pH 1.5)-degraded Disaccharide X. FIG. 14B depicts a PAMN-HPLC chromatogram of $\Delta^{4,5}$-glycuronate-2-sulfatase digested Disaccharide X. The arrows indicate the elution positions of undegraded Disaccharide X. The nitrous acid degradation and Δ4,5-glycuronate-2-sulfatase digestion reactions are illustrated on the sides of FIGS. 14A and 14B, respectively.

FIGS. 15A and 15B depicts PAMN-HPLC chromatograms of tetrasaccharide pool and nitrous acid (pH 4.5)-degraded Tetra-1. FIG. 15A depicts a chromatogram of a tetrasaccharide pool that was obtained from heparin lyases-digested 3-OST-5-modified HS (see FIG. 13A). FIG. 15B depicts a chromatogram of nitrous acid (pH 4.5)-degraded Tetra-1.

SUMMARY OF SEQUENCES IN THE SEQUENCE LISTING

Figure 3:
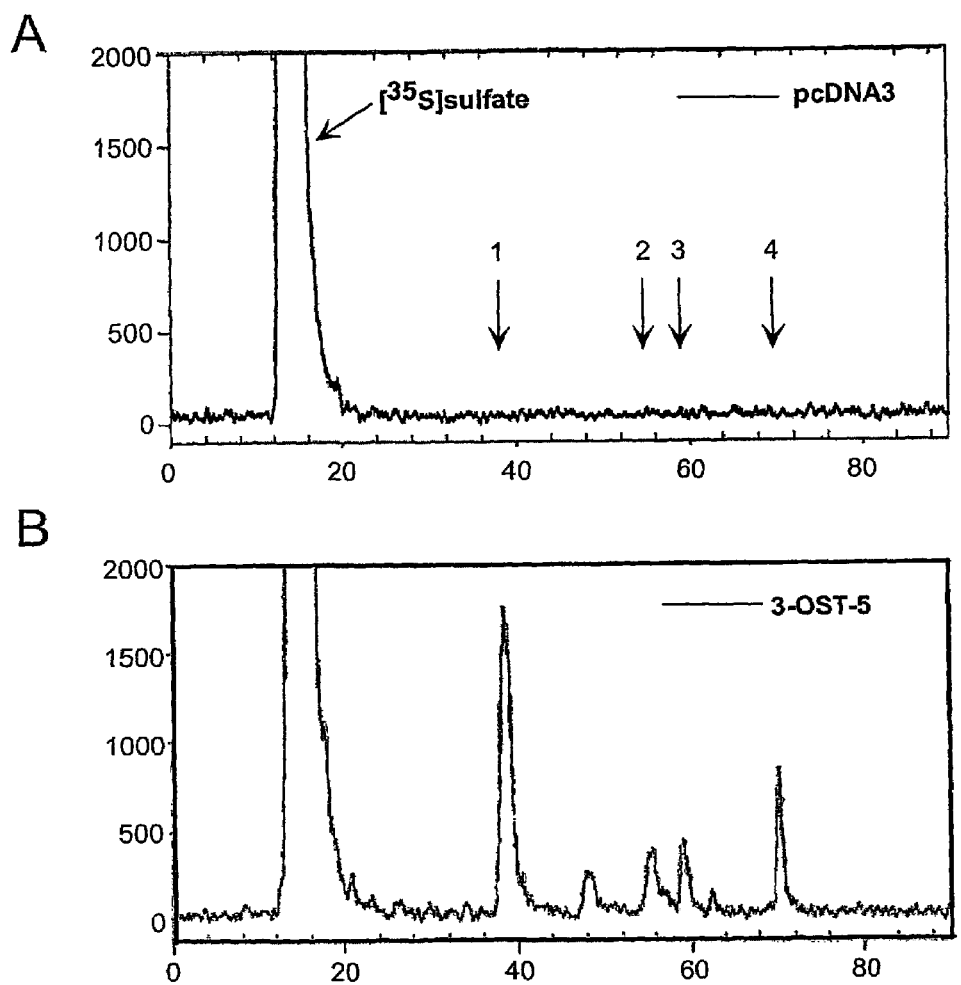
FIGS. 3A and 3B are reverse-phase ion-pairing high performance liquid chromatography (RPIP-HPLC) chromatograms of the disaccharide analysis of 3-OST-5-modified HS. Cell extracts from COS-7 cells transfected with the empty plasmid vector pcDNA 3 (FIG. 3A) or with the plasmid expressing 3-OST-5 (FIG. 3B) were incubated with unlabeled HS and [$^{35}$S]PAPS to prepare the [$^{35}$S]HS. The resultant [$^{35}$S]HS was depolymerized by nitrous acid at pH 1.5 followed by sodium borohydride reduction. The resultant $^{35}$S-labeled disaccharides were resolved on RPIP-HPLC. The elution positions of the disaccharide standards are indicated by arrows, where arrow 1 represents IdoUA2S-AnMan3S; arrow 2 represents GlcUA-AnMan3S6S; arrow 3 represents IdoUA2S—AnMan6S; and arrow 4 represents IdoUA2S-AnMan3S6S.

SEQ ID NO 1 is a nucleotide sequence encoding a human 3-OST-5 polypeptide.

SEQ ID NO 2 is a human polypeptide sequence encoded by the nucleotide sequence of SEQ ID 1.

SEQ ID NO 3 is a human 3-OST-1 polypeptide sequence.

SEQ ID NO 4 is a human 3-OST-3a polypeptide sequence.

SEQ ID NO 5 is a human 3-OST-3b polypeptide sequence.

SEQ ID NO 6 is a 5' DNA primer sequence specific for 3-OST-5 used for amplification of 3-OST-5 from a human placenta cDNA library.

SEQ ID NO 7 is a 3' DNA primer sequence specific for 3-OST-5 used for amplification of 3-OST-5 from a human placenta cDNA library.

SEQ ID NO 8 is a 5' DNA primer sequence specific for 3-OST-5 used for amplification of 3-OST-5 for incorporation into an expression plasmid.

SEQ ID NO 9 is a 3' DNA primer sequence specific for 3-OST-5 used for amplification of 3-OST-5 for incorporation into an expression plasmid.

SEQ ID NO 10 is a fusion polypeptide comprised of an N-terminal honeybee melittin signal sequence linked to a 317 amino acid C-terminal 3-OST-5 polypeptide fragment.

SEQ ID NO 11 is a 5' DNA primer sequence specific for 3-OST-5 used for amplification of a C-terminus 3-OST-5 peptide for incorporation into a baculovirus expression plasmid.

SEQ ID NO 12 is a 3' DNA primer sequence specific for 3-OST-5 used for amplification of a C-terminus 3-OST-5 peptide for incorporation into a baculovirus expression plasmid.

DETAILED DESCRIPTION

Disclosed herein is a novel member of the 3-OST gene family and provides a novel human HS D-glucosaminyl-3-O-sulfotransferase isoform 5 (3-OST-5) (representative embodiments set forth in SEQ ID NOs 1 and 2). In one embodiment, 3-OST-5 has an open reading frame (ORF) found to be 1041 base pairs (bp). The open reading frame is located in two exons that are gapped by a 4.5-kb intron. The open reading frame of 3-OST-5 was amplified from a human placenta cDNA library using specific 5'- and 3'-primers (SEQ ID NOs 6 and 7, respectively) as described in the Examples. Embodiments of the 3-OST-5 cDNA sequence (SEQ ID NO 1) and the amino acid sequence (SEQ ID NO 2) are shown aligned in FIG. 1.

Figure 2:
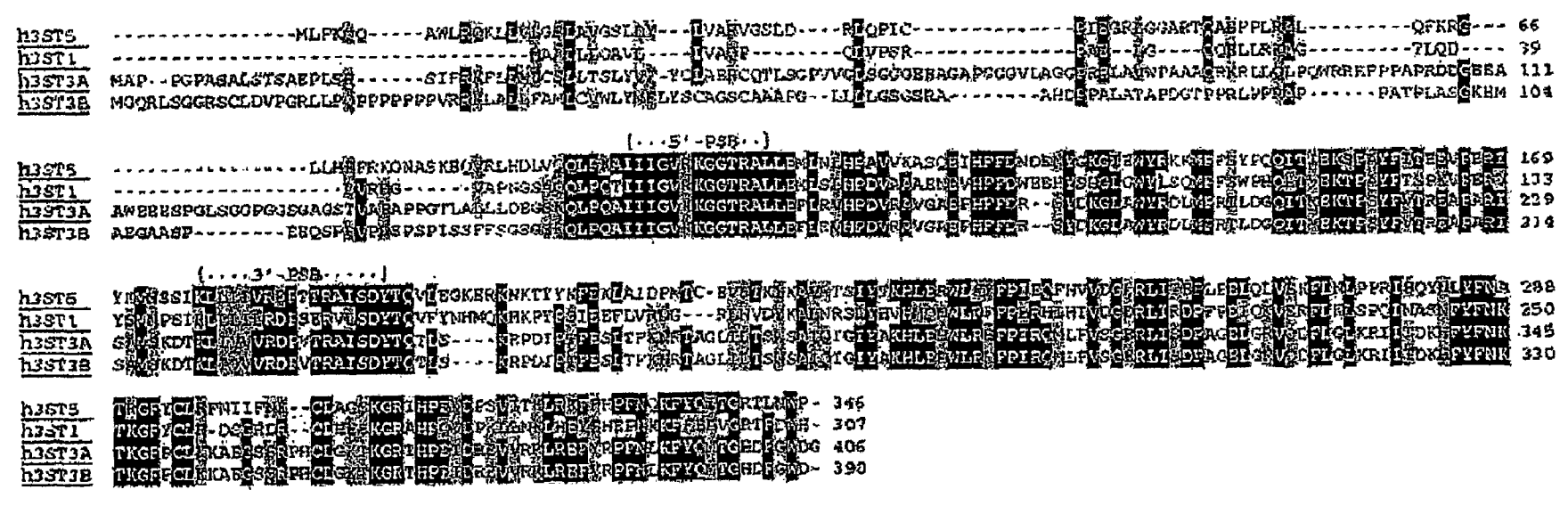

The isolated 3-OST-5 cDNA encodes a peptide of 346 amino acid residues. The peptide sequence indicates a type II membrane-bound protein. The protein has four potential N-glycosylation sites with a predicted molecular mass of 40,407 Da. The amino acid sequence of 3-OST-5 has 71 and 58% homology to 3-OST-1 and 3-OST-3 in the sulfotransferase domains, respectively (FIG. 2). Putative PAPS-binding sites were also found in 3-OST-5 based upon the PAPS-binding consensus sequences (FIG. 2).

A genomic bacterial artificial chromosome (BAC) clone RP11-112L15, which contains the 3-OST-5 gene, was annotated to be mapped on human chromosome 6q22.1. Alignment of the genomic sequence with 3-OST-5 cDNA revealed that exon 1 and exon 2 contain 107 and 934 bp of the open reading frame, respectively. Those domains are found in the previously characterized full-length 3-OST-2 and 3-OST-3, although the full-length 3-OST-1 lacks a transmembrane domain (TM). If an additional sequence were present in the 3-OST-5 coding region, it would likely encode an additional cytosolic domain. It is known that the cytosolic domains of previously characterized 3-OSTs do not contribute to the enzymatic activities.

Amino acid homology search revealed that 3-OST-5 has 58% homology to 3-OST-3 and 72% homology to 3-OST-1, respectively, in the predicted sulfotransferase domain. The data suggest that the amino acid sequence of 3-OST-5 is closer to 3-OST-1. However, no domain in 3-OST-5 that is specifically homologous to 3-OST-1 or to 3-OST-3 has been found, implying that the substrate specificities of 3-OST isoforms are determined by the three-dimensional structures of the enzymes.

3-OST-1 is a secreted protein, as it lacks a TM, whereas 3-OST-5 is a membrane-bound protein with a predicted TM. In support of this conclusion, no 3-OST-5 activity has been detected in the growth media. A recent report (Yabe, T., et al., (2001) *Biochem. J.* 359:235-241) demonstrated that the TM of 3-OSTs had no effect on their substrate specificities. Based upon their results, it can be concluded that the additional TM of 3-OST-5 is unlikely to provide profound effect on the activities in synthesizing HS$^{act}$ and gD-binding HS.

Figure 16:
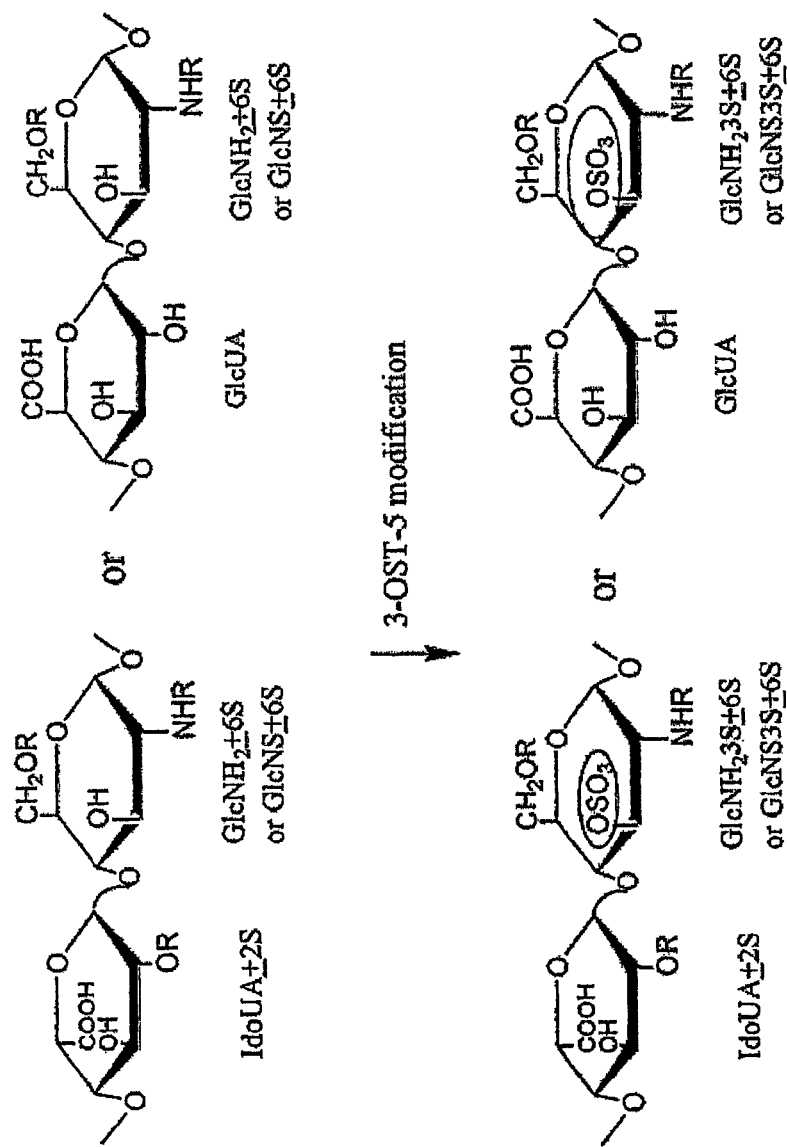
FIG. 16 presents a summary of the substrate specificity of 3-OST-5. 3-OST-5 enzyme sulfates the glucosamine residue that is linked to both iduronic acid or 2-O-sulfated iduronic acid residue at the non-reducing end. In addition, 3-OST-5 sulfates the glucosamine residue that is linked to a non-sulfated glucuronic acid residue. 3-OST-5 sulfates N-unsubstituted or N-sulfated glucosamine residue. R represents hydrogen (—H) or sulfate (—SO$_3$).

The substrate specificity of 3-OST-5 was characterized by determining the identities of the $^{35}$S-labeled disaccharides from low pH nitrous acid-degraded 3-OST-5-modified HS, as described in the Examples. The enzyme generates at least three (see also FIG. 16) 3-O-sulfated disaccharides as follows: IdoUA2S—AnMan3S, GlcUA—AnMan3S6S, and IdoUA2S—AnMan3S6S. Among these disaccharides, IdoUA2S—AnMan3S and IdoUA2S—AnMan3S6S are the characteristic disaccharides of 3-OST-3-modified HS, whereas GlcUA-AnMan3S6S is a characteristic disaccharide of 3-OST-1-modified HS. Thus, 3-OST-5 possesses the novel characteristic of exhibiting the activities of both 3-OST-1 and 3-OST-3. It is known that 3-OST-1 generates HS$^{act}$, whereas 3-OST-3 generates entry receptor for HSV-1. As shown herein, 3-OST-5-modified HS binds to AT and gD. In addition, transfection of the plasmid expressing 3-OST-5 rendered the susceptibility of HSV-1 to wild type CHO cells. Therefore, as disclosed in the data presented herein, 3-OST-5 has both 3-OST-1- and 3-OST-3-activities.

Northern analysis detailed in the Examples demonstrates that 3-OST-5 is predominantly expressed in the human skeletal muscle tissue. A previous report demonstrated that 3-OST-1 and 3-OST-3 (including 3-OST-3A and 3-OST-3B) were widely expressed in numerous human tissues, but low in skeletal muscle. The tissue distribution of 3-OST-5 suggests that 3-OST-5-modified HS may provide a unique biological function in this tissue. It is very interesting to note that a unique subset of HS was identified in human skeletal muscle tissues by a set of antibodies that bind to HS (Jenniskens, G. J., et al., (2000) *J. Neurosci.* 20:4099-4111). While not wishing to be bound by theory, it is believed that the unique subset of HS found in the skeletal muscle tissue is associated with 3-OST-5 modification. This provides a use for gene therapy treatment of diseases utilizing HSV-1 as a vector targeted to muscle tissue.

Clinical manifestations of herpes simplex virus are typically seen in two types of cells as follows: mucosal epithelium with characteristic herpetic lesions, and in a few cases, neuronal cells, causing life-threatening encephalitis. Acute viremia exists but is very rarely seen in infected patients. Based on the current knowledge, it is unlikely that infection of HSV in skeletal muscle has long term pathogenic effects. HSV-1, therefore, can be utilized as a viral vector to deliver genes to human skeletal muscle. For example, a specially engineered HSV-1 was used for Duchenne muscular dystrophy (Akkaraju, G. R., et al., (1999) *J. Gene Med.* 1:280-289). The advantages for using HSV-1 vector include high transduction efficiency and the capability to pack a large gene (Wang, Y., et al., (2000) *Am. J. Physiol.* 278:C619-C626). Given the facts that 3-OST-5-modified HS serves as an entry receptor for HSV-1 and it is expressed in the human skeletal muscle, the 3-OST-5-modified HS can serve as a receptor in skeletal muscle tissues for HSV-1 infection. Thus, 3-OST-5-assisted HSV-1 entry can be used as a gene therapy tool for treating muscular dystrophy.

Thus, disclosed herein are isolated and purified nucleic acids encoding 3-OST-5 polypeptides; isolated and purified 3-OST-5 polypeptides; the characterization of the role played by the 3-OST-5 polypeptide in the targeted 3-O-sulfation of HS glucosamine residues; and to the characterization of downstream processes affected by such modulation.

I. Polypeptides and Nucleic Acids

As used in the following detailed description and in the claims, the term "3-OST-5" includes nucleic acids and polypeptides encoding HS D-glucosaminyl-3-O-sulfotransferase isoform 5. The term "3-OST-5" includes invertebrate homologs; preferably, 3-OST-5 nucleic acids and polypeptides are isolated from eukaryotic sources. "3-OST-5" further includes vertebrate homologs of HS D-glucosaminyl-3-O-sulfotransferase isoform 5, including, but not limited to, mammalian and avian homologs. Representative mammalian homologs of HS D-glucosaminyl-3-O-sulfotransferase isoform 5 include, but are not limited to, human homologs.

The terms "3-OST-5 gene product", "3-OST-5 protein", and "3-OST-5 polypeptide" refer to peptides having amino acid sequences which are substantially identical to native amino acid sequences from the organism of interest and which are biologically active in that they comprise all or a part of the amino acid sequence of a HS D-glucosaminyl-3-O-sulfotransferase isoform 5, or cross-react with antibodies raised against a HS D-glucosaminyl-3-O-sulfotransferase isoform 5 polypeptide, or retain all or some of the biological activity of the native amino acid sequence or protein. Such biological activity can include immunogenicity.

The terms "3-OST-5 gene product", "3-OST-5 protein", and "3-OST-5 polypeptide" also include analogs of HS D-glucosaminyl-3-O-sulfotransferase isoform 5 molecules. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct 3-OST-5 analogs. There is no need for a "3-OST-5 gene product", "3-OST-5 protein", and "3-OST-5 polypeptide" to comprise all or substantially all of the amino acid sequence of a native 3-OST-5 gene product. Shorter or longer sequences are anticipated to be of use in the invention; shorter sequences are herein referred to as "segments." Thus, the terms "3-OST-5 gene product", "3-OST-5 protein", and "3-OST-5 polypeptide" also include fusion or recombinant HS D-glucosaminyl-3-O-sulfotransferase isoform 5 polypeptides and proteins comprising sequences of the present invention. Methods of preparing such proteins are known in the art.

The terms "3-OST-5 gene", "3-OST-5 gene sequence", and "3-OST-5 gene segment" refer to any DNA sequence that is substantially identical to a polynucleotide sequence encoding a HS D-glucosaminyl-3-O-sulfotransferase isoform 5 gene product, protein or polypeptide as defined above, and can also comprise any combination of associated control sequences. The terms also refer to RNA, or antisense sequences, complementary to such DNA sequences. As used herein, the term "DNA segment" refers to a DNA molecule that has been isolated free of total genomic DNA of a particular species. Furthermore, a DNA segment encoding a HS D-glucosaminyl-3-O-sulfotransferase isoform 5 polypeptide refers to a DNA segment that contains 3-OST-5 coding sequences, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

The term "substantially identical", when used to define either a 3-OST-5 gene product or amino acid sequence, or a 3-OST-5 gene or nucleic acid sequence, means that a particular sequence varies from the sequence of a natural 3-OST-5 by one or more deletions, substitutions, or additions, the net effect of which is to retain at least some of biological activity of the natural gene, gene product, or sequence. Such sequences include "mutant" sequences, or sequences in which the biological activity is altered to some degree but retains at least some of the original biological activity.

Alternatively, DNA analog sequences are "substantially identical" to specific DNA sequences disclosed herein if: (a) the DNA analog sequence is derived from coding regions of the natural 3-OST-5 gene; or (b) the DNA analog sequence is capable of hybridization of DNA sequences of (a) under stringent conditions and which encode biologically active 3-OST-5 gene product; or (c) the DNA sequences are degenerate as a result of alternative genetic code to the DNA analog sequences defined in (a) and/or (b). Substantially identical analog proteins will be greater than about 60% identical to the corresponding sequence of the native protein. Sequences having lesser degrees of identity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

Sequence identity or percent similarity of a DNA or peptide sequence can be determined, for example, by comparing sequence information using the GAP computer program, available from the University of Wisconsin Geneticist Computer Group. The GAP program utilizes the alignment method of Needleman et al. (1970) *J Mol Biol* 48:443, as revised by Smith et al. (1981) *Adv Appl Math* 2:482. Briefly, the GAP program defines similarity as the number of aligned symbols (i.e., nucleotides or amino acids) that are similar, divided by the total number of symbols in the shorter of the two sequences. The preferred parameters for the GAP program are the default parameters, which do not impose a penalty for end gaps. See Schwartz et al. (1979) *Nuc Acids Res* 6(2):745-755; Gribskov et al. (1986) *Nuc Acids Res* 14(1): 327-334.

In certain embodiments, the invention concerns the use of 3-OST-5 genes and gene products that include within their respective sequences a sequence that is essentially that of a 3-OST-5 gene, or the corresponding protein. The term "a sequence essentially as that of a 3-OST-5 gene", means that the sequence is substantially identical or substantially similar to a portion of a 3-OST-5 gene and contain a minority of bases or amino acids (whether DNA or protein) which are not identical to those of a 3-OST-5 protein or a 3-OST-5 gene, or which are not a biologically functional equivalent. The term "biologically functional equivalent" is well understood in the art and is further defined in detail herein. Nucleotide sequences are "essentially the same" where they have between about 75% and about 85% or more preferably, between about 86% and about 90%, or more preferably greater than 90%, or more preferably between about 91% and about 95%, or even more preferably, between about 96% and about 99%; of nucleic acid residues which are identical to the nucleotide sequence of a 3-OST-5 gene. Similarly, peptide sequences which have about 80%, or 90%, or preferably from 90-95%, or more preferably greater than 96%, or more preferably 95-98%, or most preferably 99% or greater amino acids which are identical or functionally equivalent or biologically functionally equivalent to the amino acids of a 3-OST-5 polypeptide will be sequences which are "essentially the same".

3-OST-5 gene products and 3-OST-5 encoding nucleic acid sequences, which have functionally equivalent codons, are also covered by the invention. The term "functionally equivalent codon" is used herein to refer to codons that encode the same amino acid, such as the ACG and AGU codons for serine. Thus, when referring to the sequence examples presented in SEQ ID NO 1, applicants contemplate substitution of functionally equivalent codons of Table 2 into the sequence examples of SEQ ID NO 1. Thus, applicants are in possession of amino acid and nucleic acid sequences which include such substitutions but which are not set forth herein in their entirety for convenience.

TABLE 2

Functionally Equivalent Codons

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |

TABLE 2-continued

Functionally Equivalent Codons

| Amino Acids | | | Codons |
|---|---|---|---|
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood by those of skill in the art that amino acid and nucleic acid sequences can include additional residues, such as additional NB or C-terminal amino acids or 5' or 3' nucleic acid sequences, and yet still be essentially as set forth in one of the sequences disclosed herein, so long as the sequence retains biological protein activity where protein expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

The present invention also encompasses the use of nucleotide segments that are complementary to the sequences of the present invention, in one emobodiment, segments that are fully complementary, i.e. complementary for their entire length. Nucleic acid sequences that are "complementary" are those, which are base-paired according to the standard Watson-Crick complementarity rules. As used herein, the term "complementary sequences" means nucleic acid sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

One technique in the art for assessing complementary sequences and/or isolating complementary nucleotide sequences is hybridization. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., typically in excess of about 37° C., and preferably in excess of about 45° C. Stringent salt conditions will ordinarily be less than about 1,000 mM, typically less than about 500 mM, and preferably less than about 200 mM. However, the combination of parameters is much more important than the measure of any single parameter. See e.g., Wethmur & Davidson (1968) *J Mol Bio* 31:349-370. Determining appropriate hybridization conditions to identify and/or isolate sequences containing high levels of homology is well known in the art. See e.g., Sambrook et al. (2001) *Molecular Cloning: A Laboratory Manual*, Third Edition, Cold Spring Harbor Laboratory Press, Cold Spring Harbor, N.Y.

For the purposes of specifying conditions of high stringency, preferred conditions are salt concentration of about 200 mM and temperature of about 45° C. One example of such stringent conditions is hybridization at 4×SSC, at 65° C., followed by a washing in 0.1×SSC at 65° C. for one hour. Another exemplary stringent hybridization scheme uses 50% formamide, 4×SSC at 42° C. Another example of "stringent conditions" refers to conditions of high stringency, for example 6×SSC, 0.2% polyvinylpyrrolidone, 0.2% Ficoll, 0.2% bovine serum albumin, 0.1% sodium dodecyl sulfate, 100 µg/ml salmon sperm DNA and 15% formamide at 68° C. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity can be determined by hybridization under stringent conditions, for example, at 50° C. or higher and 0.1×SSC (9 mM NaCl/0.9 mM sodium citrate).

Nucleic acids that are substantially identical to the provided 3-OST-5 sequences, e.g., allelic variants, genetically altered versions of the gene, etc., bind to the provided 3-OST-5 sequences under stringent hybridization conditions. By using probes, particularly labeled probes of DNA sequences, one can isolate homologous or related genes. The source of homologous genes can be any species, e.g., primate species, particularly human; rodents, such as rats and mice, canines, felines, bovines, ovines, equines, yeast, nematodes, etc.

Between mammalian species, e.g., human, mouse and rat, homologs have substantial sequence similarity, i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nucleotides long, more usually at least about 30 nucleotides long, and can extend to the complete sequence that is being compared. Algorithms for sequence analysis are known in the art, such as BLAST, described in Altschul et al. (1990) *J Mol Biol* 215:403-410. The sequences provided herein are essential for recognizing 3-OST-5 related and homologous proteins in database searches.

At a biological level, identity is just that, i.e. the same amino acid at the same relative position in a given family member of a gene family. Homology and similarity are generally viewed as broader terms. For example, biochemically similar amino acids, for example leucine and isoleucine or glutamate/aspartate, can be present at the same position—these are not identical per se, but are biochemically "similar". As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

The 3-OST-5s disclosed herein are thus homologous proteins, but when percentages are referred to herein, it is meant to refer to percent identity. The percent identities referenced herein were generated by alignments with the program GENEWORKS™ (Oxford Molecular, Inc. of Campbell, Calif., United States of America) and/or the BLAST program at NCBI (http://www.ncbi.nlm.nih.gov/BLAST/). Another commonly used alignment program is entitled CLUSTAL W and is described in Thompson et al. (1994) *Nucleic Acids Res* 22(22):4673-4680, among other places.

Probe sequences can also hybridize specifically to duplex DNA under certain conditions to form triplex or other higher order DNA complexes. The preparation of such probes and suitable hybridization conditions are disclosed herein and are known in the art.

The term "gene" is used for simplicity to refer to a functional protein, polypeptide or peptide encoding unit. As will be understood by those in the art, this functional term includes both genomic sequences and cDNA sequences. Preferred embodiments of genomic and cDNA sequences are disclosed herein.

In particular embodiments, the invention concerns isolated DNA segments and recombinant vectors incorporating DNA sequences, which encode a 3-O-sulfotransferase polypeptide that includes within its amino acid sequence an amino acid sequence as described herein. In other particular embodiments, the invention concerns recombinant vectors incorporating DNA segments, which encode a protein comprising the amino acid sequence of a human 3-OST-5.

I.A. Biologically Functional Equivalents

As mentioned above, modifications and changes can be made in the structure of the 3-OST-5 proteins and peptides described herein and still constitute a molecule having like or otherwise desirable characteristics. For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the native protein, but this need not be the case, and the biological activity of the invention is not limited to a particular mechanism of action. It is thus contemplated in accordance with the present invention that various changes can be made in the sequence of the 3-OST-5 proteins and peptides or underlying nucleic acid sequence without appreciable loss of their biological utility or activity.

Biologically functional equivalent peptides, as used herein, are peptides in which certain, but not most or all, of the amino acids can be substituted. Thus, when referring to the sequence example presented in SEQ ID NO 1, applicants contemplate substitution of codons that encode biologically equivalent amino acids as described herein into the sequence examples of SEQ ID NO 1. Thus, applicants are in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged. Changes designed by man can be introduced through the application of site-directed mutagenesis techniques, e.g., to introduce improvements to the antigenicity of the protein or to test 3-OST-5 mutants in order to examine 3-OST-5 sulfotransferase activity, or other activity at the molecular level.

Amino acid substitutions, such as those which might be employed in modifying the 3-OST-5 proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Other biologically functionally equivalent changes will be appreciated by those of skill in the art.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al. (1982) *J Mol Biol* 157:105, incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those, which are within ±1 of the original value, are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those, which are within ±1 of the original value, are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that this invention is not limited to the particular nucleic acid and amino acid sequences of SEQ ID NOs:1 and 2. Recombinant vectors and isolated DNA segments can therefore variously include the 3-O-sulfotransferase isoform 5 polypeptide-encoding region itself, include coding regions bearing selected alterations or modifications in the basic coding region, or include larger polypeptides which nevertheless comprise 3-O-sulfotransferase isoform 5 polypeptide-encoding regions or can encode biologically functional equivalent proteins or peptides which have variant amino acid sequences. Biological activity of a 3-O-sulfotransferase isoform 5 can be determined as disclosed herein in the Examples.

In particular embodiments, the invention concerns gene therapy methods that use isolated DNA segments and recombinant vectors incorporating DNA sequences which encode a protein comprising an amino acid sequence of SEQ ID NO 2. In other particular embodiments, the invention concerns isolated DNA sequences and recombinant DNA vectors incorporating DNA sequences that encode a protein comprising the amino acid sequence of the 3-O-sulfotransferase isoform 5 protein from vertebrate tissue. In certain other embodiments, the invention concerns isolated DNA segments and recombinant vectors that comprise a nucleic acid sequence essentially as set forth in SEQ ID NO 1.

The nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in any of SEQ ID NO 1 such as about 10 nucleotides, and which are up to 10,000 or 5,000 base pairs in length, with segments of 3,000 being preferred in certain cases. DNA segments with total lengths of about 4,000, 3,000, 2,000, 1,000, 500, 200, 100, and about 50 base pairs in length are also contemplated to be useful.

The DNA segments of the present invention encompass biologically functionally equivalent 3-O-sulfotransferase isoform 5 proteins and peptides. Such sequences can rise as a consequence of codon redundancy and functional equivalency that are known to occur naturally within nucleic acid sequences and the proteins thus encoded. Alternatively, functionally equivalent proteins or peptides can be created via the application of recombinant DNA technology, in which changes in the protein structure can be engineered, based on considerations of the properties of the amino acids being exchanged. Changes can be introduced through the application of site-directed mutagenesis techniques, e.g., to introduce improvements to the antigenicity of the protein or to test 3-O-sulfotransferase mutants in order to examine activity in the modulation of sulfate transfer to HS, or other activity at the molecular level. Site-directed mutagenesis techniques are known to those of skill in the art and are disclosed herein.

The invention further encompasses fusion proteins and peptides wherein the 3-OST-5 coding region is aligned within the same expression unit with other proteins or peptides having desired functions, such as for purification or immunodetection purposes.

Recombinant vectors form important further aspects of the present invention. Particularly useful vectors are those in which the coding portion of the DNA segment is positioned under the control of a promoter. The promoter can be that naturally associated with the 3-OST-5 gene, as can be obtained by isolating the 5' non-coding sequences located upstream of the coding segment or exon, for example, using recombinant cloning and/or polymerase chain reaction (PCR) technology and/or other methods known in the art, in conjunction with the compositions disclosed herein.

In other embodiments, it is contemplated that certain advantages will be gained by positioning the coding DNA segment under the control of a recombinant, or heterologous, promoter. As used herein, a recombinant or heterologous promoter is a promoter that is not normally associated with a 3-O-sulfotransferase gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (See, e.g., Sambrook et al. (2001) *Molecular Cloning: A Laboratory Manual*, Third Edition, Cold Spring Harbor Laboratory Press, Cold Spring Harbor, N.Y.). The promoters employed can be constitutive or inducible and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccinia virus promoter and the baculovirus promoter.

In an alternative embodiment, the present invention provides an expression vector comprising a polynucleotide that encodes a biologically active 3-OST-5 polypeptide in accordance with the present invention. In one example, an expression vector of the present invention comprises a polynucleotide that encodes a 3-OST-5 gene product. In another example, an expression vector of the present invention comprises a polynucleotide that encodes a polypeptide comprising an amino acid residue sequence of SEQ ID NO 2. In yet another example, an expression vector of the present invention comprises a polynucleotide comprising the nucleotide sequence of SEQ ID NO 1. Optionally, an expression vector of the invention comprises a polynucleotide operatively linked to an enhancer-promoter. For example, an expression vector can comprise a polynucleotide operatively linked to a prokaryotic promoter. Alternatively, an expression vector of the present invention comprises a polynucleotide operatively linked to an enhancer-promoter that is a eukaryotic promoter and the expression vector further comprises a polyadenylation signal that is positioned 3' of the carboxy-terminal amino acid and within a transcriptional unit of the encoded polypeptide.

In yet another embodiment, disclosed herein is a recombinant host cell transfected with a polynucleotide that encodes a biologically active 3-OST-5 polypeptide in accordance with the present invention. SEQ ID NOs 1 and 2 set forth representative nucleotide and amino acid sequences from human tissues. Also provided are homologous or biologically functionally equivalent polynucleotides and 3-OST-5 polypeptides found in other vertebrates, including particularly rat and murine homologs. Optionally, a recombinant host cell of the present invention is transfected with the polynucleotide that encodes a human 3-OST-5 polypeptide. As another option, a recombinant host cell is transfected with the polynucleotide sequence encoding or set forth in SEQ ID NOs 1 and 2. A recombinant host cell is a mammalian cell or an insect cell.

In another aspect, a recombinant host cell is a prokaryotic host cell, including parasitic and bacterial cells. Preferably, a recombinant host cell is a bacterial cell, for example, a strain of *Escherichia coli*. The recombinant host cell can comprise a polynucleotide under the transcriptional control of regulatory signals functional in the recombinant host cell, wherein the regulatory signals appropriately control expression of the 3-OST-5 polypeptide in a manner to enable all necessary transcriptional and post-transcriptional modification.

In yet another embodiment, provided is a process of preparing a 3-OST-5 polypeptide comprising transfecting a cell with polynucleotide that encodes a biologically active 3-OST-5 polypeptide as disclosed herein, to produce a transformed host cell, and maintaining the transformed host cell under biological conditions sufficient for expression of the polypeptide. The polypeptide can be isolated if desired, using any suitable technique. The host cell can be a prokaryotic or eukaryotic cell, such as, but not limited to a bacterial cell of *Escherichia coli*. More preferably, a polynucleotide transfected into the transformed cell comprises the nucleotide base sequence of SEQ ID NO1. SEQ ID NOs 1 and 2 set forth nucleotide and amino acid sequences for representative human vertebrates. Also provided are homologs or biologically equivalent 3-OST-5 polynucleotides and polypeptides found in other vertebrates, particularly warm-blooded vertebrates, more particularly mammals, and even more particularly murine homologs.

As mentioned above, in connection with expression embodiments to prepare recombinant 3-OST-5 and peptides, it is contemplated that longer DNA segments will most often be used, with DNA segments encoding the entire 3-OST-5 protein, functional domains or cleavage products thereof, being most preferred. However, it will be appreciated that the use of shorter DNA segments to direct the expression of 3-OST-5 peptides, epitopes or core regions, such as can be used to generate anti-3-OST-5 antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full-length proteins can have a minimum coding length on the order of about 4,000 or 5,000 nucleotides for a protein in accordance with SEQ ID NO 1. DNA segments of the present invention can contain 300, 400, 500, 1,000, 1,500, 2,000, 2,500, 3,000, 3,500, 4,000, 4,500, or up to 5,000 nucleotides. Peptides of the present invention can contain 10, 20, 50, 100, 200, 300, 400, 500, 750, 1,000, or up to 1,500 amino acids.

I.B. Sequence Modification Techniques

Modifications to the 3-OST-5 proteins and peptides described herein can be carried out using techniques known in the art, including site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants; for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al. (1983) DNA 2:183; Sambrook et al. (2001) *Molecular Cloning: A Laboratory Manual*, Third Edition, Cold Spring Harbor Laboratory Press, Cold Spring Harbor, N.Y.) and can be achieved in a variety of ways generally known to those of skill in the art.

I.C. Other Structural Equivalents

The knowledge of the structure of the 3-OST-5 polypeptide of the present invention provides for the investigation of the mechanism of action of these proteins in a subject. For example, binding of these proteins to various substrate molecules is disclosed in the examples and can be predicted by various computer models. Upon discovering that such binding in fact takes place, knowledge of the protein structure then allows design and synthesis of small molecules, which mimic the functional binding of the 3-OST-5 polypeptide to the substrate. This is the method of "rational" drug design.

Use of the isolated and purified 3-OST-5 polypeptide in rational drug design is thus provided. Additional rational drug design techniques are described in U.S. Pat. Nos. 5,834,228 and 5,872,011, herein incorporated by reference in their entirety.

Thus, in addition to the peptidyl compounds described herein, other sterically similar compounds can be formulated to mimic the key portions of the peptide structure. Such compounds can be used in the same manner as the peptides of the invention and hence are also functional equivalents. The generation of a structural functional equivalent can be achieved by the techniques of modeling and chemical design known to those of skill in the art. It will be understood that all such sterically similar constructs fall within the scope of the present invention.

II. Introduction of Gene Products

In accordance with the present invention, where a 3-OST-5 gene itself is employed to introduce a 3-OST-5 gene product, a convenient method of introduction will be through the use of a recombinant vector that incorporates the desired gene, together with its associated control sequences. The preparation of recombinant vectors is well known to those of skill in the art and described in many references, such as, for example, Sambrook et al. (2001) *Molecular Cloning: A Laboratory Manual*, Third Edition, Cold Spring Harbor Laboratory Press, Cold Spring Harbor, N.Y., incorporated herein in its entirety.

II.A. Vector Construction

It is understood that the DNA coding sequences to be expressed, in this case those encoding the 3-OST-5 gene products, are positioned in a vector adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter.

One can also desire to incorporate into the transcriptional unit of the vector an appropriate polyadenylation site (e.g., 5'-AATAAA-3'), if one was not contained within the original inserted DNA. Typically, these poly-A addition sites are placed about 30 to 2000 nucleotides "downstream" of the coding sequence at a position prior to transcription termination.

While use of the control sequences of the specific gene will be preferred, other control sequences can be employed, so long as they are compatible with the genotype of the cell being treated. Thus, one can mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs upstream of (i.e., 5' to) the point at which transcription begins (i.e., a transcription start site). That region typically contains several types of DNA sequence elements that are located in similar relative positions in different genes.

Another type of discrete transcription regulatory sequence element is an enhancer. An enhancer imposes specificity of time, location and expression level on a particular coding region or gene. A major function of an enhancer is to increase the level of transcription of a coding sequence in a cell that contains one or more transcription factors that bind to that enhancer. An enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art; the precise orientation and location relative to a coding sequence of interest is dependent, inter alia, upon the specific nature of the enhancer-promoter.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, a human 3-OST-5 gene, a vector construct that will deliver the gene to cells of interest is desired. Viral vectors can be used. These vectors can optionally be a HSV-1, an adenovirus, a retrovirus, such as a Lentivirus, a vaccinia virus vector or an adeno-associated virus; these vectors have been successfully used to deliver desired sequences to cells and tend to have a high infection efficiency. Suitable vector-3-OST-5 gene constructs are adapted for administration as pharmaceutically acceptable formulation, as described herein below. Viral promoters can also be of use in vectors of the present invention, and are known in the art.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment that also contains the SV40 viral origin of replication. Smaller or larger SV40 fragments can also be used, provided there is included the approximately 250 base pair sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication can be provided either by construction of the vector to include an exogenous origin, such as can be derived from SV40 or other viral source, or can be provided by the host cell chromosomal replication mechanism. If the vector is integrated into the host cell chromosome, the latter is often sufficient.

Where a 3-OST-5 gene itself is employed it will be most convenient to simply use a wild type 3-OST-5 gene directly. However, it is contemplated that certain regions of a 3-OST-5 gene can be employed exclusively without employing an entire wild type 3-OST-5 gene. It is proposed that it will ultimately be preferable to employ the smallest region needed to modulate biological activity so that one is not introducing unnecessary DNA into cells that receive a 3-OST-5 gene construct. The ability of these regions to modulate biological activity can be determined by the assays reported in the Examples.

II.B. Transgenic Animals

It is also within the scope of the present invention to prepare a transgenic non-human animal that expresses a xenogeneic 3-OST-5 gene as described herein. A preferred transgenic animal is a mouse.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

With respect to a representative method for the preparation of a transgenic mouse, cloned recombinant or synthetic DNA sequences or DNA segments encoding a 3-OST-5 gene product are injected into fertilized mouse eggs. The injected eggs are implanted in pseudo pregnant females and are grown to term to provide transgenic mice whose cells express a 3-OST-5 gene product.

For example, a transgenic animal of the present invention comprises a mouse with targeted modification of the mouse 3-OST-5 gene. Mice strains with complete (e.g. knockout) or partial functional inactivation of the 3-OST-5 gene in all somatic cells are generated using standard techniques of site-specific recombination in murine embryonic stem cells. See Capecchi (1989) *Science* 244(4910):1288-1292; Thomas & Capecchi (1990) *Nature* 346(6287):847-850; Delpire et al. (1999) *Nat Genet* 22(2):192-195.

Alternatives include the use of anti-sense or ribozyme 3-OST-5 constructs, driven by a universal or tissue-specific promoter, to reduce levels of individual 3-OST-5s in somatic cells, thus achieving a "knock-down" of individual isoforms (Luyckx et al. (1999) *Proc Natl Acad Sci USA* 96(21):12174-12179). The invention also provides the generation of murine strains with conditional or inducible inactivation of individual or multiple 3-OST-5 genes (Sauer (1998) *Methods* 14(4):381-392). For example, mice are created which lack expression of any 3-OST-5s in muscle tissue, a known site of expression of 3-OST-5.

The present invention also includes mice strains with specific "knocked-in" modifications in the 3-OST-5 gene. This includes mice with genetically (Forlino et al. (1999) *J Biol Chem* 274(53):37923-37931) and functionally (Kissel et al. (2000) *EMBO J* 19(6):1312-1326) relevant point mutations in the 3-OST-5 gene, in addition to manipulations such as the insertion of disease-specific repeat expansions (White et al. (1997) *Nat Genet* 17(4):404-410).

III. Generation of Antibodies

In still another embodiment, an antibody immunoreactive with a polypeptide as disclosed herein is provided. Preferably, an antibody of the invention is a monoclonal antibody. Techniques for preparing and characterizing antibodies are well known in the art (See e.g., Harlow & Lane (1988) *Antibodies: A Laboratory Manual*, Cold Spring Harbor Laboratory Press, Cold Spring Harbor, N.Y.

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Because of the relatively large blood volume of rabbits, a rabbit is a preferred choice for production of polyclonal antibodies.

As is well known in the art, a given polypeptide or polynucleotide can vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, NCmaleimidobencoyl-N-hydroxysuccinimide ester, carbodiimide and bis-biazotized benzidine.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies, inter alia, upon the nature of the immunogen as well as the animal used for immunization. A variety of routes can be used to administer the immunogen, e.g., subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention provides a process of producing an antibody immunoreactive with a 3-OST-5 polypeptide, the process comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the 3-OST-5 polypeptide is capable of modulating 3-O-sulfotransferase activity within or outside of cells in accordance with the present invention.

A monoclonal antibody of the present invention can be readily prepared through use of well-known techniques such as the hybridoma techniques exemplified in U.S. Pat. No 4,196,265 and the phage-displayed techniques disclosed in U.S. Pat. No. 5,260,203, the contents of which are herein incorporated by reference.

A typical technique involves first immunizing a suitable animal with a selected antigen (e.g., a polypeptide or polynucleotide of the present invention) in a manner sufficient to provide an immune response. Rodents such as mice and rats are representative animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. This culturing provides a population of hybridomas from which specific hybridomas are selected. Typically, selection of hybridomas is performed by culturing the cells by single-clone dilution in microtiter plates, followed by testing the individual clonal supernatants for reactivity with antigen-polypeptides. The selected clones can then be propagated indefinitely to provide the monoclonal antibody.

By way of specific example, to produce an antibody of the present invention, mice are injected intraperitoneally with between about 1-200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus "immortal". Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, and thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

IV. Detecting a Polynucleotide or a Polypeptide

Also disclosed herein is a process of detecting a 3-OST-5 polypeptide, wherein the process comprises immunoreacting the polypeptide with an antibody prepared according to the process described above to form an antibody-polypeptide conjugate, and detecting the conjugate.

In another embodiment, disclosed is a process of detecting messenger RNA transcripts that encode a 3-OST-5 polypeptide, wherein the process comprises hybridizing the messenger RNA transcripts with polynucleotide sequences that encode the polypeptide to form duplexes; and detecting the duplex. Alternatively, provided is a process of detecting DNA molecules that encode a 3-OST-5 polypeptide, wherein the process comprises hybridizing DNA molecules with a polynucleotide that encodes that polypeptide to form duplexes; and detecting the duplexes.

The detection and screening assays disclosed herein can optionally be used as a prognosis tool and/or diagnostic aid. 3-OST-5 encoding polypeptides and nucleic acids can be readily used in clinical setting as a prognostic and/or diagnostic indicator for screening for levels of expression of 3-OST-5s, or alterations in native sequences. The nucleotide sequences of the subject invention can be used to detect differences in gene or gene product sequences between normal, carrier, or affected individuals. Such differences can include single-nucleotide changes or multiple changes, deletions, or additions in the native sequence which result in altered transcription, translation, or activity or biological activity or properties of the gene or gene product. These differences can be readily detected using the compositions of the present invention and techniques known in the art, including but not limited to SSCP analysis, RFLP analysis, or other PCR- or nucleotide-based analysis.

DNA segments or RNA having the sequence of, or a sequence complementary to, SEQ ID NO 1 can be used. Such polynucleic acids can comprise 10, 20, 40, 50, 70, 100, 250, 300, 400, 500, or 1,000 nucleotides or up to the full length of SEQ ID NO 1. Such polynucleic acids can, but need not, encode polypeptides that retain some or all of the biological activity of the native gene or gene product.

IV.A. Screening Assays for a Polypeptide

Also provided is a process of screening a biological sample for the presence of a 3-OST-5 polypeptide. A biological sample to be screened can be a biological fluid such as extracellular or intracellular fluid, or a cell or tissue extract or homogenate. A biological sample can also be an isolated cell (e.g., in culture) or a collection of cells such as in a tissue sample or histology sample, from any desired tissue, such as skeletal muscle, brain, and/or another desired tissue. A tissue sample can be suspended in a liquid medium or fixed onto a solid support such as a microscope slide.

In accordance with a screening assay process, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate). Additional details of methods for such assays are known in the art. The presence of polypeptide in the sample is detected by evaluating the formation and presence of antibody-polypeptide conjugates. Techniques for detecting such antibody-antigen conjugates or complexes are well known in the art and include but are not limited to centrifugation, affinity chromatography and the like, and binding of a secondary antibody to the antibody-candidate receptor complex.

In one embodiment, detection is accomplished by detecting an indicator affixed to the antibody. Exemplary and well-known indicators include radioactive labels (e.g., $^{32}P$, $^{125}I$, $^{14}C$), a second antibody or an enzyme such as horseradish peroxidase. Techniques for affixing indicators to antibodies are known in the art.

IV.B. Screening Assay for Anti-Polypeptide Antibody

In another aspect, provided is a process of screening a biological sample for the presence of antibodies immunoreactive with a 3-OST-5 polypeptide. In one embodiment the antibody so identified has activity in the modulation of 3-OST-5 biological activity. In accordance with such a process, a biological sample is exposed to a 3-OST-5 polypeptide under biological conditions and for a period of time sufficient for antibody-polypeptide conjugate formation and the formed conjugates are detected.

IV.C. Detection of a Polynucleotide That Encodes a 3-OST-5 Polypeptide

A DNA or RNA molecule and particularly a DNA segment or polynucleotide can be used for hybridization to a DNA or RNA source or sample suspected of encoding a 3-OST-5 polypeptide; such molecules are referred to as "probes," and such hybridization is "probing". Such probes can be made synthetically. The probing is usually accomplished by hybridizing the oligonucleotide to a DNA source suspected of possessing a 3-OST-5 gene. In some cases, the probes constitute only a single probe, and in others, the probes constitute a collection of probes based on a certain amino acid sequence or sequences of the polypeptide and account in their diversity for the redundancy inherent in the genetic code.

Other molecules which are neither DNA nor RNA but are capable of hybridizing in a similar manner and which are designed structurally to mimic the DNA or RNA sequence of a 3-OST-5 gene are also provided. Here, a suitable source to examine is capable of expressing a polypeptide of the present invention and can be a genomic library of a cell line of interest. Alternatively, a source of DNA or RNA can include total DNA or RNA from the cell line of interest. Once the hybridization process of the invention has identified a candidate DNA segment, a positive clone can be confirmed by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) reagents for detecting and isolating other members of the polypeptide family and related polypeptides from a DNA library potentially containing such sequences; (3) primers for hybridizing to related sequences for the purpose of amplifying those sequences; (4) primers for altering native 3-OST-5 DNA sequences; as well as (5) other techniques which rely on the similarity of the sequences of interest to those of the sequences herein disclosed.

As set forth above, in certain aspects, DNA sequence information provided herein allows for the preparation of probes that specifically hybridize to encoding sequences of a selected 3-OST-5 gene. In these aspects, probes of an appropriate length are prepared based on a consideration of the encoding sequence for a polypeptide of this invention. The ability of such probes to specifically hybridize to other encoding sequences lends them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to or mimic at least a 14 to 40 or so long nucleotide stretch of a nucleic acid sequence of the present invention, such as a sequence shown in SEQ ID NO 1. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired, such as 30, 40, 50, 60, 100, 200, 300, or 500 nucleotides or up to the full length of any of SEQ ID NO 1. Such fragments can be readily prepared by, for example, directly synthesizing the fragment by chemical synthesis, by application of nucleic acid amplification technology, such as the PCR technology of U.S. Pat. No. 4,683,202, herein incorporated by reference, or by introducing selected sequences into recombinant vectors for recombinant production.

Accordingly, a nucleotide sequence as disclosed herein can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M-0.15M salt (e.g., NaCl), including particularly 200 mM salt, at temperatures of 50° C. to 70° C., including particularly temperatures of about 55° C., about 60° C. and about 65° C. Such conditions are particularly selective, and tolerate little, if any, mismatch between the probe and the template or target strand.

Of course, for some applications, less stringent hybridization conditions are typically needed to allow formation of the heteroduplex; one of skill in the art will know how to adjust the hybridization conditions for optimizing particular procedures. For example, it is generally appreciated that conditions can be rendered more stringent by the addition of increasing amounts of formamide, which serves to destabilize the hybrid duplex in the same manner as increased temperature. Thus, hybridization conditions can be readily manipulated by one of skill in the art using known methods to carry out the desired function or experiment, without undue experimentation.

In one embodiment, the 3-OST-5 sequences disclosed herein were used to detect a 3-OST-5 RNA polynucleotide as described in Example 5.

IV.D. Detection Assay Kits

In another aspect, provided are assay kits for detecting the presence of a polypeptide of the present invention in biological samples, where the kits comprise a first antibody capable of immunoreacting with the polypeptide. The assay kits can further comprise a second container containing a second antibody that immunoreacts with the first antibody. Optionally, the antibodies used in the assay kits are monoclonal antibodies. The first antibody can be affixed to a solid support. The first and second antibodies can comprise an indicator, such as but not limited to a radioactive label or an enzyme.

Also provided is an assay kit for screening agents. Such a kit can contain a polypeptide as disclosed herein. The kit can additionally contain reagents for detecting an interaction between an agent and a polypeptide as disclosed herein.

In an alternative aspect, provided are assay kits for detecting the presence, in biological samples, of a polynucleotide that encodes a polypeptide as disclosed herein. The kits can comprise a first container that contains a second polynucleotide identical or complementary to a segment of at least 10 contiguous nucleotide bases of, as one example, SEQ ID NO 1. In another embodiment, the assay kit can be used for detecting the presence, in a biological sample, of antibodies immunoreactive with a 3-OST-5 polypeptide. The kit can comprise a 3-OST-5 polypeptide that immunoreacts with the antibodies.

V. Screening for Modulators of 3-OST-5 Biological Activity

In yet another aspect, provided is a process of screening substances for their ability to affect or modulate the biological activity of 3-OST-5 gene products, and for their ability to affect or to modulate in vivo 3-OST-5 levels. Also provided is a process of screening substances for their ability to affect or modulate the biological activity of 3-OST-5 gene products, and for their ability to affect or modulate in vivo 3-OST-5 levels.

Utilizing the methods and compositions disclosed herein, screening assays for the testing of candidate substances are performed. A candidate substance is a substance that can promote or inhibit the biological activity of gene product by binding or other intermolecular interaction with the 3-OST-5 gene or gene product or control sequence.

V.A. Method of Screening for Modulators of 3-OST-5 Biological Activity

A representative method of screening candidate substances for their ability to modulate 3-OST-5 biological activity comprises: (a) establishing replicate test and control samples that comprise a biologically active 3-OST-5 polypeptide; (b) administering a candidate substance to test samples; (c) measuring the biological activity of the 3-OST-5 polypeptide in the test and the control samples; and (d) determining whether the candidate substance modulates 3-OST-5 biological activity relative to an appropriate control. By "modulate" is intended an increase, decrease, or other alteration of any or all of the biological activities or properties of 3-OST-5. A candidate substance identified according to the screening assay described herein has an ability to modulate 3-OST-5 biological activity. Such a candidate compound has utility in the treatment of disorders and conditions associated with the biological activity of a 3-OST-5. Candidate compounds are typically about 500-1000 daltons, and can be hydrophobic, polycyclic, or both, molecules.

In a cell-free system, the method comprises the steps of establishing a control system comprising a 3-OST-5 polypeptide and a ligand to which the 3-OST-5 polypeptide is capable of binding, establishing a test system comprising the 3-OST-5 polypeptide, the ligand, and a candidate compound, and determining whether the candidate compound modulates 3-OST-5 activity in a cell-free system. A representative ligand comprises a monoclonal antibody, and in this embodiment, the biological activity or property screened includes binding affinity.

In another embodiment of the invention, a 3-OST-5 polypeptide or catalytic or immunogenic fragment or oligopeptide thereof, can be used for screening libraries of compounds in any of a variety of drug screening techniques. The fragment employed in such screening can be free in solution, affixed to a solid support, borne on a cell surface, or located intracellularly. The formation of binding complexes, between the 3-OST-5 polypeptide and the agent being tested, can be measured.

Another technique for drug screening that can be used provides for high throughput screening of compounds having suitable binding affinity to the protein of interest as described in published International Publication Number WO 84/03564, herein incorporated by reference. In this method, as applied to the 3-OST-5 polypeptide, large numbers of different small test compounds are synthesized on a solid substrate, such as plastic pins or some other surface. The test compounds are reacted with the 3-OST-5 polypeptide, or fragments thereof, and washed. Bound 3-OST-5 polypeptide is then detected by methods well known in the art. Purified 3-OST-5 polypeptide can also be coated directly onto plates for use in the aforementioned drug screening techniques. Alternatively, non-neutralizing antibodies can be used to capture the peptide and immobilize it on a solid support.

A screening assay of the present invention can also involve determining the ability of a candidate substance to modulate, i.e. inhibit or promote 3-OST-5 biological activity and preferably, to thereby modulate the biological activity of 3-OST-5 in target cells. Target cells can be either naturally occurring cells known to contain a polypeptide as disclosed herein or transformed cells produced in accordance with a process of transformation set forth herein above. The test samples can further comprise a cell or cell line that expresses a 3-OST-5 polypeptide; the present invention also provides a recombinant cell line suitable for use in the exemplary method. Such cell lines can be mammalian, such as human, or they can from another organism, including but not limited to yeast. Exemplary assays include genetic screening assays and molecular biology screens such as a yeast two-hybrid screen that will effectively identify 3-OST-5-interacting genes involved in a 3-OST-5-mediated cellular process. One version of the yeast two-hybrid system has been described (Chien et al. (1991) *Proc Natl Acad Sci USA*, 88:9578-9582) and is commercially available from Clontech (Palo Alto, Calif., United States of America).

As is well known in the art, a screening assay can provide a cell under conditions suitable for testing the modulation of 3-OST-5 biological activity and/or levels of 3-OST-5s. These conditions include but are not limited to pH, temperature, tonicity, the presence of relevant metabolic factors (e.g., metal ions such as for example $Ca^{++}$, growth factor, interleukins, or colony stimulating factors), and relevant modifications to the polypeptide such as glycosylation or prenylation. It is contemplated that a polypeptide as disclosed herein can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell. U.S. Pat. Nos. 5,837,479; 5,645,999; 5,786, 152; 5,739,278; and 5,352,660 also describe exemplary screening assays, and the entire contents of each are herein incorporated by reference.

In one embodiment, a screening assay is designed to be capable of discriminating candidate substances having selective ability to interact with or modulate one or more of the genes or gene products as disclosed herein but which substances are without a substantially overlapping activity with another gene or gene product. For example, a substance can modulate the biological activity of 3-OST-5 but have no effect, or a diminished effect, on other 3-OST isoforms. Such selective effect can comprise a 30% greater effect on one test sample versus another, or more preferably 100% or greater effect.

A method of identifying modulators of 3-OST-5s by rational drug design is also provided herein. In one embodiment the method comprises designing a potential modulator for a 3-OST-5 that will form non-covalent bonds with amino acids in the substrate binding site based upon the structure of a 3-OST-5 polypeptide; synthesizing the modulator; and determining whether the potential modulator modulates the activity of a 3-OST-5. Modulators can be synthesized using techniques known in the art. The determination of whether the modulator modulates the biological activity of a 3-OST-5 is made in accordance with the screening methods disclosed herein, or by other screening methods known in the art.

V.B. Method of Screening for Modulators of In vivo 3-OST-5 Levels

There is also provided a method for screening candidate compounds for the ability to modulate in vivo 3-OST-5 levels and/or activity. Representative modulators of 3-OST-5 levels can comprise modulators of 3-OST-5 transcription or expression. Pharmaceuticals that increase or decrease the transcription or expression of 3-OST-5 encoding genes have important clinical application for the modulation of the biological activity of 3-OST-5.

This invention thus includes a method for discovery of compounds that modulate the expression levels of 3-OST-5 encoding genes, and describes the use of such compounds. The general approach is to screen compound libraries for substances that increase or decrease expression of 3-OST-5-encoding genes. Exemplary techniques are described in U.S. Pat. Nos. 5,846,720 and 5,580,722, the entire contents of each of which are herein incorporated by reference.

While the following terms are believed to be well understood by one of skill in the art, the following definitions are set forth to facilitate explanation of the invention.

"Transcription" means a cellular process involving the interaction of an RNA polymerase with a gene that directs the expression as RNA of the structural information present in the coding sequences of the gene. The process includes, but is not limited to the following steps: (a) the transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript. "Expression" generally refers to the cellular processes by which a biologically active polypeptide is produced from RNA.

"Transcription factor" means a cytoplasmic or nuclear protein that binds to such gene, or binds to an RNA transcript of such gene, or binds to another protein which binds to such gene or such RNA transcript or another protein which in turn binds to such gene or such RNA transcript, so as to thereby modulate expression of the gene. Such modulation can additionally be achieved by other mechanisms; the essence of "transcription factor for a gene" is that the level of transcription of the gene is altered in some way.

In one embodiment there is provided a method of identifying a candidate compound or molecule that is capable of modulating the transcription level of a gene encoding a 3-OST-5 and thus is capable of acting as a therapeutic agent in the modulation of 3-OST-5 effects. Such modulation can be direct, i.e., through binding of a candidate molecule directly to the nucleotide sequence, whether DNA or RNA transcript, or such modulation can be achieved via one or more intermediaries, such as proteins other than 3-OST-5 which are affected by the candidate compound and ultimately modulate 3-OST-5 transcription by any mechanism, including direct binding, phosphorylation or dephosphorylation, etc.

This method comprises contacting a cell or nucleic acid sample with a candidate compound or molecule to be tested. These samples contain nucleic acids that can contain elements that modulate transcription and/or translation of the 3-OST-5 gene, such as a 3-OST-5 promoter or putative upstream regulatory region, and a DNA sequence encoding a polypeptide which can be detected in some way. Thus, the polypeptide can be described as a "reporter" or "marker." Preferably, the candidate compound directly and specifically transcriptionally modulates expression of the 3-OST-5-encoding gene. Such compounds are anticipated to have therapeutic or pharmaceutical uses in treating 3-OST-5-related diseases and/or disorders.

The DNA sequence is coupled to and under the control of the promoter, under conditions such that the candidate compound or molecule, if capable of acting as a transcriptional modulator of the gene encoding 3-OST-5, causes the polypeptide to be expressed and so produces a detectable signal, which can be assayed quantitatively and compared to an appropriate control. Candidate compounds or molecules of interest can include those that increase or decrease, i. e., modulate, transcription from the 3-OST-5 promoter. The reporter gene can encode a reporter known in the art, such as luciferase, or it can encode 3-OST-5.

In certain embodiments the polypeptide so produced is capable of complexing with an antibody or is capable of complexing with biotin. In this case the resulting complexes can be detected by methods known in the art. The detectable signal of this assay can also be provided by messenger RNA produced by transcription of the reporter gene. Exactly how the signal is produced and detected can vary and is not the subject of the present invention; rather, the present invention provides the nucleotide sequences and/or putative regulatory regions of 3-OST-5 for use in such an assay. The molecule to be tested in these methods can be a purified molecule, a homogenous sample, or a mixture of molecules or compounds. Further, the DNA in the cell can comprise more than one modulatable transcriptional regulatory sequence.

There is also provided a rapid and high throughput screening method that relies on the methods described above. This screening method comprises separately contacting each of a plurality of substantially identical samples. In such a screening method the plurality of samples preferably comprises more than about $10^4$ samples, or more preferably comprises more than about $5 \times 10^4$ samples.

V.C. Animal Models

In addition, animal-based systems can be used to identify compounds capable of modulating 3-OST-5 biological activity. Such animal models can be used for the identification of drugs, pharmaceuticals, therapies, and interventions that can be effective in modulating 3-OST-5 biological activity. For example, animal models can be exposed to a compound that is suspected of exhibiting an ability to modulate 3-OST-5 biological activity symptoms at a sufficient concentration and for a time sufficient to elicit such modulation of 3-OST-5 biological activity symptoms in the exposed animals. The response of the animals to the exposure can be monitored by assessing in vivo 3-OST-5 expression levels and activity, or by testing biological samples from the animal. As in the methods described above, the mechanism by which a compound modulates 3-OST-5, or achieves therapeutic effects can vary; the utility does not depend on the precise mechanism by which an effect is achieved.

For example, an animal model can comprises a mouse with targeted modification of the mouse 3-OST-5 gene. Mice strains with complete or partial functional inactivation of the 3-OST-5 genes in all somatic cells are generated using standard techniques of site-specific recombination in murine embryonic stem cells. See Capecchi (1989) *Science* 244(4910):1288-92; Thomas & Capecchi (1990) *Nature* 346 (6287):847-50; Delpire et al. (1999) *Nat Genet* 22(2):192-5.

Alternatives include the use of anti-sense or ribozyme 3-OST-5 constructs, driven by a universal or tissue-specific promoter, to reduce levels of individual 3-OST-5s in somatic cells, thus achieving a "knock-down" of individual isoforms (Luyckx et al. (1999) *Proc Natl Acad Sci USA* 96(21):12174-12179). Also provided is the generation of murine strains with conditional or inducible inactivation of individual or multiple 3-OST-5 genes (Sauer (1998) *Methods* 14(4):381-392).

Also provided are mice strains with specific "knocked-in" modifications in the 3-OST-5 gene. This includes mice with genetically (Forlino et al. (1999) *J Biol Chem* 274(53):37923-37931) and functionally (Kissel et al. (2000) *EMBO J* 19(6): 1312-1326) relevant point mutations in the 3-OST-5 genes, in addition to manipulations such as the insertion of disease-specific repeat expansions (White et al. (1997) *Nat Genet* 17(4):404-410).

An aspect of the present disclosure encompasses any treatments that alter any aspect of 3-O-sulfotransferase-mediated biological activity. Such compounds should be considered as candidates for human therapeutic intervention in accordance with the methods described herein below. Dosages of test agents can be determined by deriving dose-response curves, such as those disclosed in U.S. Pat. No. 5,849,578, herein incorporated by reference.

VI. Therapeutic Methods

As used herein, the terms "activity" and "biological activity" are meant to be synonymous and are meant to refer to any biological activity of, for example, a 3-OST-5 polypeptide. Representative biological activities of 3-OST-5 comprise transfer of sulfate to the 3-OH position of a glucosamine residue of heparan sulfate, production of 3-O-sulfated heparan sulfate, assisting viral infection, regulating blood coagulation and embryonic development, and suppressing tumor growth.

With respect to a representative therapeutic method, a subject can be a vertebrate subject, for example, a warm-blooded vertebrate. A representative warm-blooded vertebrate is a mammal. Representative mammals include one of a mouse and a human. As used herein and in the claims, the terms "subject" and "patient" include both human and animal subjects. Thus, veterinary therapeutic uses are provided in accordance with the present invention.

Provided is the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, provided is the treatment of livestock, including, but not limited to, domesticated swine, ruminants, ungulates, horses, poultry, and the like.

The term "target tissue" refers to any cell or group of cells present in a subject wherein modulation of one or more 3-OST-5 biological activities is desired/desirable. This term includes single cells and populations of cells. The term includes, but is not limited to, cell populations comprising blood vessel tissue and other vascular tissue; brain, spinal cord, and other neurological tissue; and muscle tissue, including in one embodiment skeletal muscle tissue. Vascular anomalies also comprise examples of target tissues. Further, it includes but is not limited to such abnormal cells as neoplastic or tumor cells, whether individually or as a part of solid or metastatic tumors.

As used herein, the term "cancer" encompasses cancers in all forms, including polyps, neoplastic cells, and pre-neoplastic cells.

As used herein, the term "neoplastic" is intended to refer to its ordinary meaning, namely aberrant growth characterized by abnormally rapid cellular proliferation. In general, the term "neoplastic" encompasses growth that can be either benign or malignant, or a combination of the two.

The term "tumor" as used herein encompasses both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas. The term "tumor" also encompasses radioresistant tumors, including radioresistant variants of any of the tumors listed above.

VI.A. Modulation of 3-OST-5 Biological Activity

In one embodiment, a therapeutic method comprises administering to a subject a substance that modulates, i.e., inhibits or promotes 3-OST-5 biological activity. Such a substance can be identified according to any of the screening assays set forth above, either in vitro or in vivo. The method comprises treating a vertebrate subject suffering from a disorder associated with or mediated by 3-OST-5 biological activity by administering to the subject an effective amount of a substance identified according to a screening assay described above. By the term "modulating", it is contemplated that the substance can either promote or inhibit the biological activity of 3-OST-5 polypeptides, depending on the disorder to be treated, and can affect one or several of the 3-OST-5s, including 3-OST-5, as well as other forms of 3-OST-5s, or other unrelated genes or gene products. Therapeutic treatment can comprise the administration of antibodies against a chosen region of 3-OST-5s, the administration of a protein that enhances activity, or the administration of a protein that inhibits the transcription of the 3-OST-5.

Such administration can provide treatment of disorders that can be caused or exacerbated by 3-O-sulfotransferase-mediated mechanisms, including but not limited to transfer of sulfate to the 3-OH position of a glucosamine residue of heparan sulfate and production of 3-O-sulfated heparan sulfate. The 3-O-sulfated heparan sulfate can be an anticoagulant-active heparan sulfate. The 3-O-sulfated heparan sulfate can be an antithrombin-binding heparan sulfate, an entry receptor for HSV-1, or both an anticoagulant-active heparan sulfate and an entry receptor for HSV-1. The 3-O-sulfated heparan sulfate can comprise a disaccharide selected from the group consisting of: L-iduronic acid 2-O-sulfate-2,5,-anhydromannitol 3-O-sulfate; D-glucuronic acid-2,5,-anhydromannitol 3,6-O-sulfate; L-iduronic acid 2-O-sulfate-2,5,-anhydromannitol 3,6-O-sulfate; L-iduronic acid-2,5-anhydromannitol 3,6-O-sulfate; L-iduronic acid-2,5-anhydromannitol 3-O-sulfate; D-glucuronic acid-2,5-anhydromannitol 3-O-sulfate; $\Delta^{4,5}$-uronic acid-glucosamine N,3-disulfate; and $\Delta^{4,5}$-uronic acid-glucosamine N-sulfate-iduronic acid 2-sulfate-glucosamine 3,6-disulfate.

In one embodiment, disclosed is a method for modulating transfer of sulfate to the 3-OH position of a glucosamine residue of heparan sulfate in a vertebrate subject. The method can comprise introducing to a tissue producing heparan sulfate in the vertebrate subject a construct comprising a nucleic acid sequence encoding a heparan sulfate 3-O-sulfotransferase 5 gene product operatively linked to a promoter, wherein production of the heparan sulfate 3-O-sulfotransferase 5 gene product in the tissue results in modulation of transfer of sulfate to the 3-OH position of a glucosamine residue of heparan sulfate.

The construct can further comprise a vector selected from the group consisting of a plasmid vector or a viral vector. Optionally, the construct can comprise a liposome complex. The heparan sulfate 3-O-sulfotransferase 5 gene product can comprise a protein having an amino acid sequence as set forth in SEQ ID NO 2. The nucleic acid sequence can be selected from the group consisting of: a DNA acid sequence as set forth in SEQ ID NO 1, or its complementary strands; a DNA sequence which hybridizes to a nucleic acid sequence as set forth in SEQ ID NO 1 under wash stringency conditions represented by a wash solution having about 200 mM salt concentration and a wash temperature of at least about 45° C., and which encodes a heparan sulfate 3-O-sulfotransferase 5 polypeptide; and a DNA sequence differing from an isolated nucleic acid molecule above due to degeneracy of the genetic code, and which encodes a heparan sulfate 3-O-sulfotransferase 5 polypeptide encoded by the isolated nucleic acid molecule above.

In an other embodiment, a method for modulating production of 3-O-sulfated heparan sulfate in a vertebrate subject is disclosed, wherein the method comprises introducing to a tissue comprising cells producing heparan sulfate in the vertebrate subject a construct comprising a nucleic acid sequence encoding a heparan sulfate 3-O-sulfotransferase 5 gene product operatively linked to a promoter, wherein production of the heparan sulfate 3O-sulfotransferase 5 gene product in the tissue results in modulation of production of 3-O-sulfated heparan sulfate. The 3-O-sulfated heparan sulfate can be an anticoagulant-active heparan sulfate. The 3-O-sulfated heparan sulfate can be an antithrombin-binding heparan sulfate, an entry receptor for HSV-1, or both an anticoagulant-active heparan sulfate and an entry receptor for HSV-1. The 3-O-sulfated heparan sulfate can comprise a disaccharide selected from the group consisting of: L-iduronic acid 2-O-sulfate-2,5,-anhydromannitol 3-O-sulfate; D-glucuronic acid-2,5,-anhydromannitol 3,6-O-sulfate; L-iduronic acid 2-O-sulfate-2,5,-anhydromannitol 3,6-O-sulfate; L-iduronic acid-2,5-anhydromannitol 3,6-O-sulfate; L-iduronic acid-2,5-anhydromannitol 3-O-sulfate; D-glucuronic acid-2,5-anhydromannitol 3-O-sulfate; $\Delta^{4,5}$-uronic acid-glucosamine N,3-disulfate; and $\Delta^{4,5}$-uronic acid-glucosamine N-sulfate-iduronic acid 2-sulfate-glucosamine 3,6-disulfate.

The construct can further comprise a vector selected from the group consisting of a plasmid vector or a viral vector. Optionally, the construct can comprise a liposome complex. The heparan sulfate 3-O-sulfotransferase 5 gene product can comprise a protein having an amino acid sequence as set forth in SEQ ID NO 2. The nucleic acid sequence can be selected from the group consisting of: a DNA acid sequence as set forth in SEQ ID NO 1, or its complementary strands; a DNA sequence which hybridizes to a nucleic acid sequence as set forth in SEQ ID NO 1 under wash stringency conditions represented by a wash solution having about 200 mM salt concentration and a wash temperature of at least about 45° C., and which encodes a heparan sulfate 3-O-sulfotransferase 5 polypeptide; and a DNA sequence differing from an isolated nucleic acid molecule above due to degeneracy of the genetic code, and which encodes a heparan sulfate 3-O-sulfotransferase 5 polypeptide encoded by the isolated nucleic acid molecule above.

A method for increasing the efficacy of treating a disorder using a virus vector for delivering therapeutic nucleic acid molecules to the cells of a subject is also provided, comprising administering to the subject a construct comprising a nucleic acid sequence encoding a heparan sulfate 3-O-sulfotransferase 5 gene product operatively linked to a promoter prior to administration of the virus vector, wherein production of the heparan sulfate 3-O-sulfotransferase 5 gene product in the cells results in increased expression of 3-O-sulfated heparan sulfate, and wherein the 3-O-sulfated heparan sulfate is an entry receptor for the virus vector. Optionally, the 3-O-sulfated heparan sulfate comprises a disaccharide selected from the group consisting of: L-iduronic acid 2-O-sulfate-2,5,-anhydromannitol 3-O-sulfate; D-glucuronic acid-2,5,-anhydromannitol 3,6-O-sulfate; L-iduronic acid 2-O-sulfate-2,5,-anhydromannitol 3,6-O-sulfate; L-iduronic acid-2,5-anhydromannitol 3,6-O-sulfate; L-iduronic acid-2,5-anhydromannitol 3-O-sulfate; D-glucuronic acid-2,5-anhydromannitol 3-O-sulfate; $\Delta^{4,5}$-uronic acid-glucosamine N,3-disulfate; and $\Delta^{4,5}$-uronic acid-glucosamine N-sulfate-iduronic acid 2-sulfate-glucosamine 3,6-disulfate.

The construct can further comprise a vector selected from the group consisting of a plasmid vector or a viral vector. Optionally, the construct can comprise a liposome complex. The heparan sulfate 3-O-sulfotransferase 5 gene product can comprise a protein having an amino acid sequence as set forth in SEQ ID NO 2. The nucleic acid sequence can be selected from the group consisting of: a DNA acid sequence as set forth in SEQ ID NO 1, or its complementary strands; a DNA sequence which hybridizes to a nucleic acid sequence as set forth in SEQ ID NO 1 under wash stringency conditions represented by a wash solution having about 200 mM salt concentration and a wash temperature of at least about 45° C., and which encodes a heparan sulfate 3-O-sulfotransferase 5 polypeptide; and a DNA sequence differing from an isolated nucleic acid molecule above due to degeneracy of the genetic code, and which encodes a heparan sulfate 3-O-sulfotransferase 5 polypeptide encoded by the isolated nucleic acid molecule above.

Insofar as a modulator of 3-O-sulfotransferase activity can take the form of a polypeptide or of an anti-3-O-sulfotransferase monoclonal antibody or fragment thereof, it is to be appreciated that the potency can vary, and therefore a "therapeutically effective" amount can vary. However, as shown by the present assay methods, one skilled in the art can readily assess the potency and efficacy of a candidate 3-OST-5 biological activity modulator and adjust the therapeutic regimen accordingly. A modulator of 3-O-sulfotransferase biological activity can be evaluated by a variety of approaches including through the use of a responsive reporter, which drives expression of a reporter gene; interaction of 3-OST-5 polypeptides with a monoclonal antibody as described herein; and other assays known in the art and described herein.

The modulator can be administered parenterally by injection or by gradual infusion over time. Although the tissue to be treated can typically be accessed in the body by systemic administration and therefore most often treated by intravenous administration of therapeutic compositions, other tissues and delivery approaches are contemplated where there is a likelihood that the tissue targeted contains the target molecule and are known to those of skill in the art. The compositions are formulated in an appropriate manner and administered in a manner compatible with the dosage formulation.

VI.B. Monoclonal Antibodies

In one embodiment, 3-OST-5 modulators in the form of monoclonal antibodies which are elicited in response to 3-OST-5 but which can immunoreact with any 3-OST-5 polypeptide, or with a specific isoform of a 3-OST-5 polypeptide, and bind the 3-OST-5 polypeptide to modulate biological activity are provided. Also disclosed are cell lines that produce the antibodies, methods for producing the cell lines, and methods for producing the monoclonal antibodies.

The term "antibody" or "antibody molecule" refers collectively to a population of immunoglobulin molecules and/or immunologically active portions of immunoglobulin molecules, i.e., molecules that contain a paratope. A paratope is the portion or portions of antibodies that is or are responsible for that antibody binding to an antigenic determinant, or epitope.

Representative antibodies for use in the present invention are intact immunoglobulin molecules, substantially intact immunoglobulin molecules, single chain immunoglobulins or antibodies, those portions of an immunoglobulin molecule that contain the paratope, including antibody fragments. A monovalent modulator can optionally be used. Thus, the terms "modulate", "modulating", and "modulator" are intended to encompass such a mechanism.

The term "monoclonal antibody" refers to a population of antibody molecules that contain only one species of paratope and thus typically display a single binding affinity for any particular epitope with which it immunoreacts; a monoclonal antibody can have a plurality of antibody combining sites, each immunospecific for a different epitope, e.g., a bispecific monoclonal antibody. Methods of producing a monoclonal antibody, a hybridoma cell, or a hybridoma cell culture are described above.

It is also possible to determine, without undue experimentation, if a monoclonal antibody has the same or equivalent specificity or immunoreaction characteristics as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. "CDRs" (complementarity-determining regions) mean the three subregions of the light or heavy chain variable regions that have hypervariable sequences and form loop structures that are primarily responsible for making direct contact with antigen. Antibody molecules having identical, or functionally equivalent, amino acid residue sequences in their CDR regions have the same binding specificity. Methods for sequencing polypeptides are well known in the art. Further, other ways of determining whether antibodies have similar immunospecificities are known in the art and can be used.

The immunospecificity of an antibody, its target molecule binding capacity, and the attendant affinity the antibody exhibits for the epitope are defined by the epitope with which the antibody immunoreacts. The epitope specificity is defined at least in part by the amino acid residue sequence of the variable region of the heavy chain of the immunoglobulin that comprises the antibody, and in part by the light-chain-variable-region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule.

Humanized monoclonal antibodies offer particular advantages over monoclonal antibodies derived from other mammals, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention.

The use of a molecular cloning approach to generate antibodies, particularly monoclonal antibodies, and more particularly single chain monoclonal antibodies, is also provided. The production of single chain antibodies has been described in the art, see e.g., U.S. Pat. No. 5,260,203, the contents of which are herein incorporated by reference. For this approach, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by hours and L chain combination in a single chain, which further increases the chance of finding appropriate antibodies. Thus, an antibody, or a "derivative" of an antibody, pertains to a single polypeptide chain binding molecule which has binding specificity and affinity substantially similar to the binding specificity and affinity of the light and heavy chain aggregate variable region of an antibody described herein.

VI.C. Other Modulators

Given the disclosure of the 3-OST-5 activity in tissues herein, chemical compounds (e.g., small molecule mimetics) can be used to modulate 3-OST-5 activity in tissues in accordance with the disclosed methods. The identification of such compounds is facilitated by the description of screening assays directed to 3-OST-5 activity in tissues presented above.

VI.D. Gene Therapy

3-OST-5 genes can be used for gene therapy. Exemplary gene therapy methods, including liposomal transfection of nucleic acids into host cells, are described in U.S. Pat. Nos. 5,279,833; 5,286,634; 5,399,346; 5,646,008; 5,651,964; 5,641,484; and 5,643,567, the contents of each of which are herein incorporated by reference.

Briefly, gene therapy directed toward modulation of 3-OST-5 levels, to thereby affect or modulate the biological activity of 3-OST-5 in a target cell is described. This modulation can affect cell growth and differentiation. In one embodiment, a therapeutic method of the present invention provides a process for modulation of 3-OST-5 levels comprising the steps of: (a) delivering to the cell an effective amount of a vector comprising a polynucleotide that encodes a polypeptide that modulates the biological activity of 3-OST-5; and (b) maintaining the cell under conditions sufficient for expression of the polypeptide.

In a preferred embodiment, the delivered polynucleotide comprises the sequence of SEQ ID NO 1. Delivery can be accomplished by injecting the DNA molecule into the cell. Where the cell is in a subject, administering comprises the steps of: (a) providing a vehicle that contains the DNA molecule; and (b) administering the vehicle to the subject.

A vehicle is preferably a cell transformed or transfected with the DNA molecule or a transfected cell derived from such a transformed or transfected cell. An exemplary transformed or transfected cell is a lymphocyte or a cell from the tissue being treated. Approaches for transforming or transfecting a cell with a DNA molecule are set forth herein.

Alternatively, the vehicle is a virus or an antibody that specifically infects or immunoreacts with an antigen of the target tissue. An advantage of a viral infection system is that it allows for a very high level of infection into the appropriate recipient cell. Also, antibodies have been used to target and deliver DNA molecules.

It is also envisioned that this embodiment of the present invention can be practiced using alternative viral or phage vectors, including retroviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

VI.E. Method of Modulating In vivo 3-OST-5 Levels in the Treatment of Related Diseases and Disorders A method for transcriptionally modulating in a multicellular organism the expression of a gene encoding a 3-OST-5 to modulate 3-OST-5 biological activity in a warm-blooded vertebrate subject is also provided. This method comprises administering to the warm-blooded vertebrate subject a compound at a concentration effective to transcriptionally modulate expression of 3-OST-5.

The compound can optionally comprise an antibody or polypeptide prepared as described above and which transcriptionally modulates expression of 3-OST-5s. Optionally, the antibody or polypeptide directly binds to DNA or RNA, or directly binds to a protein involved in transcription.

Representative chemical entities (e.g., small molecule mimetics) do not naturally occur in any cell, whether of a multicellular or a unicellular organism. Even more particularly, the chemical entity is not a naturally occurring molecule, e.g., it is a chemically synthesized entity. Optionally, the compound can bind a modulatable transcription sequence of the gene. For example, the compound can bind a promoter region upstream of a nucleic acid sequence encoding 3-OST-5 as well as other 3-OST-5s.

In the methods above, modulation of transcription results in either upregulation or downregulation of expression of the gene encoding the protein of interest, depending on the identity of the molecule which contacts the cell.

VI.F. Antisense Oligonucleotide Therapy

Expression of a 3-OST-5 can be modulated in a vertebrate subject through the administration of an antisense oligonucleotide derived from a nucleic acid molecule encoding a 3-OST-5, such as described in SEQ ID NO 1. Therapeutic methods utilizing antisense oligonucleotides have been described in the art, for example, in U.S. Pat. Nos. 5,627,158 and 5,734,033, the contents of each of which are herein incorporated by reference.

VI.G. Dosages

As used herein, an "effective" dose refers to one that is administered in doses tailored to a tissue and/or a patient sufficient to modulate (i.e. inhibit or promote) one or more 3-O-sulfotransferase biological activities. After review of the present disclosure, one of ordinary skill in the art can tailor the dosages to an individual patient, taking into account the particular formulation and method of administration to be used with the composition as well as patient height, weight, severity of symptoms, tissue to be treated, and/or stage of the disorder to be treated.

An effective dose and a therapeutically effective dose are generally synonymous. However, compounds can be administered to patients having reduced symptoms or even administered to patients as a preventative measure. Hence, the composition can be effective in therapeutic treatment even in the absence of symptoms of the disorder, i.e. a prophyllatic treatment.

A unit dose can be administered, for example, 1 to 4 times per day. Most preferably, the unit dose is administered twice a day (BID). The dose depends on the route of administration and the formulation of a composition containing the compound or compounds. Further, it will be appreciated by one of ordinary skill in the art after receiving the present disclosure that it can be necessary to make routine adjustments or variations to the dosage depending on the combination of agents employed, on the age and weight of the patient, and on the severity of the condition to be treated.

Such adjustments or variations, as well as evaluation of when and how to make such adjustments or variations, are well known to those of ordinary skill in the art of medicine. Evaluation parameters and techniques can vary with the patient and the severity of the disease.

VI.H. Formulation of Therapeutic Compositions

The 3-O-sulfotransferase biological activity modulating substances, gene therapy vectors, and substances that inhibit or promote expression of a 3-OST-5 encoding nucleic acid segment described above are adapted for administration as a pharmaceutical compositions as described above. Additional formulation and dose preparation techniques have been described in the art, see for example, those described in U.S. Pat. No. 5,326,902 issued to Seipp et al. on Jul. 5, 1994, U.S. Pat. No. 5,234,933 issued to Marnett et al. on Aug. 10, 1993, and International Publication Number WO 93/25521 of Johnson et al. published Dec. 23, 1993, the entire contents of each of which are herein incorporated by reference.

For the purposes described above, the identified substances can normally be administered systemically or partially, usually by oral or parenteral administration. The doses to be administered are determined depending upon age, body weight, symptom, the desired therapeutic effect, the route of administration, and the duration of the treatment, etc.; one of skill in the art of therapeutic treatment will recognize appropriate procedures and techniques for determining the appropriate dosage regimen for effective therapy. Various compositions and forms of administration are contemplated and are generally known in the art. Other compositions for administration include liquids for external use, and endermic linaments (ointment, etc.), suppositories and pessaries that comprise one or more of the active substance(s) and can be prepared by known methods.

Thus, provided are pharmaceutical compositions comprising a polypeptide, polynucleotide, or molecule or compound as disclosed herein and a physiologically acceptable carrier. For example, a pharmaceutical composition can comprise a compound discovered via the screening methods described herein below.

A composition is typically administered parenterally in dosage unit formulations containing standard, well-known nontoxic physiologically acceptable carriers, adjuvants, and vehicles as desired. The term "parenteral" as used herein includes intravenous, intra-muscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Representative carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A representative approach for purifying the vector involves the use of buoyant density gradients, such as cesium chloride gradient centrifugation.

A transfected cell can also serve as a carrier. By way of example, a liver cell can be removed from an organism, transfected with a polynucleotide disclosed herein using methods set forth above and then the transfected cell returned to the organism (e.g., injected intra-vascularly).

EXAMPLES

The following Examples have been included to illustrate modes of the presently disclosed subject matter. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the present disclosure.

Materials Employed in Examples

Recombinant human 3-OST-3A and mouse 3-OST-1 enzymes were expressed in Sf9 cells using a baculovirus expression system. The enzymes were purified by heparin-Toyopearl and 3',5'-ADP-agarose chromatographies as described by Liu, J., et al., (1999) *J. Biol. Chem.* 274:38155-38162 and Hernaiz, M., et al., (2000) *Biochem. Biophys. Res. Commun.* 276:292-297. [$^{35}$S]PAPS was prepared by incubating 0.4 to 2 mCi/ml [$^{35}$S]Na$_2$SO$_4$ (carrier-free, ICN) and 16 mM ATP with 5 mg/ml dialyzed yeast extract (Sigma Chemical Company, St. Louis, Mo., United States of America) (Liu, J., et al. (1996) *J. Biol. Chem.* 271:27072-27082). HS was either isolated from 33-cells, an L-cell variant, or from Chinese hamster ovary (CHO) cells as described by Liu, J., et al. (1996) *J. Biol. Chem.* 271:27072-27082. The concentrations of the unlabeled HS were determined by a method reported by Bjornsson, S. (1993) *Anal. Biochem.* 210:282-291.

Preparation of metabolically $^{35}$S-labeled HS from CHO cells was as described by Zhang, L., Yoshida, K., Liu, J., and Rosenberg, R. D. (1999) *J. Biol. Chem.* 274:5681-5691. Human AT is from Cutter Biological (Berkeley, Calif.). A truncated form of HSV-1, glycoprotein D, gD-1 (306t), and monoclonal anti-gD (DL6) were generous gifts of Drs. Cohen and Eisenberg of the University of Pennsylvania (Nicola, A. V., et al., (1996) *J. Virol.* 70:3815-3822). The $^3$H-labeled disaccharide standards, GlcUA—AnMan3S6S and IdoUA2S—AnMan6S, were prepared from $^3$H-labeled HS (gifts from Dr. Rosenberg, Massachusetts Institute of Technology; Shworak, N. W., et al., (1994) *J. Biol. Chem.* 269: 24941-24952). The $^{35}$S-labeled disaccharide standards, IdoUA2S—AnMan3S and IdoUA2S—AnMan3S6S, were prepared from low pH (pH 1.5) nitrous acid-degraded HS that was modified by purified 3-OST-3 enzyme as described by Liu, J., et al., (1999) *J. Biol. Chem.* 274:38155-38162.

Example 1

Isolation of the cDNA Encoding 3-OST-5

GENBANK™ database was probed with the amino acid sequence of 3-OST-1 using tBlastn. By using Genscan (Burge, C. and Karlin, S. (1997) *J. Mol. Biol.* 268:78-94), a 1,041-bp open reading frame that encodes a homologous protein from a genomic clone RP11-112L15 with GENBANK™ accession number AL355498 was predicted. The open reading frame sequence, designated as 3-OST-5, was located in two exons. Both 5'- and 3'-primers were synthesized based upon the sequence of exon 1 and exon 2, respectively. The following are the sequences of the two specific primers: 5'- GGAGGGCC ATG CTA TTC AAA CAG-3' (5'-primer) (SEQ ID NO 6), and 5'-TTA GGG CCA GTT CAA TGT CCT-3' (3'-primer) (SEQ ID NO 7). The cDNA was cloned from a human placenta cDNA library using PCR with the two specific primers. The resultant PCR product (about 1.0 kb) was inserted into the pGEM-T-easy vector (pGEM-T-3OST5) and sequenced for both strands. The isolated cDNA had an identical sequence that was predicted from the genomic clone.

Both COS-7 and wild type CHO cells were from Dr. R. Jude Samulski (University of North Carolina). COS-7 cells and CHO cells were maintained in logarithmic growth by subculturing biweekly at 37° C. under 6% CO$_2$ humidified atmosphere. COS-7 cells and CHO cells were grown in Dulbecco's modified Eagle's medium (Invitrogen Corporation, Carlsbad, Calif., United States of America) and in F-12 medium (Invitrogen Corporation, Carlsbad, Calif., United States of America) supplemented with 10% fetal bovine serum (JRH Biosciences), respectively.

3-OST-5 expression plasmid was constructed by inserting the open reading frame of 3-OST-5 into a pcDNA3.1 (Invitrogen Corporation, Carlsbad, Calif., United States of America) expression vector. The open reading 20 frame was obtained by reamplifying the sequence from pGEM-T-3OST5 by PCR using the following primers: 1) the 5'-specific primer, 5'-TCA AAGCTT GCCACCATG CTATTCAAA-CAGCA-3' (SEQ ID NO 8), contains an HindIII site (underlined), the consensus Kozak sequence (italicized) and a start codon; and 2) the 3'-specific primer, 5'-GC TCTAGA TTAGGGCCAGTTCAATGTCCT-3' (SEQ ID NO 9), contains an XbaI site (underlined). PCRs were carried out using Advantage-2 PCR kit (Clontech, Palo Alto, Calif., United States of America) with the initial denaturation for 2 min at 94° C., followed by 30 cycles of a reaction as follows: 45 seconds (s) for denaturation at 94° C., 45 s for annealing at 62° C., and 90 s for elongation at 72° C. The PCR fragment was subcloned into pcDNA3.1 (Invitrogen Corporation, Carlsbad, Calif., United States of America) using HindIII/XbaI sites. The coding region of the construct was completely sequenced on both strands, and the construct was designated pcDNA3.1-3OST5. pcDNA3.1-3OST5 or pcDNA3 plasmid was transfected into exponentially growing COS-7 cells using LipofectAMINE 2000 (Invitrogen Corporation, Carlsbad, Calif., United States of America).

Probing the non-redundant database of National Center for Biotechnology Information (NCBI) with the deduced amino acid sequence of human 3-OST-1 (accession number AF033827), we identified a 165-kb genomic clone with GENBANK™ accession number AL355498. An open reading frame was found to be 1041 bp. The predicted open reading frame was located in two exons that were gapped by a 4.5-kb intron. The open reading frame of this protein, assigned as 3-OST-5, was amplified from a human placenta cDNA library using specific 5'- and 3'-primers as described herein above. Embodiments of the 3-OST-5 cDNA sequence and amino acid sequence are shown in FIG. 1.

The 3-OST-5 peptide of 346 amino acid residues predicts a type II membrane-bound protein. The protein has four potential N-glycosylation sites with the predicted molecular mass of 40,407 Da. The amino acid sequence of 3-OST-5 has 71 and 58% homology to 3-OST-1 and 3-OST-3 in the sulfotransferase domains, respectively (FIG. 2). Putative PAPS-binding sites were also found in 3-OST-5 based upon the PAPS-binding consensus sequences (Negishi, M., et al., (2001) *Arch. Biochem. Biophys.* 390:149-157; Shworak, N. W., et al., (1999) *J. Biol. Chem.* 274:5170-5184) (FIG. 2). The genomic BAC clone RP11-112L15, which contains 3-OST-5 gene, was annotated to be mapped on human chromosome 6q22.1. Alignment of the genomic sequence with 3-OST-5 cDNA revealed that exon 1 and exon 2 contain 107 and 934 bp of the open reading frame, respectively.

Example 2

Determination of the $^{35}$S-Labeled Sulfation Site of 3-OST-5-modified HS

The crude HS enzyme was extracted from transfected COS-7 cells. The cells were harvested 72 hours (h) after transfection. Approximately 3×10$^6$ cells were mixed with 100 µl of cold 0.25 M sucrose containing 1% TRITON® X-100 (v/v) and incubated on ice for 30 min. The insoluble residues were removed after centrifuging at 10,000×g for 10 min. The HS sulfotransferase activity was determined by incubating 40 µg of cell extract with 1 µg of unlabeled HS (from 33-cells), 4×10$^7$ cpm of [$^{35}$S]PAPS, in 50 µl of a buffer containing 50 mM 2-(N-morphilino)ethanesulfonic acid (MES), 10 mM MnCl$_2$, 5 mM MgCl$_2$ and 1% TRITON® X-100 (pH 7). The reaction was incubated at 37° C. for 2 h, quenched by heating at 100° C. for 1 minute (min), and centrifuged at 10,000×g for 1 min to remove insoluble materials. The sample was then subjected to a 200-µl diethylaminoethyl (DEAE)-Sepharose column to purify [$^{35}$S]HS (Liu, J., et al., (1996) *J. Biol. Chem.* 271:27072-27082).

The [$^{35}$S]HS modified by 3-OST-5 was mixed with 20 µg of unlabeled HS (from ICN) and degraded with nitrous acid at pH 1.5 followed by reduction with sodium borohydride (Shively, J. E., and Conrad, H. E. (1976) *Biochemistry* 15:3932-3942). The resultant $^{35}$S-labeled disaccharides were mixed with a $^3$H-labeled disaccharide standard, IdoUA2S-[1-$^3$H]AnMan6S, and desalted on a Bio-Gel P-2 column (0.75×200 cm) that was equilibrated with 0.1 M ammonium bicarbonate at a flow rate of 4 ml/h. The $^3$H-labeled disaccharide standard was used to locate the elution position of the disaccharides from the Bio-Gel P-2 column.

The disaccharides were resolved by a C$_{18}$-reversed phase column (0.46×25 cm) (GraceVydac, Conn., United States of America) under the reverse-phase ion-pairing HPLC (RPIP-HPLC) condition (Liu, J., et al., (1999) *J. Biol. Chem.* 274:38155-38162). Briefly, the column was eluted with acetonitrile as follows: 8% for 30 min followed by 15% for 15 min and followed by 19.5%, in a solution containing 38 mM ammonium phosphate monobasic, 2 mM phosphoric acid, and 1 mM tetrabutylammonium phosphate monobasic (Fluka, Switzerland) at a flow rate of 0.5 ml/min.

To prepare 3-OST-3-modified HS, HS (1 µg from 33-cells) was mixed with 30 ng of purified 3-OST-3A enzyme and [$^{35}$S]PAPS (4×10$^7$ cpm) in a buffer containing 50 mM MES, 1% TRITON® X-100, 1 mM MgCl$_2$, 2 mM MnCl$_2$, 150 mM NaCl, and 168 µg/ml bovine serum albumin (pH 7), in a final volume of 50 µl. The reaction was incubated at 37° C. for 2 h and was then heated at 100° C. for 2 min. The resultant product was centrifuged at 14,000 rpm for 1 min to remove insoluble materials. The supernatant was loaded onto a 200 µl DEAE-Sepharose column, and the [$^{35}$S]HS was eluted from the column with 1000 mM NaCl (Liu, J., et al. (1996) *J. Biol. Chem.* 271:27072-27082). To prepare 3-OST-1-modified HS, 70 ng of purified enzyme were utilized nearly identical procedures were followed except for omitting the 150 mM NaCl.

Because the cloned 3-OST-5 has high homology to 3-OST-1 and 3-OST-3 the hypothesis for 3-OST activity was tested. The plasmid expressing 3-OST-5 was transiently transfected into exponentially growing COS-7 cells. The cells were solubilized with detergent. HS sulfotransferase activity was determined by incubating with unlabeled HS and [$^{35}$S] PAPS as described herein above. The resultant [$^{35}$S]HS was subjected to nitrous acid degradation at pH 1.5 followed by sodium borohydride reduction to prepare $^{35}$S-labeled disaccharides. This approach has been employed to successfully characterize the sulfation sites of 3-OST-2 and 3-OST-3. Liu, J., et al. (1999) *J. Biol. Chem.* 274:5185-5192; Shukla, D., et al., (1999) *Cell* 99:13-22).

The $^{35}$S-labeled disaccharides were resolved on RPIP-HPLC, and the chromatograms are shown in FIGS. 3A and 3B. Comparing the profiles of the degraded [$^{35}$S]HS that was modified by pcDNA3-transfected cells (FIG. 3A), additional $^{35}$S-labeled disaccharides in the 3-OST-5-modified HS (FIG. 3B) were found. By co-eluting with the appropriate disaccharide standards on RPIP-HPLC, three of the $^{35}$S-labeled disaccharides were 3-O-sulfated disaccharides with the structures of IdoUA2S-AnMan3S (eluted at 38.5 min), GlcUA-AnMan3S6S (eluted at 55.5 min), and IdoUA2S-AnMan3S6S (eluted at 70.3 min). A small peak of $^{35}$S-labeled disaccharide with a structure of IdoUA2S—AnMan6S was also observed (eluted at 59.6 min). The IdoUA2S—AnMan6S was observed in HS modified with pcDNA3-transfected COS-7 cells, although the level of this disaccharide varied between experiments. The presence of IdoUA2S—AnMan6S, which is a common disaccharide in HS, was unlikely to be associated with the activity of 3-OST-5. A minor $^{35}$S-labeled peak at 48 min was also detected. The identity of this $^{35}$S-labeled peak was unknown. Taken together, these results indicate that the expressed 3-OST-5 has 3-OST activity. It is important to note that IdoUA2S-AnMan3S and IdoUA2S-AnMan3S6S are characteristic disaccharides of 3-OST-3-modified HS (Shukla, D., et al., (1999) Cell 99:13-22), whereas GlcUA—AnMan3S6S is a characteristic disaccharide of 3-OST-1-modified HS (Liu, J., et al. (1996) J. Biol. Chem. 271:27072-27082).

Example 3

The Activity of 3-OST-5 in Assisting HSV-1 Entry

Conditions for growing cells and different HSV strains are described by Shukla, D., et al., (1999) Cell 99:13-22. The viral infectivity assay is based on visualization of the cells carrying β-galactosidase activity (Shworak, N. W., et al., (1994) J. Biol. Chem. 269:24941-24952). CHO cells were transfected in 6-well dishes, using LipofectAMINE (Invitrogen Corporation, Carlsbad, Calif., United States of America) with pcDNA3.1-3OST5 plasmid or control plasmid (pcDNA3) at 1.5-2.0 µg per well in 1 ml. At about 36 h post-transfection, cells were exposed to recombinant HSV-1 (HSV-1 (KOS)gL86) (a gift from Dr. Spear, Northwestern University, Chicago, Ill., United States of America) that expresses β-galactosidase upon viral entry. At 6 h post-infection, the cells were fixed in phosphate-buffered saline (PBS) containing 2% formaldehyde and 0.2% glutaraldehyde, permeabilized in 2 mM $MgCl_2$ containing 0.01% deoxycholate and 0.02% Nonidet P-40, and incubated with buffered X-gal (0.5 mg/ml). Three hours later the infected cells were visible in blue due to the action of β-galactosidase on X-gal. The transfection efficiency for CHO cells was determined by transfecting a plasmid expressing β-galactosidase as a reporter gene.

The assay for determining the binding of 3-O-sulfated HS to gD was carried out by an immunoprecipitation procedure using anti-gD monoclonal antibody (Shukla, D., et al., (1999) Cell 99:13-22). The enzyme-modified HS (100,000-200,000 cpm) was incubated in 50 µl of a buffer containing 50 mM Tris-HCl, 150 mM NaCl, and 0.01% TRITON® (pH 7) (binding buffer), and 2 mg/ml of gD at room temperature for 30 min. The anti-gD monoclonal antibody DL6 (5 µl) was added and incubated at 4° C. for 1 h followed by the addition of protein A-agarose gel (80 µl of 1:1 slurry) and agitated at 4° C. for an additional hour. The HS was eluted from the gel with 1 ml of 1000 mM NaCl in the binding buffer.

Shukla, D., et al., (1999) Cell 99:13-22 demonstrated that 3-OST-3-modified HS serves as a receptor for HSV-1, entry. Because the disaccharides of 3-OST-3-modified HS were detected as noted in Example 2, it was tested whether 3-OST-5-modified HS generates an entry receptor for HSV-1 using an approach that was previously published by Shukla, D., et al., (1999) Cell 99:13-22. A recombinant β-galactosidase-expressing HSV-1 strain (HSV-1(KOS)gL86) was used for the entry assay. This recombinant virus expresses β-galactosidase from an insert in the viral genome immediately upon entry into cells. As shown in FIG. 4A, the mock-transfected CHO cells are resistant to HSV-1 entry (no dark cells) as reported by Shieh, M.-T. et al., (1992) J. Cell Biol. 116:1273-1281. In contrast, a significant number of CHO cells transfected with pcDNA3.1-3OST5 were rendered susceptible (FIG. 4B, dark cells) to the entry of HSV-1. It was estimated that about 20% of the cells were susceptible to HSV-1 infection, which coincided with the transfection efficiency. In separate sets of experiments, it was found that 3-OST-5-modified HS does not generate receptors for other alphaherpesviruses. The viruses examined for entry via 3-OST-5-modified HS included wild type HSV-2, HSV-1 Rid mutants (Nicola, A. V. et al., (1996) J. Virol. 70:3815-3822), bovine herpesvirus, and pseudorabies virus.

Furthermore, it was examined whether 3-OST-5-modified HS bound to gD. The results showed that 3-OST-5-modified HS has about a 2-fold increase in the binding to gD compared with the control, suggesting that 3-OST-5-modified HS generates gD-binding sites (Table 3). It was noted that the gD-binding percentage of 3-OST-5-modified HS (9.0%) was less than that of 3-OST-3-modified HS (23.1%). Such deviation is likely due to the fact the 3-OST-5 enzyme was in a mixture containing other HS sulfotransferases, whereas purified 3-OST-3A enzyme was employed to prepare 3-OST-3-modified HS. Taken together, the results set forth in this Example indicate that 3-OST-5 is capable of assisting the entry of HSV-1 by generating a receptor for gD. In addition, it is apparent that the mechanism for 3-OST-5-assisted HSV-1 infection is very similar to what was previously characterized for 3-OST-3. However, it was concluded whether or not the saccharide sequences of the gD-binding site in 3-OST-5-modified HS and the sequence in 3-OST-3A-modified HS were identical.

Example 4

Demonstration of 3-OST-5-modified HS Binding to AT

The binding of the 3-OST-5-modified HS to AT was used as a measure of 3-OST-5-modified HS to provide anticoagulant activity and was determined using an AT/concanavalin A (ConA)-Sepharose approach (Liu, J., et al. (1996) J. Biol. Chem. 271:27072-27082). Briefly, HS (10,000-100,000 cpm) was incubated in 150 µl of a buffer, which contains 10 mM Tris-HCl, 150 mM NaCl, 1 µM dextran sulfate, 1 mM $Ca^{2+}$, $Mg^{2+}$, and $Mn^{2+}$, and 0.1 mg/ml AT (pH 7.5), at room temperature for 30 min. The solution was mixed with the prewashed ConA-Sepharose (60 µl of 1:1 slurry) and agitated at room temperature for 1 h. The gel was then washed with 3×1 ml of a buffer containing 10 mM Tris-HCl, 0.0004% TRITON® X-100, and 150 mM NaCl (pH 7.5). The HS was eluted from the gel by 1 ml of a buffer containing 10 mM Tris-HCl, 1000mM NaCl, and 0.0004% TRITON® X-100 (pH 7.5).

The assay was specifically designed to determine the HS biosynthetic activity that generates $HS^{act}$ (Liu, J., et al. (1996) J. Biol. Chem. 271:27072-27082), which in turn indicates measurable anticoagulant activity. Briefly, cell extract was incubated with metabolically $^{35}$S-labeled nonanticoagulant HS (from wild type CHO cells) and unlabeled PAPS. The resultant [$^{35}$S]HS was subjected to the AT-binding assay as described above. The increase in the percentage of the [$^{35}$S]

HS that binds to AT correlated to the amount of HS$^{act}$ conversion activity in the cell extract.

From the result of the disaccharide analysis of 3-OST-5-modified HS as described above, it was found that 3-OST-5-modified HS also contains GlcUA—AnMan3S6S. This observation prompted an inquiry as to whether or not 3-OST-5-modified HS bound to AT. The results for the binding of [$^{35}$S]HS to AT are shown in Table 3. As expected, 37.0% of 3-OST-1-modified HS bound to AT, whereas only 1.4% of 3-OST-3-modified HS bound to AT. Those results were consistent with the previous reports (Liu, J., et al. (1999) *J. Biol. Chem.* 274:5185-5192; Liu, J., et al. (1996) *J. Biol. Chem.* 271:27072-27082). Comparing the percentages of HS$^{act}$ between 3-OST-5-modified HS and control, it was found that the binding of 3-OST-5-modified HS to AT was 6.3-fold higher than the control sample. The result indicates that 3-OST-5-modified HS binds to AT. The conclusion was further strengthened by the results presented below.

The HS$^{act}$ conversion activity of the cell extract from 3-OST-5-transfected cells was also determined, as this assay was designed to measure the enzymatic activity that generates anticoagulant HS (Liu, J., et al. (1996) *J. Biol. Chem.* 271: 27072-27082). Nonanticoagulant [$^{35}$S]HS (HS$^{inact}$) was incubated with cell extract and unlabeled PAPS. The resultant [$^{35}$S]HS was subjected to AT/ConA-affinity gel. It was found that about 4.8% of the [$^{35}$S]HS bound to AT/ConA-affinity gel after incubation with 3-OST-5-transfected cell extract, whereas only 0.12% of the [$^{35}$S]HS bound to AT/ConA-affinity gel after incubation with the control cell extract (transfected with pcDNA3). These results demonstrated that the HS$^{act}$ conversion activity in 3-OST-5-transfected cells was elevated by 40-fold. The data were consistent with the conclusion that 3-OST-5 has the activity in synthesizing HS$^{act}$.

The composition of the $^{35}$S-labeled disaccharides from 3-OST-5-modified HS$^{act}$ and from 3-OST-5-modified HS$^{inact}$ (nonantithrombin-binding HS) was compared. The HS$^{inact}$ and HS$^{act}$ were separated by the AT/ConA-affinity approach as described herein above. Nearly 35% of 3-OST-5-modified HS$^{act}$ bound to AT-affinity gel (Table 3), suggesting that the fractionation had significantly enriched HS$^{act}$. Both the HS$^{inact}$ and HS$^{act}$ were degraded with nitrous acid at pH 1.5 followed by sodium borohydride reduction, and the resultant $^{35}$S-labeled disaccharides were analyzed by RPIP-HPLC (FIGS. 5A and 5B). As shown in FIG. 5B, $^{35}$S-labeled GlcUA-AnMan3S6S was the major disaccharide in the 3-OST-5-modified HS$^{act}$. It is noted that GlcUA—AnMan3S6S is a characteristic disaccharide of 3-OST-1-modified HS and is part of the AT-binding site (Liu, J., et al. (1996) *J. Biol. Chem.* 271:27072-27082). It was also noted that GlcUA-AnMan3S6S was still observed in HS$^{inact}$. Two possible reasons might contribute to this observation. First, the AT-affinity fractionation was incomplete. Second, it is known that HS$^{inact}$ contains GlcUA—AnMan3S6S (Liu, J., et al. (1996) *J. Biol. Chem.* 271:27072-27082). Taken together, these results demonstrated that 3-OST-5 enzyme generated an AT-binding site, and the HS$^{act}$ contained the disaccharide, GlcUA-AnMan3S6S. In conclusion, these results indicated that 3-OST-5 synthesized both HS$^{act}$, thereby producing anticoagulant benefits, and gD-binding HS.

It is noted that two $^{35}$S-labeled disaccharides, IdoUA2S-AnMan3S and IdoUA2S-AnMan3S6S, were absent in 3-OST-5-modified HS$^{act}$ (FIG. 5B). Those two disaccharides are believed to be parts of the gD-binding site in 3-OST-5-modified HS, which contribute to the activity in assisting HSV-1 entry. The data suggested that 3-OST-5 enzyme sulfates two subpopulations of HS substrates. One population is HS$^{act}$ precursor, which becomes HS$^{act}$ after 3-OST-5 modification. Another population is gD-binding HS precursor, which becomes gD-binding HS after 3-OST-5 modification. This data supported the conclusion that the biosynthesis of HS$^{act}$ is regulated by the availability of the HS$^{act}$ precursors for 3-O-sulfation. See also Table 4.

TABLE 3

The binding of 3-OST-5-modified HS to gD and AT

| | Binding to gD$^a$ (%) | Binding to AT$^b$ (%) |
|---|---|---|
| Control$^c$ | 5.0 ± 0.4 (n = 2) | 0.68 ± 0.24 (n = 4) |
| 3-OST-5 modified HS | 9.0 ± 0.1 (n = 2) | 4.3 ± 1.8 (n = 4) |
| 3-OST-5 modified Hs$^{act d}$ | Not determined | 34.7 (n = 1) |
| 3-OST-1 modified Hs$^e$ | 6.6 ± 0.3 (n = 2) | 37.0 ± 3.3 (n = 4) |
| 3-OST-3 modified Hs$^e$ | 23.1 ± 3 (n = 2) | 1.4 ± 0.7 (n = 4) |

$^a$The binding of the HS and gD was determined by incubating modified [$^{35}$S] HS with gD followed by immunoprecipitation using anti-gD monoclonal antibody (DL6) to precipitate the complex of [$^{35}$S]HS and gD. Data are presented as the mean ± S.D., where n represents the number of determinations.
$^b$The binding of the HS to AT was determined by incubating modified [$^{35}$S] HS and AT by using AT/ConA-Sepharose gel as described under "Experimental Procedures."
$^c$Control was the [$^{35}$S]HS that was prepared by incubating HS with the cell extract transfected with pcDNA3.
$^d$3-OST-5-modified HS$^{act}$ was prepared by AT-affinity fractionation from 3-OST-5-modified HS as described under "Experimental Procedures."
$^e$3-OST-1- and 3-OST-3-modified HS were prepared by incubating unlabeled HS (from 33 cells), [$^{35}$S]PAPS, and purified 3-OST-1 (70 ng) and 3-OST-3 (35 ng), respectively.

TABLE 4

Summary of the products and biological functions of 3-OST isoform-modified HS

| 3-OST isoform | The characteristic disaccharides of enzyme modified HSs | Biological functions of the enzyme modified HS |
|---|---|---|
| 3-OST-1 | GlcUA-AnMan3S ± 6S$^b$ | AT-binding HS |
| 3-OST-2 | GlcUA2S-AnMan3S and IdoUA2S-AnMan3S | Unknown$^c$ |
| 3-OST-3A | IdoUA2S-AnMan3S ± 6S | Entry receptor for HSV-1 |
| 3-OST-3B | IdoUA2S-AnMan3S ± 6S | Entry receptor for HSV-1 |
| 3-OST-4 | Unknown | Unknown$^c$ |
| 3-OST-5 | GlcUA-AnMan3S6S and IdoUA2S-AnMan3S ± 6S | AT-binding HS and entry receptor for HSV-1 |

$^a$The disaccharides were prepared by subjecting the enzyme-modified HS to the degradations of nitrous acid.
$^b$The 3-O-sulfate group is shown in boldface and underlined to emphasize the modification.
$^c$A recent review by Shukla and Spear (Shukla, D., and Spear, P. G. (2001) J. Clin. Invest. 108: 503-510) indicated that 3-OST-2 and 3-OST-4 generate entry receptors for HSV-1.

Example 5

Tissue Distribution of 3-OST-5

The coding sequence of 3-OST-5 was labeled with [$\gamma$-$^{32}$P] dCTP in a reaction with Klenow enzyme (Roche Molecular Biochemicals) and used as a probe to hybridize the Human Multiple Tissue Northern (MTN®) blot (Clontech, Palo Alto, Calif., United States of America). The hybridization was carried out in EXPRESSHYB™ Hybridization Solution (Clontech, Palo Alto, Calif., United States of America) at 60° C. for 1 h, and the blot was washed with 0.1×SSC containing 0.5% SDS at 60° C. for 40 min (where 1×SSC contains 150 mM NaCl and 15 mM sodium citrate, pH 7.0). The membrane was exposed to an x-ray film for 4 days.

Figure 6:
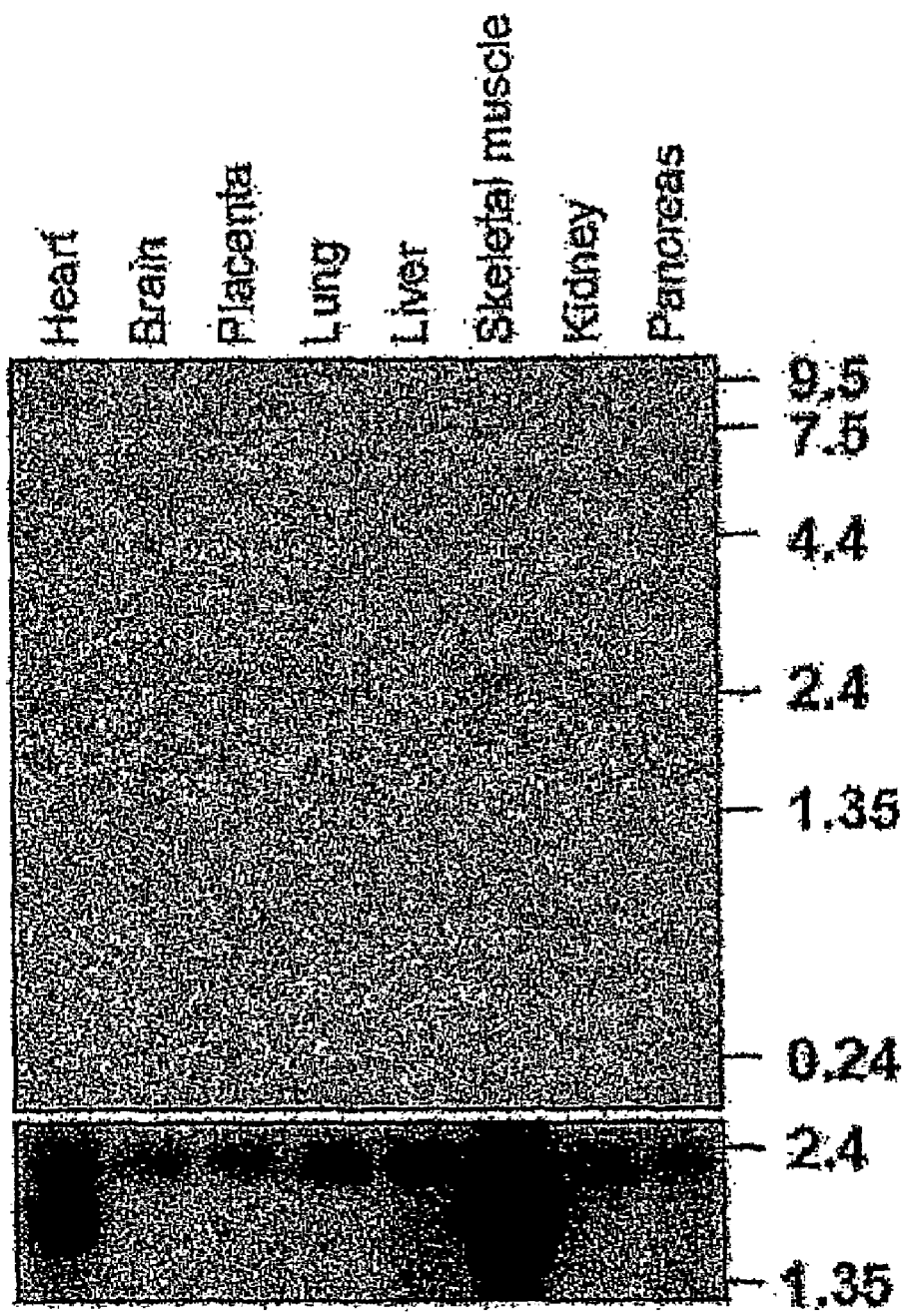
FIG. 6 is an autoradiograph of a Northern blot showing expression of 3-OST mRNA in human tissues. A human multiple tissue Northern blot was hybridized with human 3-OST-5 (upper panel) and β-actin (lower panel) cDNA probes labeled with [$^{32}$P]dCTP under the conditions described in Example 5.

Northern analysis was carried out on a human Northern multiple tissue blot using 3-OST-5 open reading frame as a probe. It appears that 3-OST-5 is predominantly expressed in skeletal muscle with a size of ~2.4 and ~3.8 kb (FIG. 6, top panel). The distribution of 3-OST-5 is distinct from those of 3-OST-1 and 3-OST-3A and 3-OST-3B as reported by Shworak et al., (1999) *J. Biol Chem.* 274:5170-5184.

Example 6

3-OST-5 Enzyme Generates Anticoagulant HS in vivo

Figure 7:
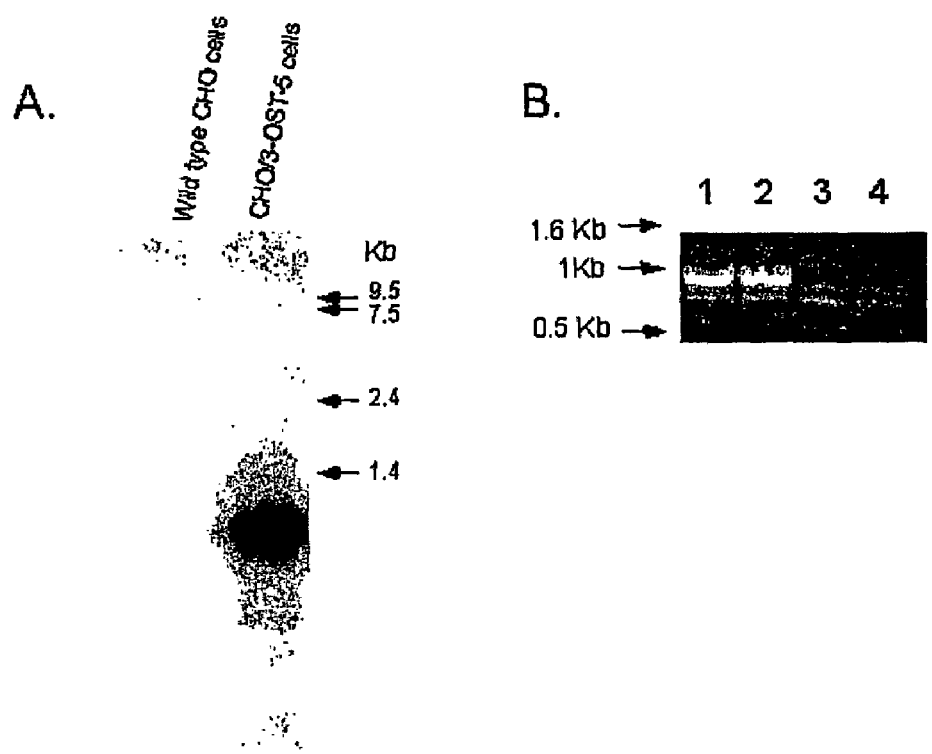
FIGS. 7A and 7B show the determination of the expression of 3-OST-5 in CHO/3-OST-5.

Wild type Chinese Hamster Ovary (CHO) cells do not express HS 3-O-sulfotransferases. Thus, the HS isolated from wild type CHO cells does not contain any 3-O-sulfated glucosamine residues, and does not have anticoagulant activity. To study the role of 3-OST-5 in synthesizing anticoagulant HS in vivo, 3-OST-5 cDNA was introduced into wild type CHO cells to obtain a stable expression of 3-OST-5 (CHO/3-OST-5) in CHO cells. The results of the analyses of 3-OST-5 expression in CHO/3-OST-5 cells are shown in FIGS. 7A and 7B. Using Northern analysis a strong signal was observed at 1.1 Kb, which is very close to the expected size of the message (1.06 Kb), whereas the signal is absent in the mRNA from wild type CHO. In addition, a PCR product was observed at 0.9 Kb, which is identical to the expected size using two 3-OST-5 specific primers, whereas the PCR product is absent in the mRNA from wild type CHO cells. In conclusion, the level of 3-OST-5 is substantially increased in the stable expression cells (CHO/3-OST-5).

HS was isolated from CHO/3-OST-5 cells and determined binding to antithrombin. It was found that 7.2±1.6% (n=7) of the HS from CHO/3-OST-5 binds to antithrombin, whereas, only 0.3±0.1% (n=2) of HS from wild type CHO binds to antithrombin. The result suggested that introducing of 3-OST-5 into CHO cells has elevated the biosynthesis of antithrombin-binding HS by 24-fold.

Figure 8A:
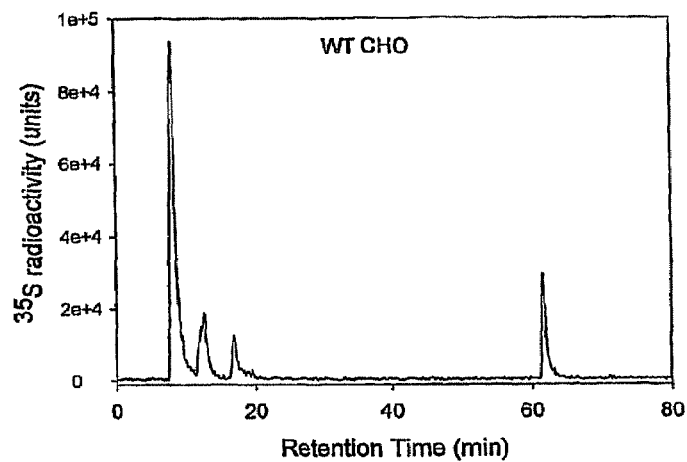
FIGS. 8A and 8B are chromatograms of RPIP-HPLC of disaccharides of the HS from wild type CHO cells and CHO/3-OST-5 cells. The HSs were isolated from the cells grown in the medium containing sodium [$^{35}$S]sulfate. The HS were degraded by nitrous acid at pH 1.5, and the resultant $^{35}$S-labeled disaccharides were isolated.
Figure 8B:
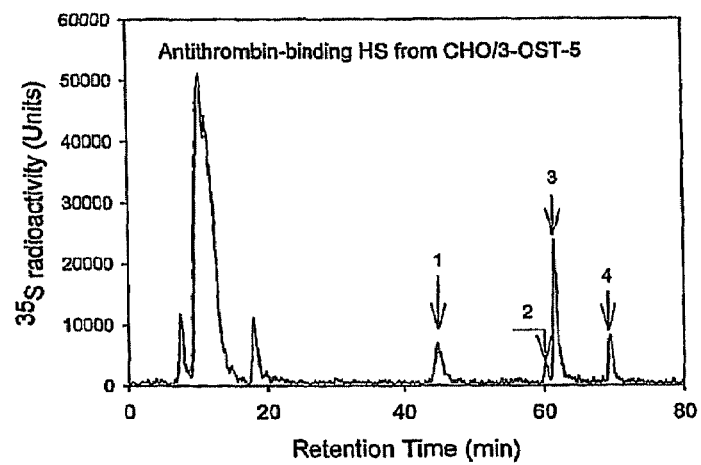

The disaccharide composition of the HS from CHO/3-OST-5 cells and from wild type CHO cells was analyzed. The HPLC chromatograms are shown in FIGS. 8A and 8B. As expected, it was observed the characteristic disaccharides (Disaccharide 1, Disaccharide 2 and Disaccharide 4) of 3-OST-5-modified HS (Xia, G., et al., (2002) *J. Biol. Chem.* 277:37912-37919). The results from the disaccharide analysis strengthened the conclusion that 3-OST-5 is successfully expressed in CHO cells.

The binding affinity of the HS from CHO/3-OST-5 to antithrombin was determined to be 9 nM by using affinity coelectrophoresis. It should be noted that this binding affinity is very similar to binding affinity of 3-OST-1-modified HS and antithrombin (Lee, M. K., and Lander, A. D., (1991) *Proc. Natl. Acad. Sci. USA* 88:2768-2772). These results indicated that 3-OST-5 modified HS has high binding affinity to antithrombin, and therefore can serve as an anticoagulant.

Factor Xa plays a key role in regulating the formation of blood clotting. It is believed that HS or heparin prevents blood from clotting by inhibiting the activity of factor Xa via the interaction with antithrombin. As another measure of anticoagulant activity of 3-OST-5 modified HS, it was investigated whether the binding of the HS from CHO/3-OST-5 cells to antihtrombin inhibits the activity of factor Xa by using a method described by Zhang, L., et al., (2001) *J. Biol. Chem.* 276:42311-42321. The $IC_{50}$ of the HS from CHO/3-OST-5 was found to be 20 µg/ml, whereas no inhibition effect was detected on the activity of factor Xa using the HS from wild type CHO cells at such concentration.

Example 7

Purification of Recombinant 3-OST-5

Figure 9:
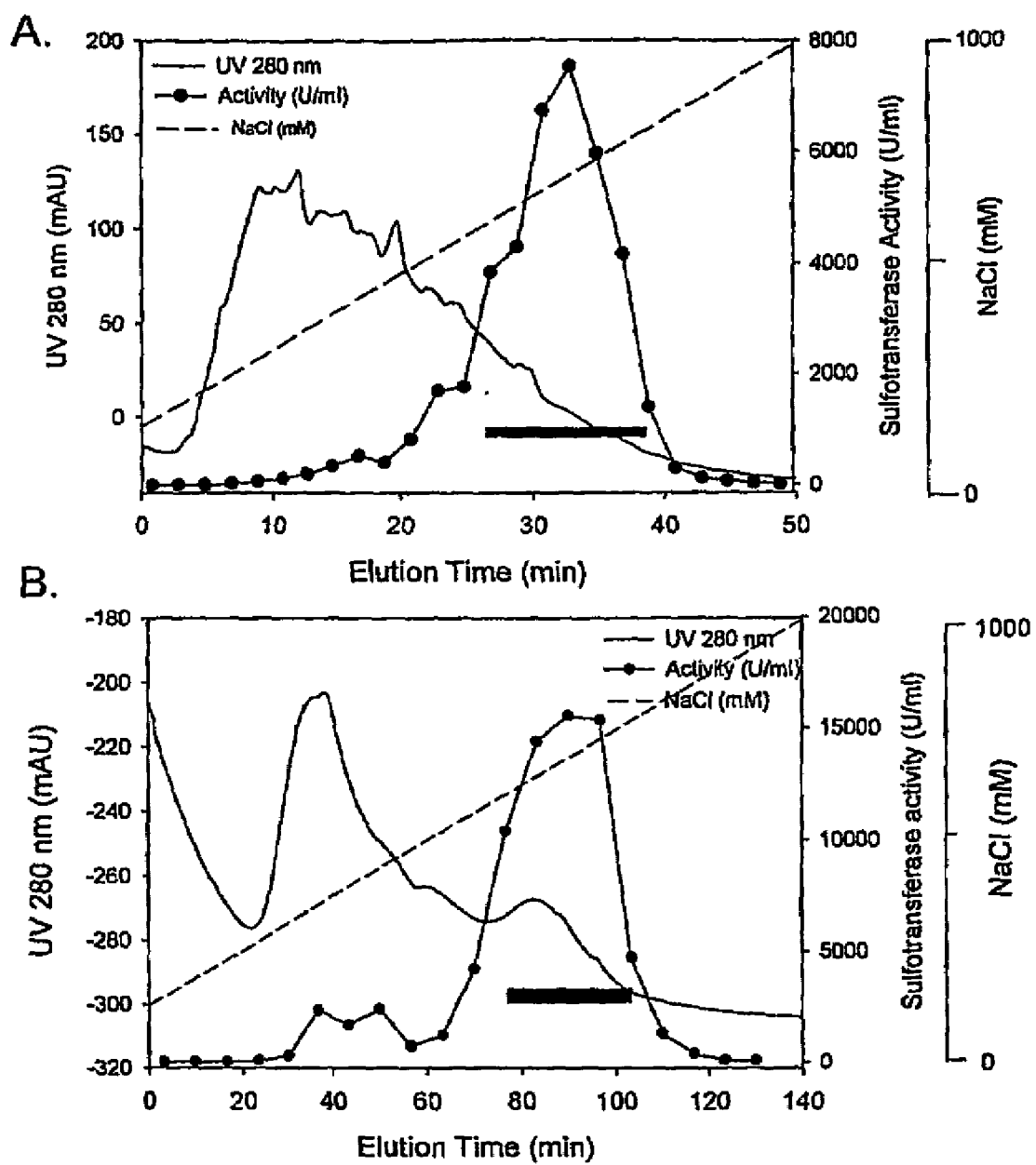
FIGS. 9A and 9B depict the purification of 3-OST-5 by Heparin-SEPHAROSE™ (Amersham Biosciences, Piscataway, N.J., United States of America) and 3',5'-ADP-agarose.

Infection of Sf9 cells with a recombinant 3-OST-5 baculovirus elevated the level of HS sulfotransferase activity by 20-fold in the media, indicating that a 3-OST-5 enzyme was successfully expressed. Both Heparin-SEPHAROSE™ (Amersham Biosciences, Piscataway, N.J., United States of America) and 3',5-ADP (Sigma-Aldrich, St. Louis, Mo., United States of America) chromatographies were employed to purify 3-OST-5. The elution profiles of 3-OST-5 from Heparin-SEPHAROSE™ and 3',5'-ADP-agarose columns are shown in FIGS. 9A and 9B, respectively. From 1,450 ml of media, 560 µg of protein was obtained with 27.0-fold purification and 31.4% recovery yield (Table 5).

TABLE 5

Summary of the purification of 3-OST-5 from SF9 cells media

| Steps | Volume (ml) | Activity ($10^{-5}$ × Units)[a] | Protein (mg) | Specific Activity (×$10^{-3}$ Units/mg) | Purification fold | Recovery (%) |
|---|---|---|---|---|---|---|
| Media | 1450 | 3.5 | 48.2 | 7.3 | — | — |
| Heparin-Sepharose | 48 | 1.7 | 5.2 | 32.7 | 4.5 | 48.6 |
| 3',5'-ADP-agarose | 8 | 1.1 | 0.56 | 196.4 | 27.0 | 31.4 |

[a]One unit is defined as transferring 1 picomole of sulfate to HS substrate in one hour under the standard conditions.

Figure 10A:
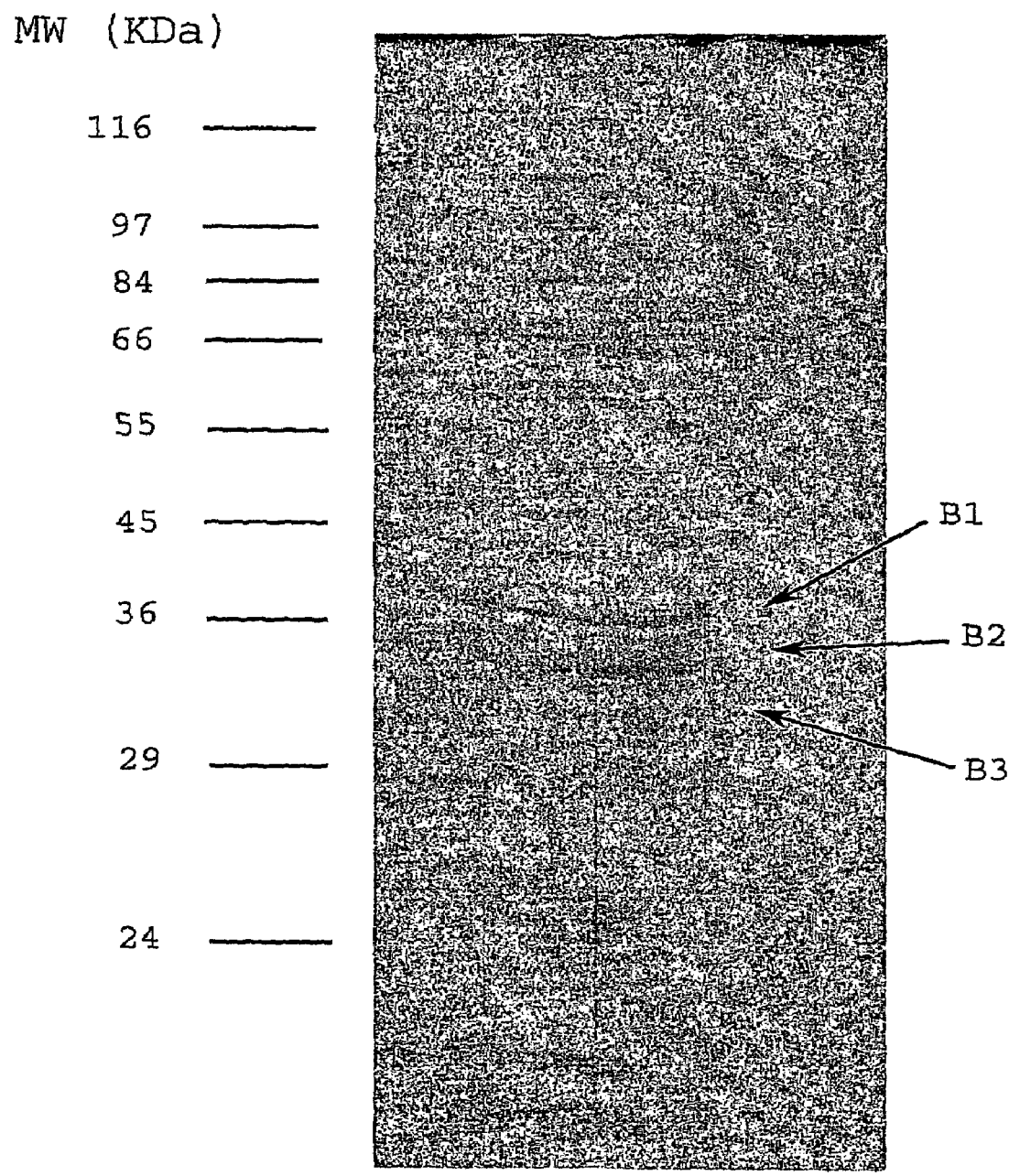

The purity of the purified 3-OST-5 was analyzed by SDS-PAGE followed by protein identification using mass spectrometry (FIG. 10). The purified protein predominantly migrated in three bands at 34 to 40 KDa, labeled as B1, B2 and B3 in FIG. 10A. The molecular weights of the observed bands are close to the calculated molecular weight of 37 KDa for 3-OST-5.

To further show that each band carried the amino acid sequences of 3-OST-5, the bands were cut from the gel, and subjected to in-gel trypsin digestion. The resulting peptides were analyzed by mass spectrometry. The results are shown in FIG. 10B. Numerous peptides from B2 and B3 were identified by MALDI-MS as having amino acid sequences from 3-OST-5. One tryptic peptide from B1 (having amino acid sequence AISDYTQVLEGKERK; SEQ ID NO 10) was also identified by Q-TOF. Taken together, these results confirmed that all three bands contained the amino acid sequences of 3-OST-5. The observed multiple bands for purified 3-OST-5 are likely to be the products of incomplete glycosylation or partial proteolysis in the Sf9 cells.

Example 8

Characterization of 3-OST-5 Modified HS

Figure 11:
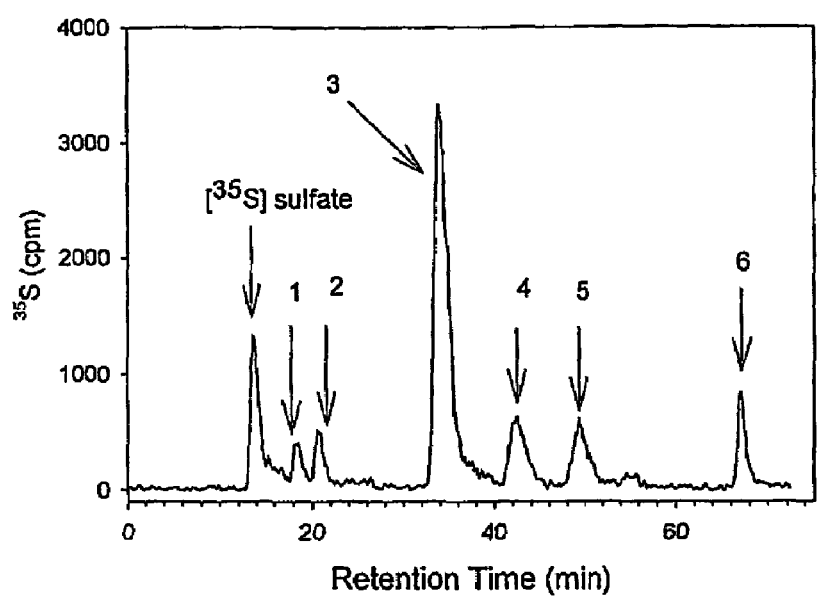
FIG. 11 depicts an RPIP-HPLC chromatogram of the disaccharide analysis of 3-OST-5-modified HS. Purified 3-OST-5 enzyme was incubated with unlabeled HS and [$^{35}$S] PAPS to prepare the 3-O-[$^{35}$S]sulfated HS. The [$^{35}$S]HS was degraded by nitrous acid at pH 1.5 followed by sodium borohydride reduction. The resulting $^{35}$S-labeled disaccharides were resolved by RPIP-HPLC. The elution positions of the disaccharide standards are indicated by arrows, where arrow 1 represents GlcUA-AnMan3S; arrow 2 represents IdoUA-AnMan3S; arrow 3 represents IdoUA2S-AnMan3S; arrow 4 represents IdoUA-AnMan3S6S; arrow 5 represents GlcUA-AnMan3S6S; and arrow 6 represents IdoUA2S-AnMan3S6S.

3-OST-5-modified HS was degraded by nitrous acid (pH 1.5), and the resulting disaccharides were resolved by RPIP-HPLC (FIG. 11). Three 3-O-[$^{35}$S]-sulfated disaccharides, IdoUA2S-[$^{35}$S]AnMan3S, GlcUA-[3-$^{35}$S]AnMan3S6S, and IdoUA2S-[3-$^{35}$S]AnMan3S6S were observed (labeled as Disaccharides 3, 5, and 6, respectively). These results suggested that the recombinant enzyme from insect cells has similar substrate specificity to that of the enzyme expressed in COS-7 cells. Disaccharide 1, 2, and 4 are all 3-O-[$^{35}$S]-sulfated disaccharides as described below.

The specificity of 3-OST-5 towards various glycosaminoglycans and desulfated heparins was tested (Table 6). Both heparin and HS serve as good receptors for 3-O-[$^{35}$S]sulfation, whereas hyaluronic acid, chondroitin sulfate A, and chondroitin sulfate B are not good substrates for 3-OST-5.

TABLE 6

Sulfation of glycosaminoglycans and desulfated heparins by 3-OST-5

| Substrates | Transferred [$^{35}$S]sulfate pmol/μg substrate |
|---|---|
| Heparin sulfate[a] | 5.00 ± 1.00 (n = 2) |
| Heparin[b] | 4.40 ± 1.10 (n = 2) |
| Hylauronic acid[b] | 0.50 ± 0.12 (n = 2) |
| Chondroitin sulfate A[b] | 0.30 ± 0.05 (n = 2) |
| Chondroitin sulfate B[b] | 0.20 ± 0.06 (n = 2) |
| De-NS-heparin[c] | 0.01 ± 0.01 (n = 2) |
| De-OS-heparin[c] | 0.01 ± 0.01 (n = 2) |
| De-2-OS-heparin[c] | 6.90 ± 1.50 (n = 2) |
| De-6-OS-heparin[c] | 4.00 ± 0.70 (n = 2) |

[a]Obtained from ICN
[b]Obtained from Sigma Chemical Company, St. Louis, Missouri, United States of America or Seikagaku, 1-5 Nihonbashi-honcho, 2-chome Chuo-ku, Tokyo 103-0023, Japan.
[c]De-NS-heparin, De-OS-heparin, De-2-OS-heparin and De-6-OS-heparin represent N-desulfated heparin, completely O-desulfated heparin, 2-O-desulfated heparin, and 6-O-desulfated heparin, respectively. They were obtained from Neoparin Inc. (San Leandro, California, United States of America).

The susceptibility of chemically desulfated heparins to 3-OST-5 modification was also examined. Both 2-O-desulfated heparin and 6-O-desulfated heparin serve as substrates for the enzyme. However, completely O-desulfated heparin is not a substrate for 3-OST-5. These results suggest that the enzyme requires either 2-O- or 6-O-sulfation for heparin to be modified by 3-OST-5. N-desulfated heparin is not a substrate, suggesting that N-sulfation is required for 3-OST-5 modification. It should be noted that heparin is not a substrate for 3-OST-3 (as opposed to HS; Liu, J., et al. (1999) J. Biol. Chem. 274:38155-38162), but is a substrate for 3-OST-1.

The binding of 3-OST-5-modified HS to HSV-1 glycoprotein D (gD) and antithrombin (AT) was determined. The 3-OST-5-modified HS was prepared by incubating [$^3$H]HS, which was isolated from CHO cells grown in medium containing [$^3$H]glucosamine, with purified 3-OST-5 enzyme. 3-OST-1-modified HS and 3-OST-3-modified HS were also prepared as positive controls for the binding to AT and gD, respectively. As shown in Table 7, 8.3% of 3-OST-5-modified HS bound to gD. About 19.8% 3-OST-5-modified HS bound to AT. Thus, 3-OST-5 generates both an AT-binding site and a gD binding site (Xia, G., et al. (2002) J. Biol. Chem. 277: 37912-37919).

TABLE 7

The bindings of 3-OST-5-modified HS to gD and AT

| | Binding to gD[a] (%) | Binding to AT[b] (%) |
|---|---|---|
| Control[c] | 0.4 ± 0.1 (n = 2) | 0.5 ± 0.1 (n = 3) |
| 3-OST-5 modified HS[d] | 8.3 ± 0.3 (n = 2) | 19.8 ± 0.2 (n = 3) |
| 3-OST-1 modified HS[d] | 2.1 ± 0.2 (n = 2) | 19.4 ± 1.0 (n = 3) |
| 3-OST-3 modified HS[d] | 9.4 ± 0.4 (n = 2) | 0.6 ± 0.1 (n = 3) |

[a]The binding of the HS and gD was determined by incubating modified [3H, 3-O-35S]HS with gD followed by immunoprecipitation using anti-gD monoclonal antibody (DL6) to precipitate the complex of HS and gD. The percentages binding to gD and AT were calculated based on 3H-counts. Data are presented as the mean ± range (or S.D.), where n represents the number of determinations.
[b]The binding of the HS and AT was determined by incubating modified HS and AT by using AT/ConA-Sepharose gel as described herein.
[c]Control was the [$^3$H]HS without enzymatic modifications.
[d]3-OST-1, 3-OST-3, and 3-OST-5 modified HS were prepared by incubating [3H]HS (from CHO-K1 cells), [$^{35}$S] PAPS, and purified 3-OST-1 (70 ng), 3-OST-3 (35 ng) and 3-OST-5 (70 ng), respectively.

The $K_m$s and $V_{max}$s of 3-OST-5 towards both HS and PAPS were also determined. The $V_{max}$ and $K_m$ for HS are 4.7 picomoles of sulfate/min and 1.6 μM, respectively. The $V_{max}$ and $K_m$ for PAPS are 4.7 picomoles of sulfate/min and 4.0 μM, respectively.

Example 9

Characterization of the Substrate Specificity of 3-OST-5

3-OST-5 Sulfates the Glucosamine Residue that is Linked to a Non-sulfated Iduronic Acid at the Non-reducing End As described in FIG. 11, three unidentified $^{35}$S-labeled components were detected in nitrous acid-degraded 3-OST-5-modified HS: Disaccharide 1 (eluting at 18.5 min), Disaccharide 2 (21.0 min), and Disaccharide 4 (43.0 min). Although the signals were relatively low, these components were consistently present. Disaccharides 1, 2, and 4 were purified by RPIP-HPLC to determine if they represented 3-O-sulfated disaccharides. Both Disaccharide 1 and Disaccharide 2 were eluted on RPIP-HPLC in a region where monosulfated disaccharides were expected to elute. Disaccharide 4 was eluted on RPIP-HPLC in a region where disulfated disaccharides were expected to elute. These observations suggested that Disaccharide 1 and Disaccharide 2 are monosulfated disaccharides, whereas Disaccharide 4 is a disulfated disaccharide.

The susceptibilities of Disaccharides 2 and 4 to β-glucuronidase and α-iduronidase digestions were determined. For Disaccharide 1, the $^{35}$S-peak was shifted from 81 min to 8 min after β-glucuronidase digestion on PAMN-HPLC, suggesting that Disaccharide 1 has the structure of GlcUA-AnMan3S. For Disaccharide 2, the $^{35}$S-peak was shifted from 86 min to 8 min on PAMN-HPLC after α-iduronidase digestion, suggesting that Disaccharide 2 has the structure of IdoUAAnMan3S (FIG. 12A). For Disaccharide 4, the $^{35}$S-peak was shifted from 110 min to 87 min after α-iduronidase digestion on PAMN-HPLC, and the resulting $^{35}$S-peak was co-eluted with AnMan3S6S standard, suggesting that Disaccharide 4 has the structure of IdoUA-AnMan3S6S.

3-OST-5 Sulfates N-sulfated Glucosamine and N-unsubstituted Glucosamine Residues It is known that 3-OST-1 and 3-OST-3 can sulfate N-sulfated glucosamine and N-unsubstituted glucosamine residues, respectively (Liu, J., et al. (1999) *J. Biol. Chem.* 274: 38155-38162; Zhang, L., et al. (2001) *J. Biol. Chem.* 276: 42311-42321). To determine which type of glucosamine residue was modified by 3-OST-5, a mixture of heparin lyases, including heparin lyase I, heparitinase I, heparitinase II, and heparitinase IV (the mixture hereinafter referred to as "heparin lyases"), was used to degrade 3-OST-5-modified HS. About 50% of [$^{35}$S]HS was degraded to disaccharides (or [$^{35}$S]sulfate) and 40% of [$^{35}$S]HS was degraded to tetrasaccharides (FIG. 13A). 3-O-sulfated HS, generated by 3-OST-1 and 3-OST-3, could not be degraded to disaccharides by a mixture of heparin lyases (Liu, J., et al. (1999) *J. Biol. Chem.* 274:38155-38162; Zhang, L., et al. (2001) *J. Biol. Chem.* 276:42311-42321).

Figure 13:
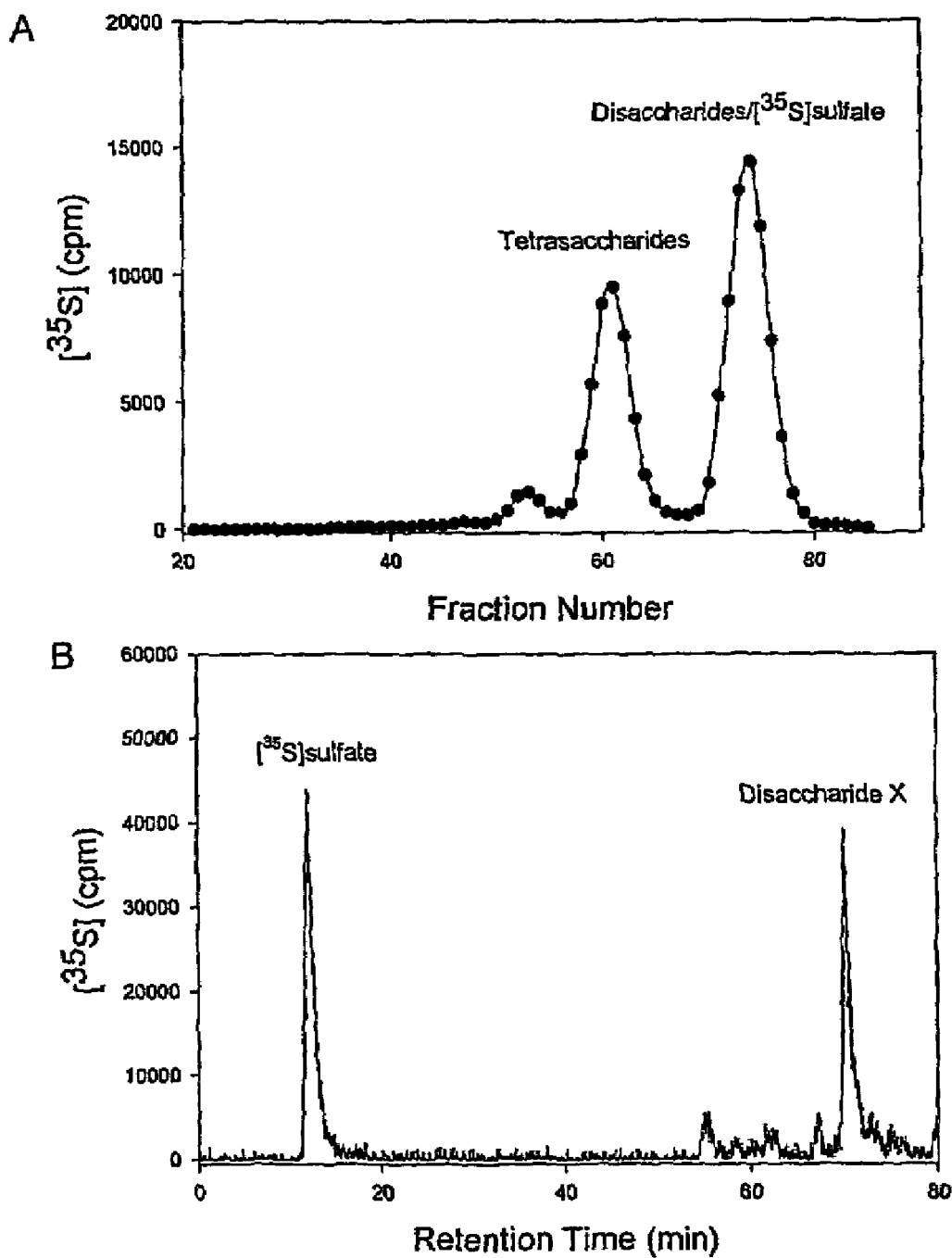
FIG. 13 B depicts the RPIP-HPLC chromatogram of the disaccharide fraction.

To further show that a $^{35}$S-labeled disaccharide was present in the heparin lyases-digested 3-OST-5-modified HS, the disaccharide pool was resolved using RPIP-HPLC (FIG. 13B). As shown in FIG. 13B, one major [$^{35}$S]-labeled disaccharide (Disaccharide X) eluted in a region consistent with it being a trisulfated disaccharide. In order to rule out that Disaccharide X is a tetrasulfated disaccharide, its molecular mass was determined by nESI-MS. A strong singly charged signal was observed at m/z 677.4, which is identical to the calculated molecular mass for a trisulfated disaccharide monotriethylammonium salt. Disaccharide X was eluted very close to a trisulfated disaccharide with the structure of ΔUA2S—GlcNS6S. Thus, Disaccharide X could potentially be contaminated with an unlabeled trisulfated disaccharide as both disaccharides have identical molecular mass. Given the fact that a signal that represented a tetrasulfated disaccharide was not observed, it appears that Disaccharide X is a trisulfated disaccharide.

The positions of the sulfate groups of Disaccharide X were determined by examining its susceptibilities to nitrous acid-degradation and $\Delta^{4,5}$-glycuronate-2-sulfatase (FIG. 14). The retention time of Disaccharide X on RPIP-HPLC was shifted from 72 min to 62 min by treating with nitrous acid at 15 pH 1.5 (FIG. 14A). However, a shift in retention time was not observed when the disaccharide was treated with nitrous acid at pH 4.5. These results suggest that Disaccharide X contains an N-sulfated glucosamine residue based upon the specificity of nitrous acid degradation at different pHs (Shively and Conrad, 1976).

Disaccharide X was susceptible to $\Delta^{4,5}$-glycuronate-2-sulfatase digestion. The retention time of Disaccharide X was shifted from 150 min to 138 min on PAMN-HPLC after the digestion by $\Delta^{4,5}$-glycuronate-2-sulfatase, suggesting it contains a ΔUA2S residue (FIG. 14B; see also McLean, M. W., et al. (1984) *Flavobacterium heparinum* 2-O-sulfatase for 2-O-sulfato-$\Delta_{4,5}$-glycuronate terminated oligosaccharides from heparin, *Eur J. Biochem* 145:607-615). Consistent with this conclusion, treatment of Disaccharide X with HS glycuronidase showed no shift in retention time on PAMN-HPLC. Taken together, these results suggest that Disaccharide X has a structure of ΔUA2SGlcNS3S.

Whether 3-OST-5 sulfates N-unsubstituted glucosamine residues was also investigated. Tetra-1 was isolated from the tetrasaccharide pool that was fractionated by BIOGEL® P-6 chromatography (Bio-Rad Labs) using PAMN-HPLC (FIG. 15A). Tetra-1 co-eluted with a previously published tetrasaccharide standard (ΔUA2S-GlcNS-IdoUA2S-GlcNH23S6S) on PAMN-HPLC, suggesting that Tetra-1 contains an N-unsubstituted glucosamine residue at the reducing end (see also Liu, J., et al. (2002) *J. Biol. Chem.* 277:33456-33467).

To further test whether Tetra-1 indeed carries an N-unsubstituted glucosamine residue, the susceptibility of Tetra-1 to nitrous acid degradation was tested at pH 4.5. It should be noted that the tetrasaccharide standard, ΔUA2S—GlcNS—IdoUA2S—GlcNH23S6S, undergoes nitrous acid degradation at pH 4.5 (Liu, J., et al. (1999) *J. Biol. Chem.* 274:38155-38162). As expected, the retention time of Tetra-1 was shortened from 46 min to 36 min on PAMN-HPLC after nitrous acid degradation (FIG. 15B), consistent with the conclusion that an N-unsubstituted glucosamine residue is present at the reducing end of Tetra-1.

Discussion of Examples 7-9

The 3-OST-5 enzyme was previously reported to generate both an AT-binding site and an entry receptor for HSV-1. The specificity of this enzyme was determined at the disaccharide level using crude cell extracts from COS-7 cells transfected with a plasmid expressing 3-OST-5 (Xia, G., et al. (2002) *J. Biol. Chem.* 277:37912-37919). As disclosed herein, the enzyme was produced in Sf9 cells using a baculovirus expression vector, where it was expressed at a high level and purified to apparent homogeneity. Using the purified enzyme, its substrate specificity was examined in greater detail, and the potential effects of other HS sulfotransferases on the action of 3-OST-5 were eliminated. The substrate specificity of 3-OST-5 is summarized in FIG. 16. These results demonstrated that the recombinant 3-OST-5 has very similar substrate specificity as the enzyme that was expressed in COS-7 cells as determined by the disaccharide analysis of 3-OST-5-modified HS. It was also determined that 3-OST-5-modified HS generated by the purified enzyme binds to antithrombin and HSV-1 gD. Taken together, these results suggested that the recombinant 3-OST-5 enzyme from Sf9 cells has similar enzymatic activity as the preparation that was prepared in mammalian cells.

Three additional 3-O-sulfated disaccharides were observed in nitrous acid-degraded (pH 1.5) 3-OST-5-modified HS, including GlcUA-AnMan3S, IdoUAAnMan3S, and IdoUA—AnMan3S6S. These structures were determined by examining their susceptibilities to β-glucuronidase and α-iduronidase digestion, respectively. Using the purified enzyme, a large amount of 3-OST-5-modified HS was prepared, which allowed for a sufficient amount of the disaccharide to be obtained to investigate its structure. In addition, the presence of GlcUA-AnMan3S and IdoUA—AnMan3S was also shown. Taken together, these results suggested that 3-OST-5 sulfates a glucosamine residue that is linked to an iduronic acid residue at the non-reducing end.

3-OST-5 enzyme sulfates both N-sulfated glucosamine (GlcNS) and N-unsubstituted glucosamine (GlcNH2) residues. This conclusion was based upon the structural analysis of the products of heparin lyases-digested 3-OST-5-modified HS. Given the fact that 3-OST-1 sulfates GlcNS and 3-OST-3 sulfates GlcNH2, the presently disclosed results suggested that 3-OST-5 has a more relaxed substrate specificity. A 3-O-sulfated disaccharide with a structure of ΔUA2S-GlcNS3S from the heparin lyases-digested products was observed. It was reported that HS tetrasaccharides containing 3-O-sulfated glucosamine residues are resistant to digestion by heparin lyases (Liu, J., et al. (1999) *J. Biol Chem.* 274:38155-38162; Sundaram et al. (2003) *Proc Natl Acad Sci* 100:651-656; Yamada et al. (1995) *J Biol Chem* 270:8696-8705; Zhang, L., et al. (1999) *J. Biol. Chem.* 274:5681-5691).

Indeed, only tetra- and hexasaccharides were found in the products of heparin lyases-digested 3-OST-3-modified HS.

Materials Used in Examples 7-9

A human 3-OST-5 expression plasmid (pcDNA3.1-3OST5) was prepared as described previously (Xia, G., et al. (2002) *J. Biol. Chem.* 277:37912-37919). Recombinant human 3-OST-3A and mouse 3-OST-1 were expressed in Sf9 cells using a baculovirus expression system and purified by Heparin-SEPHAROSE™ CL-6B (Amersham Biosciences, Piscataway, N.J., United States of America) and 3',5'-ADP-agarose (Sigma Chemical Company, St. Louis, Mo., United States of America) chromatographies (Hernaiz, M., et al. (2000) *Biochem. Biophys. Res. Commun.* 276:292-297; Liu, J., et al. (1999) *J. Biol. Chem.* 274:38155-38162). [$^{35}$S]PAPS was prepared by incubating 0.4 to 2 mCi/ml [$^{35}$S]Na$_2$SO$_4$ (carrier free; ICN) and 16 mM ATP with 5 mg/ml dialyzed yeast extract (Sigma Chemical Company, St. Louis, Mo., United States of America; see Bame and Esko, 1989). HS was from ICN. $^3$H-labeled HS was purified from wild type Chinese hamster ovary (CHO) cells, which were grown in media containing $^3$H-glucosamine (ICN; see Zhang, L., et al. (1999) *J. Biol. Chem.* 274:5681-5691). Human antithrombin (AT) is from Cutter Biological (Berkeley, Calif., United States of America). Desulfated heparins were obtained from Neoparin Inc. (San Leandro, Calif., United States of America). A truncated form of HSV-1, glycoprotein D (gD-1306t), and monoclonal anti-gD (DL6) were generous gifts of Drs. Cohen and Eisenberg of University of Pennsylvania (Philadelphia, Pa., United States of America; see Nicola, A. V., et al. (1996) *J. Virol.* 70:3815-3822). Heparitinase IV, $\Delta^{4,5}$-glycuronate-2-sulfatase, and HS glycuronidase were gifts from Dr. Keiichi Yoshida (Tokyo Research Institute of Seikagaku Corporation, Tokyo, Japan). The $^3$H-labeled disaccharide standards IdoUA—AnMan6S, IdoUA2S—AnMan, GlcUA-AnMan3S6S, and IdoUA2S—AnMan6S were prepared from $^3$H-labeled heparin as per Shworak, N. W., et al. (1994) *J. Biol. Chem.* 269:24941-24952. The $^{35}$S-labeled disaccharide standards, IdoUA2S—AnMan3S and IdoUA2S—AnMan3S6S, were purified from nitrous acid (pH 1.5)-degraded HS that was modified by purified 3-OST-3 enzyme as described by Liu, J., et al. (1999) *J. Biol. Chem.* 274:38155-38162. Iduronate 2-sulfatase and α-iduronidase were from Glyko (Novato, Calif., United States of America). β-glucuronidase was from Sigma Chemical Company, St. Louis, Mo., United States of America.

Preparation of Recombinant 3-OST-5 Enzyme

Preparation of 3-OST-5 Baculovirus Expression Plasmid

The secreted form of 3-OST-5 was constructed by removing 29 amino acid residues from the N-terminus consisting of the proposed TM (Xia, G., et al. (2002) *J. Biol. Chem.* 277: 37912-37919). The construction of the expression plasmid involved two-step cloning. A partial 3-OST-5 cDNA (about 900 bp) was first cloned from pcDNA3.1-3OST5 into the baculovirus expression vector containing a honeybee melittin signal using EcoR I/Xba I sites (Liu, J., et al. (1999) *J. Biol. Chem.* 274:38155-38162; Xia, G., et al. (2002) *J. Biol. Chem.* 277:37912-37919). The remaining 3-OST-5 sequence was amplified by a PCR reaction using two specific primers and pcDNA3.1-3OST5 as a template. The sequences of the two specific primers are: 5'-primer AATTT<u>GGATCC</u>CCAGAGTTGGGAGCTTGGATAG (SEQ ID NO 11) with a BamHI I site (underlined); 3'-primer AACAAAACTTATTACAAGTTTGAGA (SEQ ID NO 12). The PCR product (559 bp) was digested with BamHI I and EcoR I to yield a fragment of 82 basepairs (bp). The resulting 82 bp fragment was then cloned into the construct that contains part of 3-OST-5 sequence using the BamHI I and EcoR I sites. The reading frame was confirmed by sequencing analysis. The construct does not contain the (His)$_6$ sequence.

Expression of 3-OST-5

A 3-OST-5 recombinant baculovirus was prepared from the 3-OST-5 baculovirus expression plasmid using the BAC-TO-BAC® baculovirus system (Invitrogen Corporation, Carlsbad, Calif., United States of America) according to the manufacture's protocol. Briefly, Sf9 cells ($1 \times 10^6$ cells/ml, Invitrogen Corporation, Carlsbad, Calif., United States of America) were grown in serum-free media in a spinner bottle and infected with 3-OST-5 recombinant virus. The medium was harvested 72 hours after infection. The harvested medium was centrifuged at 1000×g for 15 minutes, and 3-[(3-cholamidopropyl)diethylammonio]-1-propane sulfonate (CHAPS) was added to a final concentration of 0.6%. This solution was frozen in liquid nitrogen and stored at −80° C. for subsequent purification.

Measurement of 3-OST-5 Activity

The activity of 3-OST-5 was determined by measuring the amount of [$^{35}$S]sulfate transferred to HS polysaccharide. A similar method was used to determine the activity of 3-OST-3 (Liu, J., et al. (1999) *J. Biol. Chem.* 274:38155-38162). Briefly, a typical 50 μl reaction contained various amount of 3-OST-5 enzyme, 200 μg/ml HS, $1 \times 10^7$ cpm of [$^{35}$S]PAPS, 50 mM MES, pH 7.0, 10 mM MnCl$_2$, 5 mM MgCl$_2$, 100 mM NaCl, 120 μg/ml bovine serum albumin, and 1% TRITON® X-100 (v/v). The reaction mixture was incubated at 37° C. for 1 hour. The [$^{35}$S]HS was isolated using a DEAE-Sephacel column (Xia, G., et al. (2002) *J. Biol. Chem.* 277:37912-37919).

Purification of Recombinant 3-OST-5

The entire purification was carried out at 4° C. The harvested medium (about 1.5 liters) was mixed with 4-[N-morpholino]propanesulfonic acid (MOPS) to a final concentration of 20 mM and adjusted to pH to 7.0 with 1 M NaOH. The preparation was centrifuged to remove insoluble particles. The supernatant was mixed with an equal volume of cold 20 mM MOPS, pH 7.0, and then loaded on a Heparin-SEPHAROSE™ CL-6B column (1×10 cm) (Amersham Biosciences, Piscataway, N.J., United States of America), which was equilibrated with MCG Buffer (20 mM MOPS, 0.6% CHAPS, 2% glycerol, pH 7.0), and 150 mM NaCl, at 4 ml/min. The column was then washed with MCG buffer containing 150 mM NaCl for 20 min and eluted with a linear gradient of NaCl from 150 mM to 1000 mM in 50 min. The fractions (48 ml) containing 3-OST-5 activity were pooled and dialyzed against 50 mM NaCl in MCG buffer. The solution was then loaded on a 3',5'-ADP-agarose column (0.5×8 cm), which was equilibrated with 150 mM NaCl in MCG buffer at 0.3 m/min. The column was washed with MCG buffer containing 150 mM NaCl for 33 min and eluted with a linear gradient of NaCl from 150 mM to 1000 mM in 67 min followed by a 17 minute wash with 1000 mM NaCl in MCG buffer. The fractions (8 ml) containing 3-OST-5 activity were pooled.

Protein Identification by Matrix-assisted Laser Desorption/Ionization Mass Spectrometry (MALDI-MS/MS)

Purified 3-OST-5 was in-gel digested with a GENOMICS SOLUTIONS™ ProGest robot (GENOMICS SOLUTIONS™, Ann Arbor, Mich., United States of America)

using trypsin in 50 mM ammonium bicarbonate at pH 8 (Borchers et al., 2000). Extracted peptides were lyophilized and reconstituted in 5 µl of 50% methanol/0.1% formic acid (v/v). Peptides (0.5 µl) were mixed with 1 µl of saturated α-cyanohydroxycinnamic acid in 50% acetonitrile/0.1% TFA and analyzed using both a Bruker Reflex III MALDI-TOF and a 4700 MALDI-TOF/TOF (Applied Biosystems, Foster City, Calif., United States of America). For protein identification, Mascot software (www.matrixscience.com) (Matrix Science Ltd., London, United Kingdom) was used for matching molecular mass of peptides against the NCBInr database (as of Feb. 15, 2003). The digest (Band 1 on the gel in FIG. 11B) was also analyzed by LC-MS/MS on a Waters Q/TOF API US coupled to a Waters CapLC using a 75 min gradient elution on a LCPackings 75 µm×15 cm PepMap C18 reverse phase column.

Characterization of 3-OST-5 Modified HS

Preparation of 3-OST-5-Modified HS

Purified 3-OST-5 (70 ng) was mixed with 1 µg of HS and 20 µM [$^{35}$S]PAPS (1×10$^7$ cpm) in the enzyme reaction buffer as described above. Twenty reactions were prepared to obtain enough 3-OST-5-modified HS for structure analysis. Alternatively, the HS was replaced by $^3$H-labeled HS (0.1 µg), which was prepared from [3H]glucosamine (ICN) metabolically labeled CHO cells.

Determination of 3-OST-5 Modified HS Binding to AT and to gD

The binding of 3-OST-5-modified HS to AT was determined using an AT/Concanavalin A (conA)-SEPHAROSE® (Sigma Chemical Company, St. Louis, Mo., United States of America) approach (Liu, J., et al. (1996) *J. Biol. Chem.* 271: 27072-27082). The assay for determining the binding of 3-OST-5-modified HS to gD was carried out by an immunoprecipitation procedure using anti-gD monoclonal antibody (Shukla, D., et al. (1999) *Cell* 99:13-22).

Disaccharide Analysis

The [$^{35}$S]HS was degraded by nitrous acid (pH 1.5) followed by reduction with sodium borohydride (Shively, J. E., and Conrad, H. E. (1976) *Biochemistry* 15:3932-3942). The resulting disaccharides were desalted on a BIOGEL® P-2 column (0.5×200 cm), which was equilibrated with 0.1 M ammonium bicarbonate at 4 ml/hour. The disaccharides were then resolved by reverse phase ion-pairing HPLC (RPIP-HPLC) to determine the identities of $^{35}$S-labeled disaccharides by co-eluting with appropriate standards (Liu, J., et al. (2002) *J. Biol. Chem.* 277:33456-33467; Xia, G., et al. (2002) *J. Biol. Chem.* 277:37912-37919).

Enzymatic Digestion of 3-O-[35S]Heparin Sulfate

The conditions used for digesting HS by a mixture of heparin lyases, including heparinase, heparitinase I, heparitinase II, and heparitinase IV, were previously described (Zhang, L., et al. (1999) *J. Biol. Chem.* 274:5681-5691). The conditions for the digestion with α-iduronidase and β-glucuronidase were previously described (Liu, J., et al. (1999) *J. Biol. Chem.* 274:38155-38162). The conditions for the digestions by Δ$^{4,5}$-glycuronate-2-sulfatase and HS glycuronidase were previously described (Liu, J., et al. (2002) *J. Biol. Chem.* 277:33456-33467).

HPLC

Both RPIP-HPLC and anion-exchange HPLC were employed to resolve 3-O-[$^{35}$S]sulfated disaccharides and 3-O-[$^{35}$S]tetrasaccharides. For the analysis of the mixture of disaccharides containing trisulfated disaccharides, a $C_{18}$-reversed phase column (0.46×25 cm, GraceVydac, Conn., United States of America) was used under reverse-phase ion-pairing HPLC (RPIP-HPLC) conditions (Liu, J., et al. (1999) *J. Biol. Chem.* 274:38155-38162). The column was eluted with acetonitrile (8% for 45 min, 15% for 15 min, and 19.5% for 30 min) in a solution containing 38 mM ammonium phosphate monobasic, 2 mM phosphoric acid, and 1 mM tetrabutylammonium phosphate monobasic (Fluka, Switzerland) at a flow rate of 0.5 ml/min. For the analysis of monosulfated disaccharides, the column was eluted with acetonitrile (4.8% for 45 min, 9% for 15 min, and 11.7% for 120 min) in a solution containing 9.5 mM ammonium phosphate monobasic, 0.5 mM phosphoric acid, and 1 mM tetrabutylammonium phosphate monobasic at 0.5 ml/min.

For the analyses of α-iduronidase-, β-glucuronidase-, and Δ$^{4,5}$-glycuronate-2-sulfatase-treated 3-O-[$^{35}$S]sulfated disaccharides, a silica-based polyamine HPLC (PAMN-HPLC) column (0.46×25 cm, Waters) was employed. The column was eluted with 30 mM $KH_2PO_4$ for 70 minutes followed by a linear gradient of $KH_2PO_4$ from 30 to 1000 mM in 130 min at a flow rate of 0.8 ml/min. To isolate 3-O-[$^{35}$S]sulfated tetrasaccharides, the PAMN-HPLC column was eluted with a linear gradient of $KH_2PO_4$ from 350 mM to 1000 mM in 60 min followed by additional wash with 1000 mM $KH_2PO_4$ for 20 min each at a flow rate of 0.8 ml/min.

Nanoelectrospray Ionization Mass Spectrometry (nESI-MS)

nESI-MS analysis was performed on a Micromass Quattro II with QhQ 10 geometry, a Z-spray source, and pulled borosilicate glass nanovials. The conditions for the analysis of HS disaccharides were previously described (Pope et al. (2001) *Glycobiology* 11:505-513). An extensive desalting procedure was used in order to obtain the MS spectrum of Disaccharide X. The disaccharide was desalted by a DEAE-Sephacel column, and the disaccharide was eluted with 1 M triethylammonium bicarbonate (pH 8). The resulting disaccharide was further desalted by a BIOGEL® P-2 column, which was eluted with 0.1 M ammonium acetate at a flow rate of 4 ml/hr.

Kinetic Analysis

The kinetic constants ($K_m$ and $V_{max}$) of 3-OST-5 vis-à-vis HS and PAPS were determined. The reactions were allowed to proceed for 5 min, and the reaction velocity represented the initial velocity.

To determine the $K_m$ and $V_{max}$ with respect to HS, various concentrations of HS (0.125 to 8 µM) were employed in a standard 50-µl reaction as described above, containing 20 µM $^{35}$S-PAPS (1×10$^7$ cpm). Reactions were quenched by adding 100 µl of a buffer containing 50 mM sodium acetate, 6 M urea, 150 mM NaCl, 1 mM EDTA and 0.1% TRITON® X-100, pH 5.5. The samples were then subjected into a 200 µl DEAE-SEPHAROSE™ column. The [$^{35}$S]HS produced was eluted from the column by 1000 mM NaCl (Liu, J., et al. (1996) *J. Biol. Chem.* 271:27072-27082).

To determine the $K_m$ and $V_{max}$ with respect to PAPS, various concentrations of unlabeled PAPS (from 1 to 20 µM) and 1×10$^7$ cpm [$^{35}$S]PAPS were employed in a standard 50 µl-reaction. The reactions were quenched after 5 min incubation.

The corresponding initial velocities were plotted against the concentrations of HS or PAPS. The plot was fitted to the equation $V=V_{max} S/(K_m+S)$, where S represents the concentration of HS or PAPS, to obtain $K_m$ and $V_{max}$.

REFERENCES

The publications and other materials listed below and/or set forth by author and date in the text above to illuminate the background of the invention, and in particular cases, to provide additional details respecting the practice, are incorporated herein by reference. Materials used herein include but are not limited to the following listed references.

Adelman et al. (1983) DNA 2:183.
Aikawa et al. (2001) *J. Biol. Chem.* 276:5876-5882
Akkaraju et al. (1999) *J. Gene Med.* 1:280-289
Alexander et al. (2000) *Nat. Genet.* 25:329-332
Altschul et al. (1990) *J Mol Biol* 215:403-410.
Altschul et al. (1997) *Nucleic Acids Res* 25(17):3389-3402.
Amial et al. (1994) *Am J Physiol Cell Physiol* 267:C1607-1625.
Armour et al. (1996) *Ann Hum Genet* 60:11B20.
Beaucage et al. (1981) *Tetrahedron Letters* 22:1859-1862.
Bernfield et al. (1999) *Annu. Rev. Biochem.* 68:729-777
Bize et al. (1999) *Am J Physiol* 277:C926-936.
Bjornsson, S. (1993) *Anal. Biochem.* 210:282-291
Brookes (1999) *Gene* 234(2):177-186.
Brugnara et al. (1986) *Science* 232(4748):388-390.
Callenbach & Brouwer (1997) *Clin Neurol Neurosurg* 99(3): 159-171.
Capecchi (1989) *Science* 244(4910):1288-1292.
Carfi et al. (2001) *Mol. Cell* 8:169-179
Casaubon et al. (1996) *Am J Hum Genet* 58(1):28-34.
Chien et al. (1991) *Proc Natl Acad Sci USA* 88:9578-9582.
Clayton et al. (1998) *Brain Res Dev Brain Res* 109(2):281-292.
Conner et al. (1983) *Proc Natl Acad Sci USA* 80:278.
De Franceschi et al. (1996) *Blood* 88(7):2738-2744.
Delpire et al. (1999) *Nat. Genet.* 22(2):192-195.
Dennissen et al. (2002) *J. Biol. Chem.* 277:10982-10986
Di Stefano et al. (1998) *Cell Physiol Biochem* 8:89-105.
Ding et al. (1997) *J Biol Chem* 272(44):28142-28148.
Elmslie et al. (1997) *Hum Mol Genet* 6(8):1329-1334.
Esko & Lindahl (2001) *J. Clin. Invest.* 108:169-173
Forlino et al. (1999) *J Biol Chem* 274(53):37923-37931.
Garay et al. (1988) *Mol Pharmacol* 33:696-701.
Gatti et al. (1988) *Nature* 336:577-580.
Gebhardt et al. (1999) *J Biol Chem* 274:13176-13180.
Gillen et al. (1996) *J Biol Chem* 271(27):16237-16244.
Giménez et al. (1999) *FASEB J* 13:A64.
Greger & Schlatter (1983) *Pflugers Arch* 396:325-334.
Gribskov et al. (1986) *Nuc Acids Res* 14(1):327-334.
Grobe & Esko (2002) *J. Biol. Chem.* 277:30699-30706
Grunder et al. (1992) *Nature* 360(6406):759-762.
Habuchi et al. (2000) *J. Biol. Chem.* 275:2859-2868
Hara et al. (1992) *Neurosci Lett* 143:135-138.
Hardt et al. (2000) *J Comp Pathol* 122:43-53.
Harlow & Lane (1988) *Antibodies: A Laboratory Manual*, Cold Spring Harbor Laboratory Press, Cold Spring Harbor, N.Y.
Hernaiz et al. (2000) *Biochem. Biophys. Res. Commun.* 276: 292-297
Hiki et. al. (1999) *J Biol Chem* 274:10661-10667.
Hochman et al. (1995) *Science* 270(5233):99-102.
Holtzman et al. (1998) *Am J Physiol* 275(4 Pt 2):F550-564.
Hubner et al. (2001) *Mech Dev* 102:267-269.
Hurst et al. (1992) *Am J Physiol* 263(2 Pt 2):F262-267.
Isenring et al. (1998) *J Gen Physiol* 112(5):549-558.
Jacoby (1999) *Am J Physiol* 277:C684-692.
Jenniskens et al. (2000) *J. Neurosci.* 20:4099-4111
Ji et al. (1998) *Am J Physiol* 275(5 Pt 1):C1182-1190.
Karadesh & Delpire (2001) *J Neurophysiol* 85:995-997.
Kelley et al. (2000) *J Membr Biol* 178:31-41.
Kestila et al. (1998) *Mol Cell* 1(4), 575-582.
Kissel et al. (2000) *EMBO J* 19(6):1312-1326.
Krapivinsky et al. (1994) *Cell* 76(3):439-448.
Krummenacher et al. (1999) *J. Virol.* 73:8127-8137
Kuwahara et al. (1997) *Biochemistry* 36:13973-13978.
Kyte et al. (1982) *J Mol Biol* 157:105.
Lafreniere et al. (1997) *Nat Genet* 15(3):298-302.
Landgren et al. (1988) *Science* 241:1007.
Landgren et al. (1988) *Science* 242:229-237.
Lauf et al. (1992) *Am J Physiol* 263:C917-932.
Lee & Lander (1991) *Proc. Natl. Acad. Sci. USA* 88:2768-2772.
Liapis et al. (1998) *Am J Physiol* 275(6 Pt 1):C1432-1437.
Liman et al. (1992) *Neuron* 9:861-871.
Lindahl et al. (1980) *Proc. Natl. Acad. Sci. U. S. A.* 77:6551-6555
Lindah et al. (1998) *J. Biol. Chem.* 273:24979-24982
Liu & Rosenberg (2002) in *Handbook of Glycosyltransferases and Their Related Genes* (Taniguchi, N., and Fukuda, M., eds), pp. 475-483, Springer-Verlag, Tokyo
Liu & Thorp (2002) *Med. Res. Rev.* 22:1-25
Liu et al. (1999) *J. Biol. Chem.* 274:38155-38162
Liu et al. (2002) *J. Biol. Chem.* 277:33456-33467
Liu et al. (1996) *J. Biol. Chem.* 271:27072-27082
Liu, J., Shworak, N. W., Sinaÿ, P., Schwartz, J. J., Zhang, L., Fritze, L. M. S., and Rosenberg, R. D. (1999) *J. Biol. Chem.* 274:5185-5192
Loghman-Adham et al. (1997) *Kidney Int* 52(1):229-239.
Lopes et al. (1988) *Proc Natl Acad Sci USA* 85(8):2873-2877.
Lu et al. (1999) *J Neurobiology* 39:558-568.
Luyckx et al. (1999) *Proc Natl Acad Sci USA* 96(21):12174-12179.
Lytle (1998) *Am J Physiol* 274:C1002-1010.
Makalowski & Boguski (1998) *Proc Natl Acad Sci USA* 95:9407B9412.
Maniatis et. al. (1982) in *Molecular Cloning: A Laboratory Manual*, Cold Spring Harbor Laboratory Press, New York, N.Y.
Martinez Murillo et al. (1999) *Neurology* 53(1):50-56.
McLean et al. (1984) *Flavobacterium heparinum* 2-O-sulfatase for 2-O-sulfato-$\Delta_{4,5}$-glycuronate terminated oligosaccharides from heparin, *Eur J. Biochem* 145:607-615.
McKeehan et al. (1999) *J. Biol. Chem.* 274:21511-21514
McPherson et al., eds. (1991) *PCR. A Practical Approach*, IRL Press, Oxford University Press, New York, N.Y.
McLean et al. (1984) *Eur J Biochem* 145:607-615.
Mercado et al. (2000) *J Biol Chem* 275:30326-3034.
Miles (1999) *Nature* 397(6716):215-216.
Misgeld et al. (1986) *Science* 232(4756):1413-141.
Needleman et al. (1970) *J Mol Biol* 48:443.
Neelands et al. (1998) *J Neurosci* 18(13):4993-5007.
Neelands et al. (1999) *J Neurosci* 19(16):7057-7065.
Negish et al. (2001) *Arch. Biochem. Biophys.* 390:149-157
Neubauer et al. (1998) *Neurology* 51(6):1608-1612.
Nicola et al. (1996) *J. Virol.* 70:3815-3822.
Orita et al. (1989) *Proc Natl Acad Sci USA* 86(8):2766-2770.
Payne (1997) *Am J Physiol* 273:C1516-C1525.
Payne et al. (1990) *Am J Physiol* 259:C819-827.
Piontek et al. (1999) *J Neurochem* 73(1):139-146.
Pleasure & Lee (1993) *J Neurosci Res* 35(6):585-602.
Pope et al. (2001) *Glycobiology* 11:505-513.
Price (1993) *Blood Rev* 7:127-134.
Reed et al. (1999) *Am J Hum Genet* 64(5):1478-1480.
Reizes et al. (2001) *Cell* 106:105-116
Rivera et al. (1999) *Nature* 397:251-255.
Rose et al. (1991) *Kidney Int* 39:336-352.
Rosenberg et al. (1997) *J. Clin. Invest.* 99:2062-2070
Saiki et al. (1985) *Bio/Technology* 3:1008-1012.

Sambrook et al. (2001) *Molecular Cloning: A Laboratory Manual*, Third Edition, Cold Spring Harbor Laboratory Press, Cold Spring Harbor, N.Y.
Sauer (1998) *Methods* 14(4):381-392.
Schoenherr et al. (1996) *Proc Natl Acad Sci USA* 93:9881-9886.
Schultz et al. (1998) *Proc Natl Acad Sci USA* 95:5857-5864.
Schultz et al. (2000) *Nuc Acids Res* 28:231-234.
Schwartz et al., (1979) *Nuc Acids Res* 6(2):745-755.
Seki et al. (1993) *J Clin Invest* 92(3):1229-1235.
Shieh et al. (1992) *J. Cell Biol* 116:1273-1281
Shimajiri et al. (1999) *FEBS Lett* 455:70-74.
Shively & Conrad (1976) *Biochemistry* 15:3932-3942
Shukla & Spear (2001) *J. Clin. Invest.* 108:503-510
Shukla et al. (1999) *Cell* 99:13-22
Shworak et al. (1997) *J. Biol. Chem.* 272:28008-28019
Shworak et al. (1999) *J. Biol. Chem.* 274:5170-5184
Shworak et al. (1994) *J. Biol. Chem.* 269:24941-24952
Simon et al. (1996) *Nat Genet* 13(2):183-188.
Simon et al. (1996) *Nat Genet* 14:152-156.
Simon et al. (1997) *Nat Genet* 17:171-178.
Skradski et al. (1998) *Genomics* 49(2):188-192.
Smith et al. (1981) *Adv Appl Math* 2:482.
Stober et al. (2000) *Am J Hum Genet* 67:1201-1207.
Stoneking et al. (1991) *Am J Hum Genet* 48(2):370-382.
Su et al. (1999) *Am J Physiol* 277(5 Pt 1):C899-C912.
Sundaram et al. (2003) *Proc Natl Acad Sci* 100:651-656.
Thomas & Capecchi (1990) *Nature* 346(6287):847-850.
Thompson et al. (1994) *Nuc Acids Res* 22(22):4673-4680.
Timchenko & Caskey (1996) *FASEB J* 10(14):1589-1597.
Tomlinson et al. (1999) *Gastroenterology* 116(4):789-795.
Trask (1991) *Trends Genet* 7:149-154.
U.S. Pat. No. 4,196,265
U.S. Pat. No. 4,458,066
U.S. Pat. No. 4,554,101
U.S. Pat. No. 4,683,195
U.S. Pat. No. 4,683,202
U.S. Pat. No. 4,736,866
U.S. Pat. No. 4,769,331
U.S. Pat. No. 4,895,807
U.S. Pat. No. 4,965,188
U.S. Pat. No. 5,162,215
U.S. Pat. No. 5,234,933
U.S. Pat. No. 5,260,203
U.S. Pat. No. 5,279,833
U.S. Pat. No. 5,286,634
U.S. Pat. No. 5,326,902
U.S. Pat. No. 5,352,660
U.S. Pat. No. 5,399,346
U.S. Pat. No. 5,410,031
U.S. Pat. No. 5,441,875
U.S. Pat. No. 5,489,742
U.S. Pat. No. 5,550,316
U.S. Pat. No. 5,573,933
U.S. Pat. No. 5,580,722
U.S. Pat. No. 5,614,396
U.S. Pat. No. 5,625,125
U.S. Pat. No. 5,627,158
U.S. Pat. No. 5,641,484
U.S. Pat. No. 5,643,567
U.S. Pat. No. 5,645,999
U.S. Pat. No. 5,646,008
U.S. Pat. No. 5,648,061
U.S. Pat. No. 5,651,964
U.S. Pat. No. 5,734,033
U.S. Pat. No. 5,739,278
U.S. Pat. No. 5,741,957
U.S. Pat. No. 5,786,152
U.S. Pat. No. 5,834,228
U.S. Pat. No. 5,837,479
U.S. Pat. No. 5,846,720
U.S. Pat. No. 5,849,578
U.S. Pat. No. 5,872,011
Van den Pol et al. (1996) *J Neurosci* 16(13):4283-4292.
Vandorpe et al. (1998) *J Biol Chem* 273(34):21542-21553.
Verma et al. (1988) *Human Chromosomes: A Manual of Basic Techniques*, Pergamon Press, New York, N.Y.
Wang et al. (1998) *Science* 280(5366):1077-1082.
Wang et al. (2000) *Am. J. Physiol.* 278:C619-C626
Wethmur & Davidson (1968) *J Mol Biol* 31:349-370.
White et al. (1997) *Nat Genet* 17(4):404-410.
Wick et al. (1996) *Oncogene* 12(5):973-978.
Williams et al. (1999) *J Biol Chem* 274(18):12656-12664.
Willis et al. (1998) *J. Virol.* 72:5938-5947
WO 84/03564
WO 93/25521
WO 96/34288
WO 98/29431
WO 98/37198
WO 98/53067
WuDunn & Spear (1989) *J. Virol.* 63:52-58
Xia et al. (2002) *J. Biol. Chem.* 277:37912-37919
Yabe et al. (2001) *Biochem. J.* 359:235-241.
Yamada et al. (1995) *J Biol Chem* 270:8696-8705.
Ye et al. (1999) *Hum Mutat* 14(5):440-446.
Zhang et al. (2001) *J. Biol. Chem.* 276:42311-42321
Zhang et al. (1999) *J. Biol. Chem.* 274:5681-5691.

It will be understood that various details of the invention can be changed without departing from the scope of the invention. Furthermore, the foregoing description is for the purpose of illustration only, and not for the purpose of limitation—the invention being defined by the claims.

What is claimed is:

1. An isolated and purified biologically active heparan sulfate 3-O-sulfotransferase 5 polypeptide having the amino acid sequence set forth in SEQ ID NO 2.

2. The isolated and purified biologically active heparan sulfate 3-O-sulfotransferase 5 polypeptide of claim 1, wherein the polypeptide comprises the polypeptide encoded by the nucleic acid sequence as set forth in SEQ ID NO 1.

3. The polypeptide of claim 1, wherein the polypeptide is the human heparan sulfate 3-O-sulfotransferase 5 polypeptide.

4. The polypeptide of claim 1, wherein the polypeptide is modified to be in detectably labeled form.

* * * * *